(12) United States Patent
Sentman

(10) Patent No.: US 10,689,617 B1
(45) Date of Patent: *Jun. 23, 2020

(54) T-CELL RECEPTOR-DEFICIENT T CELL COMPOSITIONS

(71) Applicant: THE TRUSTEES OF DARTMOUTH COLLEGE, Hanover, NH (US)

(72) Inventor: Charles L. Sentman, West Lebanon, NH (US)

(73) Assignee: THE TRUSTEES OF DARTMOUTH COLLEGE, Hanover, NH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/815,261

(22) Filed: Nov. 16, 2017

Related U.S. Application Data

(62) Division of application No. 15/383,717, filed on Dec. 19, 2016, now Pat. No. 9,821,011, which is a division of application No. 14/934,256, filed on Nov. 6, 2015, now Pat. No. 9,957,480, which is a division of application No. 13/502,978, filed as application No. PCT/US2010/054846 on Oct. 29, 2010, now Pat. No. 9,181,527.

(60) Provisional application No. 61/255,980, filed on Oct. 29, 2009.

(51) Int. Cl.
| | |
|---|---|
| *C12N 5/0783* | (2010.01) |
| *A61K 39/00* | (2006.01) |
| *A61K 35/17* | (2015.01) |
| *A61K 35/12* | (2015.01) |

(52) U.S. Cl.
CPC ............ *C12N 5/0636* (2013.01); *A61K 35/17* (2013.01); *A61K 39/0011* (2013.01); *A61K 2035/124* (2013.01); *A61K 2039/5156* (2013.01); *A61K 2039/585* (2013.01); *C12N 2501/515* (2013.01); *C12N 2510/02* (2013.01); *C12N 2511/00* (2013.01)

(58) Field of Classification Search
None
See application file for complete search history.

(56) References Cited

U.S. PATENT DOCUMENTS

| | | | |
|---|---|---|---|
| 5,415,874 A | 5/1995 | Bender et al. | |
| 5,552,300 A | 9/1996 | Makrides et al. | |
| 5,667,967 A | 9/1997 | Steinman et al. | |
| 5,686,281 A | 11/1997 | Roberts | |
| 5,830,755 A | 11/1998 | Nishimura et al. | |
| 5,851,828 A | 12/1998 | Seed et al. | |
| 6,103,521 A | 8/2000 | Capon et al. | |
| 6,133,433 A | 10/2000 | Hema et al. | |
| 6,190,656 B1 | 2/2001 | Clifford et al. | |
| 6,242,567 B1 | 6/2001 | Hema et al. | |
| 6,284,240 B1 | 9/2001 | Seed et al. | |
| 6,407,221 B1 | 6/2002 | Capon et al. | |
| 6,410,319 B1 | 6/2002 | Raubitschek et al. | |
| 6,464,978 B1 | 10/2002 | Brostoff et al. | |
| 6,753,162 B1 | 6/2004 | Seed et al. | |
| 6,770,749 B2 | 8/2004 | Ellenhorn et al. | |
| 6,984,382 B1 | 1/2006 | Groner et al. | |
| 7,049,136 B2 | 5/2006 | Seed et al. | |
| 7,052,906 B1 | 5/2006 | Lawson et al. | |
| 7,070,995 B2 | 7/2006 | Jensen | |
| 7,094,599 B2 | 8/2006 | Seed et al. | |
| 7,435,596 B2 | 10/2008 | Campana et al. | |
| 7,446,179 B2 | 11/2008 | Jensen et al. | |
| 7,446,190 B2 | 11/2008 | Sadelain et al. | |
| 7,456,263 B2 | 11/2008 | Sherman et al. | |
| 7,514,537 B2 | 4/2009 | Jensen | |
| 7,569,357 B2 | 8/2009 | Kranz et al. | |
| 7,608,410 B2 | 10/2009 | Dunn et al. | |
| 7,618,817 B2 | 11/2009 | Campbell | |
| 7,655,461 B2 | 2/2010 | Finn et al. | |
| 7,763,243 B2 | 7/2010 | Lum et al. | |
| 7,820,174 B2 | 10/2010 | Wang et al. | |
| 7,994,298 B2 | 8/2011 | Zhang et al. | |
| 8,026,097 B2 | 9/2011 | Campana et al. | |
| 8,252,914 B2 | 8/2012 | Zhang et al. | |

(Continued)

FOREIGN PATENT DOCUMENTS

| | | |
|---|---|---|
| DE | 4408999 | 9/1995 |
| DE | 19540515 | 6/1997 |

(Continued)

OTHER PUBLICATIONS

Maher, J. and E.T. Davies. 2004. Br. J. Cancer 91:817-821. (Year: 2004).*
Zhang, T. et al. 2005. Blood 106:1544-1551. (Year: 2005).*
Declaration of Dr. Mark Daniels submitted Nov. 22, 2016 in conjunction with related re-examination U.S. Appl. No. 90/013,688, pp. 24-68. (Year: 2016).*
Ardouin L, et al. "Crippling of CD3-zeta ITAMs does not impair T cell receptor signaling," Immunity. Apr. 1999;10(4):409-20.
Lipowska-Bhalla G, et al. "Targeted immunotherapy of cancer with CAR T cells: achievements and challenges," Cancer Immunol Immunother. Jul. 2012;61(7):953-62.

(Continued)

*Primary Examiner* — Zachary S Skelding
(74) *Attorney, Agent, or Firm* — Robin L. Teskin; Baker, Donelson, Bearman, Caldwell & Berkowitz, PC

(57) ABSTRACT

The invention is directed to modified T cells, methods of making and using isolated, modified T cells, and methods of using these isolated, modified T cells to address diseases and disorders. In one embodiment, this invention broadly relates to TCR-deficient T cells, isolated populations thereof, and compositions comprising the same. In another embodiment of the invention, these TCR-deficient T cells are designed to express a functional non-TCR receptor. The invention also pertains to methods of making said TCR-deficient T cells, and methods of reducing or ameliorating, or preventing or treating, diseases and disorders using said TCR-deficient T cells, populations thereof, or compositions comprising the same.

21 Claims, 1 Drawing Sheet
Specification includes a Sequence Listing.

(56) References Cited

U.S. PATENT DOCUMENTS

| | | | |
|---|---|---|---|
| 8,283,446 | B2 | 10/2012 | Jakobsen et al. |
| 8,399,645 | B2 | 3/2013 | Campana et al. |
| 8,465,743 | B2 | 6/2013 | Rosenberg et al. |
| 8,519,100 | B2 | 8/2013 | Jakobsen et al. |
| 8,835,617 | B2 | 9/2014 | Luban et al. |
| 8,945,868 | B2 | 2/2015 | Collingwood et al. |
| 8,956,828 | B2 | 2/2015 | Bonini et al. |
| 9,051,391 | B2 | 6/2015 | Mineno et al. |
| 9,663,763 | B2 * | 5/2017 | Sentman ............... C12N 5/0636 |
| 9,821,011 | B1 * | 11/2017 | Sentman ............... C12N 5/0636 |
| 2001/0007152 | A1 | 7/2001 | Sherman et al. |
| 2002/0045241 | A1 | 4/2002 | Schendel |
| 2002/0137697 | A1 | 9/2002 | Eshhar et al. |
| 2003/0060444 | A1 | 3/2003 | Finney et al. |
| 2003/0077249 | A1 | 4/2003 | Bebbington et al. |
| 2003/0082719 | A1 | 5/2003 | Schumacher et al. |
| 2003/0093818 | A1 | 5/2003 | Belmont et al. |
| 2003/0219463 | A1 | 11/2003 | Falkenburg et al. |
| 2004/0038886 | A1 | 2/2004 | Finney et al. |
| 2004/0115198 | A1 | 6/2004 | Spies et al. |
| 2004/0259196 | A1 | 12/2004 | Zipori et al. |
| 2005/0048055 | A1 | 3/2005 | Newell et al. |
| 2005/0113564 | A1 | 5/2005 | Campana et al. |
| 2005/0129671 | A1 | 6/2005 | Cooper et al. |
| 2005/0238626 | A1 | 10/2005 | Yang et al. |
| 2006/0247420 | A1 | 2/2006 | Coukos et al. |
| 2006/0093605 | A1 | 5/2006 | Campana et al. |
| 2006/0166314 | A1 | 7/2006 | Voss et al. |
| 2006/0263334 | A1 | 11/2006 | Finn et al. |
| 2006/0269529 | A1 | 11/2006 | Niederman et al. |
| 2007/0066802 | A1 | 3/2007 | Geiger |
| 2007/0077241 | A1 | 4/2007 | Spies et al. |
| 2007/0116690 | A1 | 5/2007 | Yang et al. |
| 2008/0199424 | A1 | 8/2008 | Yang et al. |
| 2008/0292549 | A1 | 11/2008 | Jakobsen et al. |
| 2008/0292602 | A1 | 11/2008 | Jakobsen et al. |
| 2008/0153029 | A1 | 12/2008 | Mineno et al. |
| 2009/0053184 | A1 | 2/2009 | Morgan et al. |
| 2009/0202501 | A1 | 8/2009 | Zhang et al. |
| 2009/0226404 | A1 | 9/2009 | Schuler et al. |
| 2009/0304657 | A1 | 12/2009 | Morgan et al. |
| 2009/0324566 | A1 | 12/2009 | Shiku et al. |
| 2010/0009863 | A1 | 1/2010 | Himmler et al. |
| 2010/0015113 | A1 | 1/2010 | Restifo et al. |
| 2010/0029749 | A1 | 2/2010 | Zhang et al. |
| 2010/0055117 | A1 | 3/2010 | Krackhardt et al. |
| 2010/0104556 | A1 | 4/2010 | Blankenstein et al. |
| 2010/0105136 | A1 | 4/2010 | Carter et al. |
| 2010/0135974 | A1 | 6/2010 | Eshhar et al. |
| 2010/0143315 | A1 | 6/2010 | Voss et al. |
| 2010/0178276 | A1 | 7/2010 | Sadelain et al. |
| 2010/0189728 | A1 | 7/2010 | Schendel et al. |
| 2010/0273213 | A1 | 10/2010 | Mineno et al. |
| 2011/0158957 | A1 | 6/2011 | Bonini et al. |
| 2011/0213288 | A1 | 9/2011 | Choi et al. |
| 2012/0015434 | A1 | 1/2012 | Campana et al. |
| 2012/0252742 | A1 | 10/2012 | Kranz et al. |
| 2012/0294857 | A1 | 11/2012 | Sentman et al. |
| 2012/0302466 | A1 | 11/2012 | Sentman et al. |
| 2013/0011375 | A1 | 1/2013 | Chen |
| 2013/0216509 | A1 | 8/2013 | Campana et al. |
| 2013/0266551 | A1 | 10/2013 | Campana et al. |
| 2013/0323214 | A1 | 12/2013 | Gottschalk et al. |
| 2014/0004132 | A1 | 1/2014 | Brenner et al. |
| 2014/0148354 | A1 | 5/2014 | Campana et al. |
| 2014/0328812 | A1 | 11/2014 | Campana et al. |
| 2015/0139943 | A1 | 5/2015 | Campana et al. |
| 2016/0194375 | A1 | 7/2016 | Kitchen et al. |

FOREIGN PATENT DOCUMENTS

| | | |
|---|---|---|
| DE | 10259713 | 8/2004 |
| EP | 0340793 | 8/1995 |
| EP | 0499555 | 5/2000 |
| EP | 0574512 | 5/2003 |
| EP | 1226244 | 7/2004 |
| EP | 0871495 | 6/2005 |
| EP | 1075517 | 7/2006 |
| EP | 1932537 | 6/2008 |
| EP | 1765860 | 10/2008 |
| EP | 2186825 | 5/2010 |
| EP | 1791865 | 7/2010 |
| JP | H05176760 | 7/1993 |
| JP | 11-243955 | 9/1999 |
| JP | 2008-523783 | 7/2008 |
| JP | 2011-512786 | 4/2011 |
| WO | WO 1991018019 | 11/1991 |
| WO | WO 1992015322 | 9/1992 |
| WO | WO 1994024282 | 10/1994 |
| WO | WO 1996015238 | 5/1996 |
| WO | WO 1996013584 | 9/1996 |
| WO | WO 1998018809 | 7/1998 |
| WO | WO 1998041613 | 9/1998 |
| WO | WO 2000031239 | 2/2000 |
| WO | WO 2000014257 | 3/2000 |
| WO | WO 2001092291 | 6/2001 |
| WO | WO 2004056845 | 8/2004 |
| WO | 2005044996 | 5/2005 |
| WO | 2006036445 | 4/2006 |
| WO | WO 2006103429 | 5/2006 |
| WO | WO 2006060878 | 6/2006 |
| WO | 2008153029 | 12/2008 |
| WO | WO 2009059804 | 5/2009 |
| WO | WO 2009091826 | 7/2009 |
| WO | WO 2010012829 | 4/2010 |
| WO | WO 2010025177 | 4/2010 |
| WO | WO 2010058023 | 5/2010 |
| WO | WO 2010088160 | 5/2010 |
| WO | WO 2010037395 | 8/2010 |
| WO | WO 2010107400 | 9/2010 |
| WO | WO 2011059836 | 5/2011 |
| WO | 2011/070443 | 6/2011 |
| WO | WO 2012050374 | 4/2012 |
| WO | WO 2013166051 | 11/2013 |

OTHER PUBLICATIONS

Shores EW, et al. "Role of TCR zeta chain in T cell development and selection," Science. Nov. 11, 1994;266(5187):1047-50.

Shores EW, et al. "Role of the multiple T cell receptor (TCR)-zeta chain signaling motifs in selection of the T cell repertoire," J Exp Med. Mar. 3, 1997;185(5):893-900.

Bohne F. Specific elimination of hepatitis B virus-infected hepatocytes by modified human T cells expressing a chimeric T cell receptor and establishing a cytotoxic immune response. (Thesis.) University of Cologne; 2006.

Bolhuis RLH, Hoogenboom HR, Gratama JW. Targeting of peripheral blood T lymphocytes. Springer Semin Immunopathol. 1996;18(2):211-26.

Bridges SH. Immune reconstitution for HIV disease. Antibiot Chemother. 1996;48:233-9.

Brocker T, Karjalainen K. Adoptive tumor immunity mediated by lymphocytes bearing modified antigen-specific receptors. Adv Immunol. 1998;68:257-69.

Bucala R, Metz CN. Immunosuppressive factors in cancer. In: Stuhler G, Walden P, editors. Cancer Immune Therapy. Weinheim, Germany: Wiley-VCH Verlag GmbH & Co; 2002. p. 119-54.

Bullain SS, Sahin A, Szentirmai O, Sanchez C, Lin N, Baratta E, et al. Genetically engineered T cells to target EGFRvIII expressing glioblastoma. J Neurooncol. 2009;94(3):373-82.

Buschle M, Campana D, Carding SR, Richard C, Hoffbrand AV, Brenner MK. Interferon gamma Inhibits Apoptotic Cell Death in B Cell Chronic Lymphocytic Leukemia. Journal of Experimental Medicine. Jan. 1993;177:213-18.

Calogero A, de Leij LFMH, Mulder NH, Hospers GAP. Recombinant T-cell receptors: an immunologic link to cancer therapy. J Immunother. 2000;23(4):393-400.

Campana D, Coustan-Smith E, Janossy G. The immunologic detection of minimal residual disease in acute leukemia. Blood. Jul. 1990;76(1):163-71.

(56) References Cited

OTHER PUBLICATIONS

Campana D, Janossy G, Bofill M, Trejdosiewicz LK, Ma D, Hoffbrand AV, Mason DY, Lebacq AM, Forster HK. Human B cell development. I. Phenotypic differences of B lymphocytes in the bone marrow and peripheral lymphoid tissue. The Journal of Immunology. Mar. 1, 1985;134(3):1524-30.

Campana D, Janossy G. Leukemia diagnosis and testing of complement-fixing antibodies for bone marrow purging in acute lymphoid leukemia. Blood. Dec. 1, 1986;68(6):1264-71.

Campana D, Schwarz H, Imai C. 4-1BB chimeric antigen receptors. The Cancer Journal. Mar. 1, 2014;20(2):134-40.

Campana D. Chimeric antigen receptor technology: a breakthrough in immuno-oncology. Medicographia. 2015;37:280-6.

Campana D. Making Headway. Asia-Pacific Biotech News. Jun. 2008;12(8):20-3.

Campana DA, Janossy GE, Coustan-Smith EL, Amlot PL, Tian WT, Ip ST, Wong LE. The expression of T cell receptor-associated proteins during T cell ontogeny in man. The Journal of Immunology. Jan. 1, 1989;142(1):57-66.

Cartellieri M, Bachmann MP, Feldmann A, Bippes C, Stamova S, Wehner R, et al. Chimeric Antigen Receptor-Engineered T cells for Immunotherapy of cancer. J Biomed Biotechnol. 2010;2010:1-13.

Cartellieri M, Koristka S, Arndt C, Feldmann A, Stamova S, von Bonin M, et al. A novel Ex Vivo isolation and expansion procedure for chimeric antigen receptor engrafted human T cells. PLoS One. 2014;9(4):e93745.

Cebecauer M, Guillaume P, Mark S, Michielin O, Boucheron N, Bezard M, Meyer BH, Segura JM, Vogel H, Luescher IF. CD8+ cytotoxic T lymphocyte activation by soluble major histocompatibility complex-peptide dimers. Journal of Biological Chemistry. Jun. 24, 2005;280(25):23820-8.

Chamorro LMT. Adverse immune response in previously untreated patients infected with the human immunodeficiency virus initiating highly active antiretroviral therapy (HAART): prevalence factors, predictors, and clinical evolution. (Thesis.) Complutense University of Madrid School of Medicine; 2010.

Chang YH, Campana D. Increasing the antineoplastic potential of natural killer cells with a chimeric receptor activated by NKG2D ligands. OncoImmunology. Jul. 1, 2013;2(7):e24899.

Chang YH, Connolly J, Shimasaki N, Mimura K, Kono K, Campana D. A chimeric receptor with NKG2D specificity enhances natural killer cell activation and killing of tumor cells. Cancer research. Mar. 15, 2013;73(6):1777-86.

Chen Z, Kolokoltsov AA, Wang J, Adhikary S, Lorinczi M, Elferink LA, et al. GRB2 interaction with the ecotropic murine leukemia virus receptor, mCAT-1, controls virus entry and is stimulated by virus binding. J Virol. 2012;86(3):1421-32.

Cheng M, Zhang J, Jiang W, Chen Y, Tian Z. Natural killer cell lines in tumor immunotherapy. Front Med. 2012;6(1):56-66.

Cheok MH, Ding C, Yang W, Das S, Campana D, Cheng C, Cook EH, Pui CH, Relling MV, Evans WE. Genetic Polymorphisms in the Promoter Region of the beta-2 Adrenergic Receptor Are Associated with the Early Response of Acute Lymphoblastic Leukemia to Chemotherapy. Blood. Nov. 16, 2004;104(11):1959.

Cho D, Shook DR, Shimasaki N, Chang YH, Fujisaki H, Campana D. Cytotoxicity of activated natural killer cells against pediatric solid tumors. Clinical Cancer Research. Aug. 1, 2010;16(15):3901-9.

Conley ME, Larche M, Bonagura VR, Lawton 3rd AR, Buckley RH, Fu SM, Coustan-Smith E, Herrod HG, Campana D. Hyper IgM syndrome associated with defective CD40-mediated B cell activation. Journal of Clinical Investigation. Oct. 1994;94(4):1404.

Cooper LJN, Kalos M, Lewinsohn DA, Riddell SR, Greenberg PD. Transfer of specificity for human immunodeficiency virus type 1 into primary human T lymphocytes by introduction of T-cell receptor genes. J Virol. 2000;74(17):8207-12.

Costa GL, Benson JM, Seroogy CM, Achacoso P, Fathman CG, Nolan GP. Targeting rare populations of murine antigen-specific T lymphocytes by retroviral transduction for potential application in gene therapy for autoimmune disease. J Immunol. 2000;164(7):3581-90.

Coustan-Smith E, Kitanaka A, Pui CH, McNinch L, Evans WE, Raimondi SC, Behm FG, Arico M, Campana D. Clinical relevance of BCL-2 overexpression in childhood acute lymphoblastic leukemia. Blood. Feb. 1, 1996;87(3):1140-6.

Coustan-Smith E, Sancho J, Hancock ML, Razzouk BI, Ribeiro RC, Rivera GK, Rubnitz JE, Sandlund JT, Pui CH, Campana D. Use of peripheral blood instead of bone marrow to monitor residual disease in children with acute lymphoblastic leukemia. Blood. Oct. 1, 2002;100(7):2399-402.

Coustan-Smith E, Sandlund JT, Perkins SL, Chen H, Chang M, Abromowitch M, Campana D. Minimal disseminated disease in childhood T-cell lymphoblastic lymphoma: a report from the children's oncology group. Journal of Clinical Oncology. Jul. 20, 2009;27(21):3533-9.

Daly T, Royal RE, Kershaw MH, Treisman J, Wang G, Li W, et al. Recognition of human colon cancer by T cells transduced with a chimeric receptor gene. Cancer Gene Ther. 2000;7(2):284-91.

Darcy PK, Haynes NM, Snook MB, Trapani JA, Cerruti L, Jane SM, et al. Redirected perforin-dependent lysis of colon carcinoma by ex vivo genetically engineered CTL. J Immunol. 2000;164(7):3705-12.

Davies DM, Maher J. Adoptive T-cell immunotherapy of cancer using chimeric antigen receptor-grafted T Cells. Arch Immunol Ther Exp. 2010;58:165-78.

Deeks SG, Wagner B, Anton P a, Mitsuyasu RT, Scadden DT, Huang C, et al. A phase II randomized study of HIV-specific T-cell gene therapy in subjects with undetectable plasma viremia on combination antiretroviral therapy. Mol Ther. 2002;5(6):788-97.

Dey B, Berger EA. Towards an HIV cure based on targeted killing of infected cells. Curr Opin HIV AIDS. 2015;10(3):207-13.

Didigu C, Doms R. Gene Therapy Targeting HIV Entry. Viruses. 2014;6(3):1395-409.

Didigu CA. Therapeutic applications and specificity of action of designer nucleases for precision genome engineering. (Thesis.) University of Pennsylvania; 2015.

Dorfman JR, Germain RN. MHC-dependent survival of naive T cells? A complicated answer to a simple question. Microbes and Infection. Apr. 30, 2002;4(5):547-54.

Dropulic B, Jun. CH. Gene-based immunotherapy for human immunodeficiency virus infection and acquired immunodeficiency syndrome. Hum Gene Ther. 2006;17(6):577-88.

Dunbar CE. Blood's 70th anniversary: CARs on the Blood highway. Blood. 2016;128(1):21-4.

Egerer L, von Laer D, Kimpel J. Gene therapy for HIV-1 infection. In: Tang Y-W, editor. Recent Translational Research in HIV/AIDS. InTech; 2011. p. 431-56.

Ernst B, Lee DS, Chang JM, Sprent J, Surh CD. The peptide ligands mediating positive selection in the thymus control T cell survival and homeostatic proliferation in the periphery. Immunity. Aug. 1, 1999;11(2):173-81.

Farson D, McGuinness RP, Dull TJ, Limoli K, Lazar R, Jalali S, et al. Large-scale manufacturing of safe and efficient retrovirus packaging lines for use in immunotherapy protocols. J Gene Med. 1999;1(3):195-209.

Farson D, Witt R, McGuinness RP, Dull TJ, Kelly M, Song J, et al. A New-Generation Stable Inducible Packaging Cell Line for Lentiviral Vectors. Hum Gene Ther. 2001;12:981-97.

Finney HM, Akbar An, Lawson ADG. Activation of Resting Human Primary T Cells with Chimeric Receptors: Costimulation from CD28, Inducible Costimulator, CD134, and CD137 in Series with Signals from the TCR Chain. J Immunol. 2004;172(1):104-13.

Fitzer-Attas CJ, Eshhar Z. Tyrosine kinase chimeras for antigen-selective T-body therapy. Adv Drug Deliv Rev. 1998;31(1-2):171-82.

Froelich CJ, Dixit VM, Yang X. Lymphocyte granule-mediated apoptosis: Matters of viral mimicry and deadly proteases. Immunol Today. 1998;19(1):30-6.

Fujisaki H, Kakuda H, Imai C, Campana D. Sustained Expansion of Human Natural Killer Cells for Leukemia Therapy. Blood. Nov. 16, 2006;108(11):3719.

(56) References Cited

OTHER PUBLICATIONS

Fujisaki H, Kakuda H, Imai C, Mullighan CG, Campana D. Replicative potential of human natural killer cells. British journal of haematology. Jun. 1, 2009;145(5):606-13.
Alajez NM 'MHC-Unrestricted MUC1-Specific T Cell Receptor for Cancer Immunotherapy/Gene Therapy' (2003) MHC-Unrestricted MUC1-Specific T Cell Receptor for Cancer Immunotherapy/Gene Therapy.Doctoral Dissertation, University of Pittsburgh.
Alajez NM, et al. 'Therapeutic potential of a tumor-specific, MHC-unrestricted T-cell receptor expressed on effector cells of theinnate and the adaptive immune system through bone marrow transduction and immune reconstitution.' Blood. Jun. 15, 2005;105(12):4583-9. Epub Mar. 3, 2005.
Alli R, et al. 'Retrogenic Modeling of Experimental Allergic Encephalomyelitis Associates T Cell Frequency but Not TCR Functional Affinity with Pathogenicity' J Immunol. Jul. 1, 2008;181(1):136-45.
Almåsbak H, et al. 'Non-MHC-dependent redirected T cells against tumor cells.' Methods Mol Biol. 2010;629:453-93. doi: 10.1007/978-1-60761-657-3_28.
Beecham EJ, et al. 'Dynamics of tumor cell killing by human T lymphocytes armed with an anti-carcinoembryonic antigen chimeric immunoglobulin T-cell receptor.' J Immunother. May-Jun 2000;23(3):332-43.
Bell LM, et al. 'Cytoplasmic tail deletion of T cell receptor (TCR) beta-chain results in its surface expression as glycosylphosphatidylinositol-anchored polypeptide on mature T cells in the absence of TCR-alpha.' J Biol Chem. Sep. 9, 1994;269(36):22758-63.
Berry LJ, et al. 'Adoptive immunotherapy for cancer: the next generation of gene-engineered immune cells.' Tissue Antigens. Oct. 2009;74(4):277-89. doi: 10.1111/j.1399-0039.2009.01336.x.
Bialer G, et al. 'Selected murine residues endow human TCR with enhanced tumor recognition' J Immunol. Jun. 1, 2010;184(11):6232-41. doi: 10.4049/jimmunol.0902047. Epub Apr. 28, 2010.
Billadeau DD, et al. 'NKG2D-DAP10 triggers human NK cell-mediated killing via a Syk-independent regulatory pathway.' Nat Immunol. Jun. 2003;4(6):557-64. Epub May 11, 2003.
Bridgeman JS, et al. 'The optimal antigen response of chimeric antigen receptors harboring the CD3zeta transmembrane domain is dependent upon incorporation of the receptor into the endogenous TCR/CD3 complex.' J Immunol. Jun. 15, 2010;184(12):6938-49. doi: 10.4049/jimmunol.0901766. Epub May 17, 2010.
Chmielewski M, et al. 'CD28 cosignalling does not affect the activation threshold in a chimeric antigen receptor-redirected T-cell attack.' Gene Ther. Jan. 2011;18(1):62-72. doi: 10.1038/gt.2010.127. Epub Oct. 14, 2010.
Cohen CJ, et al. 'Enhanced Antitumor Activity of Murine-Human Hybrid T-Cell Receptor (TCR) in Human Lymphocytes Is Associated with Improved Pairing and TCR/CD3 Stability' Cancer Res. Sep. 1, 2006;66(17):8878-86.
Cooper LJ, et al. 'Manufacturing of gene-modified cytotoxic T lymphocytes for autologous cellular therapy for lymphoma.' Cytotherapy. 2006;8(2):105-17.
Dall P, et al. 'In vivo cervical cancer growth inhibition by genetically engineered cytotoxic T cell' Cancer Immunol Immunother. Jan. 2005;54(1):51-60.
Danielian S, et al. 'Both T cell receptor (TcR)-CD3 complex and CD2 increase the tyrosine kinase activity of p56lck. CD2 can mediate TcR-CD3-independent and CD45-dependent activation of p56lck.' Eur J Immunol. Nov. 1992;22(11):2915-21.
Donnadieu et al., 'Reconstitution of CD3 zeta coupling to calcium mobilization via genetic complementation.' J Biol. Chem. 269:32828-34 (1994).
Dennehy KM, et al. 'Mitogenic CD28 Signals Require the Exchange Factor Vav1 to Enhance TCR Signaling at the SLP-76-Vav-Itk Signalosome' J Immunol. Feb. 1, 2007;178(3):1363-71.
D'Oro U, et al. 'Regulation of constitutive TCR internalization by the zeta-chain.' J Immunol. Dec. 1, 2002;169(11):6269-78.

Duplay P, et al. 'An activated epidermal growth factor receptor/Lck chimera restores early T cell receptor-mediated calcium response in a CD45-deficient T cell line.' J Biol Chem. Jul. 26, 1996;271(30):17896-902.
Eshhar Z, et al. 'Specific activation and targeting of cytotoxic lymphocytes through chimeric single chains consisting of antibody-binding domains and the gamma or zeta subunits of the immunoglobulin and T-cell receptors.' Proc Natl Acad Sci U S A. Jan. 15, 1993;90(2):720-4.
Favier B, et al. 'TCR dynamics on the surface of living T cells' Int Immunol. Dec. 2001;13(12):1525-32.
Finney HM, et al. 'Chimeric receptors providing both primary and costimulatory signaling in T cells from a single gene product.' J Immunol. Sep. 15, 1998;161(6):2791-7.
Frankel TL, et al. 'Both CD4 and CD8 T Cells Mediate Equally Effective In Vivo Tumor Treatment When Engineered with a Highly Avid TCR Targeting Tyrosinase' J Immunol. Jun. 1, 2010;184(11):5988-98. doi:10.4049/jimmunol.1000189. Epub Apr. 28, 2010.
Fujihashi K, et al. 'gamma/delta T cell-deficient mice have impaired mucosal immunoglobulin A response' J Exp Med. Apr. 1, 1996;183(4):1929-35.
Garrity D, et al. 'The activating NKG2D receptor assembles in the membrane with two signaling dimers into a hexameric structure.' Proc Natl Acad Sci U S A. May 24, 2005;102(21):7641-6. Epub May 13, 2005.
Geiger TL, et al. 'The TCR zeta-chain immunoreceptor tyrosine-based activation motifs are sufficient for the activation and differentiation of primary T lymphocytes.' J Immunol. May 15, 1999;162(10):5931-9.
Geiger TL, et al. 'Integrated src kinase and costimulatory activity enhances signal transduction through single-chain chimeric receptors in T lymphocytes' Blood. Oct. 15, 2001;98(8):2364-71.
Gouaillard C, et al. 'Evolution of T cell receptor (TCR) α β heterodimer assembly with the CD3 complex' Eur J Immunol. Dec. 2001;31(12):3798-805.
Hawkins RE, et al. 'Development of adoptive cell therapy for cancer: a clinical perspective.' Hum Gene Ther. Jun. 2010;21(6):665-72. doi: 10.1089/hum.2010.086.
Haynes NM, et al. 'Redirecting Mouse CTL Against Colon Carcinoma: Superior Signaling Efficacy of Single-Chain Variable Domain Chimeras Containing TCR-ζ vs FcεRI-γ' J Immunol. Jan. 1, 2001;166(1):182-7.
Horng T, et al. 'NKG2D signaling is coupled to the interleukin 15 receptor signaling pathway.' Nat Immunol. Dec. 2007;8(12):1345-52. Epub Oct. 21, 2007.
Imai C, et al. 'Chimeric receptors with 4-1BB signaling capacity provoke potent cytotoxicity against acute lymphoblastic leukemia.' Leukemia. Apr. 2004;18(4):676-84.
Irles C, et al. 'CD45 ectodomain controls interaction with GEMs and Lck activity for optimal TCR signaling.' Nat Immunol. Feb. 2003;4(2):189-97. Epub Dec. 23, 2002.
Itohara S, et al. 'T cell receptor delta gene mutant mice: independent generation of alpha beta T cells and programmed rearrangements of gamma delta TCR genes.' Cell. Feb. 12, 1993;72(3):337-48.
Joyce DE, et al. 'Functional interactions between the thrombin receptor and the T-cell antigen receptor in human T-cell lines' Blood. Sep. 1, 1997;90(5):1893-901.
Kieback E, et al. 'Enhanced T cell receptor gene therapy for cancer.' Expert Opin Biol Ther. May 2010;10(5):749-62. doi: 10.1517/14712591003689998.
Kieback E, et al. 'A safeguard eliminates T cell receptor gene-modified autoreactive T cells after adoptive transfer' Proc Natl Acad Sci U S A. Jan. 15, 2008;105(2):623-8. doi: 10.1073/pnas.0710198105. Epub Jan. 8, 2008.
Kreiβ et al., 'Contrasting contributions of complementarity-determining region 2 and hypervariable region 4 of rat BV8S2+ (Vbeta8.2) TCR to the recognition of myelin basic protein and different types of bacterial superantigens.' Int Immunol. 16(5):655-663 (2004).
Koya RC, et al. 'Kinetic phases of distribution and tumor targeting by T cell receptor engineered lymphocytes inducing robust antitu-

(56) References Cited

OTHER PUBLICATIONS mor responses.' Proc Natl Acad Sci U S A. Aug. 10, 2010;107(32):14286-91. doi: 10.1073/pnas.1008300107. Epub Jul. 12, 2010.

Leisegang M, et al. 'T-Cell Receptor Gene-Modified T Cells with Shared Renal Cell Carcinoma Specificity for Adoptive T-Cell Therapy' Clin Cancer Res. Apr. 15, 2010;16(8):2333-43. doi: 10.1158/1078-0432.CCR-09-2897. Epub Apr. 6, 2010.

Liang X, et al. 'A Single TCRα-Chain with Dominant Peptide Recognition in the Allorestricted HER2/neu-Specific T Cell Repertoire' J Immunol. Feb. 1, 2010;184(3):1617-29. doi: 10.4049/jimmunol.0902155. Epub Dec. 30, 2009.

Lin WY, et al. 'Developmental dissociation of T cells from B, NK, and myeloid cells revealed by MHC class II-specific chimeric immune receptors bearing TCR-zeta or FcR-gamma chain signaling domains.' Blood. Oct. 15, 2002;100(8):3045-8.

Losch FO, et al. 'Activation of T cells via tumor antigen specific chimeric receptors: the role of the intracellular signaling domain.' Int J Cancer. Jan. 20, 2003;103(3):399-407.

Maher J, et al. 'Human T-lymphocyte cytotoxicity and proliferation directed by a single chimeric TCRzeta /CD28 receptor.' Nat Biotechnol. Jan. 2002;20(1):70-5.

Mallevaey T, et al. 'T Cell Receptor CDR2b and CDR3b Loops Collaborate Functionally to Shape the iNKT Cell Repertoire' Immunity. Jul. 17, 2009;31(1):60-71. doi: 10.1016/j.immuni.2009.05.010.

Marie-Cardine A, et al. 'SHP2-interacting Transmembrane Adaptor Protein (SIT), A Novel Disulfide-linked Dimer Regulating Human T Cell Activation' J Exp Med. Apr. 19, 1999;189(8):1181-94.

McFarland HI, et al. 'Signaling through MHC in transgenic mice generates a population of memory phenotype cytolytic cells that lack TCR.' Blood. Jun. 1, 2003;101(11):4520-8. Epub Feb. 13, 2003.

Mekala DJ, et al. 'IL-10-dependent suppression of experimental allergic encephalomyelitis by Th2-differentiated, anti-TCRredirected T lymphocytes.' J Immunol. Mar. 15, 2005;174(6):3789-97.

Meresse B, et al. 'Coordinated induction by IL15 of a TCR-independent NKG2D signaling pathway converts CTL into lymphokine-activated killer cells in celiac disease.' Immunity. Sep. 2004;21(3):357-66.

Milone MC, et al. 'Chimeric receptors containing CD137 signal transduction domains mediate enhanced survival of T cells and increased antileukemic efficacy in vivo.' Mol Ther. Aug. 2009;17(8):1453-64. doi: 10.1038/mt.2009.83. Epub Apr. 21, 2009.

Mizoguchi A, et al. 'Role of appendix in the development of inflammatory bowel disease in TCR-alpha mutant mice.' J Exp Med. Aug. 1, 1996;184(2):707-15.

Moeller M, et al. 'A functional role for CD28 costimulation in tumor recognition by single-chain receptor-modified T cells.' Cancer Gene Ther. May 2004;11(5):371-9.

Moisini I, et al. 'Redirecting Therapeutic T Cells against Myelin-Specific T Lymphocytes Using a Humanized Myelin Basic Protein-HLA-DR2-ζ Chimeric Receptor' J Immunol. Mar. 1, 2008;180(5):3601-11.

Mombaerts P, et al. 'Mutations in T-cell antigen receptor genes alpha and beta block thymocyte development at different stages.' Nature. Nov. 19, 1992;360(6401):225-31.

Motmans K, et al. 'Enhancing the tumor-specifity of human T cells by the expression of chimericimmunoglobulin/T cell receptor genes.' Immunotechnology, Nov. 1996;2(4): 303-304(2).

Nguyen P, et al. 'Antigen-specific targeting of CD8+ T cells with receptor-modified T lymphocytes.' Gene Ther. Apr. 2003;10(7):594-604.

Nguyen P, et al. 'Discrete TCR repertoires and CDR3 features distinguish effector and Foxp3+ regulatory T lymphocytes in myelin oligodendrocyte glycoprotein-induced experimental allergic encephalomyelitis.' J Immunol. Oct. 1, 2010;185(7):3895-904. doi: 10.4049/jimmunol.1001550. Epub. Sep. 1, 2010.

Okamoto et al., 'Improved expression and reactivity of transduced tumor-specific TCRs in human lymphocytes by specific silencing of endogenous TCR.' Cancer Res 69:9003-11 (2009).

Nguyen P, et al. 'Identification of a murine CD28 dileucine motif that suppresses single-chain chimeric T-cell receptor expression and function.' Blood. Dec. 15, 2003;102(13):4320-5. Epub Aug. 28, 2003.

Polic B, et al. 'How alpha beta T cells deal with induced TCR alpha ablation.' Proc Natl Acad Sci U S A. Jul. 17, 2001;98(15):8744-9. Epub Jul. 10, 2001.

Qian D, et al. 'Dominant-negative zeta-associated protein 70 inhibits T cell antigen receptor signaling.' J Exp Med. Feb. 1, 1996;183(2):611-20.

Rivera A, et al. 'Host stem cells can selectively reconstitute missing lymphoid lineages in irradiation bone marrow chimeras.' Blood. Jun. 1, 2003;101(11):4347-54. Epub Feb. 13, 2003.

Rossig C, et al. 'Targeting of G(D2)-positive tumor cells by human T lymphocytes engineered to express chimeric T-cell receptor genes' Int J Cancer. Oct. 15, 2001;94(2):228-36.

Sadelain M. 'T-cell engineering for cancer immunotherapy.' Cancer J. Nov.-Dec. 2009;15(6):451-5. doi: 10.1097/PPO.0b013e3181c51f37.

Schirrmann T, et al. 'Human natural killer cell line modified with a chimeric immunoglobulin T-cell receptor gene leads to tumor growth inhibition in vivo' Cancer Gene Ther. Apr. 2002;9(4):390-8.

Schmitt TM, et al. 'T cell receptor gene therapy for cancer.' Hum Gene Ther. Nov. 2009;20(11):1240-8. doi: 10.1089/hum.2009.146.

Sommermeyer D, et al. 'Designer T cells by T cell receptor replacement' Eur J Immunol. Nov. 2006;36(11):3052-9.

Spaapen R 'Rebuilding human leukocyte antigen class II-restricted.' Novel strategies for identification and therapeutic application of minor histocompatibility antigens 13 (2009): 79.

Spaapen R, et al. 'Rebuilding Human Leukocyte Antigen Class II—Restricted Minor Histocompatibility Antigen Specificity in Recall Antigen-Specific T Cells by Adoptive T Cell Receptor Transfer: Implications for Adoptive Immunotherapy' Clin Cancer Res. Jul. 1, 2007;13(13):4009-15.

Sturmhöfel K, et al. 'Antigen-independent, integrin-mediated T cell activation.' J Immunol. Mar. 1, 1995;154(5):2104-11.

Sugita M, et al. 'Failure of Trafficking and Antigen Presentation by CD1 in AP-3-Deficient Cells' Immunity. May 2002;16(5):697-706.

Symes J, et al. 'Genetic Modification of T Lymphocytes for Cancer Therapy' Gene Therapy and Cancer Research Focus (2008): 163.

Udyavar A, et al. 'Rebalancing immune specificity and function in cancer by T-cell receptor gene therapy.' Arch Immunol Ther Exp (Warsz). Oct. 2010;58(5):335-46. doi: 10.1007/s00005-010-0090-1. Epub Aug. 1, 2010.

Udyavar A, et al. 'Subtle affinity-enhancing mutations in a myelin oligodendrocyte glycoprotein-specific TCR alter specificity and generate new self-reactivity' J Immunol. Apr. 1, 2009;182(7):4439-47. doi: 10.4049/jimmunol.0804377.

Verneris MR, et al. 'Role of NKG2D signaling in the cytotoxicity of activated and expanded CD8+ T cells.' Blood. Apr. 15, 2004;103(8):3065-72. Epub Nov. 20, 2003.

Voss RH, et al. 'Molecular design of the Cαβ interface favors specific pairing of introduced TCRαβ in human T cells' J Immunol. Jan. 1, 2008;180(1):391-401.

Wang J, et al. 'Optimizing adoptive polyclonal T cell immunotherapy of lymphomas, using a chimeric T cell receptor possessing CD28 and CD137 costimulatory domains.' Hum Gene Ther. Aug. 2007;18(8):712-25.

Weiss A, et al. 'Regulation of protein tyrosine kinase activation by the T-cell antigen receptor zeta chain.' Cold Spring Harb Symp Quant Biol. 1992;57:107-16.

Williams BL, et al. 'Genetic evidence for differential coupling of Syk family kinases to the T-cell receptor: reconstitution studies in a ZAP-70-deficient Jurkat T-cell line.' Mol Cell Biol. Mar. 1998;18(3):1388-99.

Wu J, et al. 'An activating immunoreceptor complex formed by NKG2D and DAP10.' Science. Jul. 30, 1999;285(5428):730-2.

Xu H, et al. 'A kinase-independent function of Lck in potentiating antigen-specific T cell activation.' Cell. Aug. 27, 1993;74(4):633-43.

(56) References Cited

OTHER PUBLICATIONS

Yachi PP, et al. 'Altered Peptide Ligands Induce Delayed CD8-T Cell Receptor Interaction—a Role for CD8 in Distinguishing Antigen Quality' Immunity. Aug. 2006;25(2):203-11. Epub Jul. 27, 2006.
Zhang T, et al. 'Generation of antitumor responses by genetic modification of primary human T cells with a chimeric NKG2D receptor.' Cancer Res. Jun. 1, 2006;66(11):5927-33.
Zhao Y, et al. 'A Herceptin-Based Chimeric Antigen Receptor with Modified Signaling Domains Leads to Enhanced Survival of Transduced T Lymphocytes and Antitumor Activity' J Immunol. Nov. 1, 2009;183(9):5563-74. doi: 10.4049/jimmunol.0900447.
Yu C, et al. 'Inhibitory signaling potential of a TCR-like molecule in lamprey.' Eur J Immunol. Feb. 2009;39(2):571-9. doi: 10.1002/eji.200838846.
Lustgarten J, et al. Specific elimination of IgE production using T cell lines expressing chimeric T cell receptor genes, Eur J Immunol. Oct. 1995;25(10):2985-91.
Surh CD, et al. "Homeostasis of memory T cells," Immunol Rev. Jun. 2006;211:154-63.
Schneider MA, et al. "CCR7 is required for the in vivo function of CD4+ CD25+ regulatory T cells," J Exp Med. Apr. 16, 2007;204(4):735-45.
Maloy KJ, et al. "Fueling regulation: IL-2 keeps CD4+ Treg cells fit," Nat Immunol. Nov. 2005;6(11):1071-2.
Call ME, et al. "Molecular mechanisms for the assembly of the T cell receptor-CD3 complex," Mol Immunol. Apr. 2004;40(18):1295-305.
Cooper TA. "Use of minigene systems to dissect alternative splicing elements," Methods. Dec. 2005;37(4):331-40.
Ehlers S, et al. "Alphabeta T cell receptor-positive cells and interferon-gamma, but not inducible nitric oxide synthase, are critical for granuloma necrosis in a mouse model of mycobacteria-induced pulmonary immunopathology," J Exp Med. Dec. 17, 2001;194(12):1847-59.
Madrenas, J. et al., "Thymus-independent Expression of Truncated T Cell Receptor-a mRNA in Murine Kidney," The Journal of Immunology, vol. 148, No. 2, pp. 612-619, Jan. 15, 1992. Abstract.
Roberts, S. et al., "T-Cell a~+ and yo+ Deficient Mice Display Abnormal but Distinct Phenotypes Toward a Natural, Widespread Infection of the Intestinal Epithelium," PNAS, Oct. 1996, vol. 93, pp. 11174-11779.
Stoss et al., Brian Research Protocols 4 (1999).383-394.
Szczepanik, M. et al., "Gamma.delta. T Cells from Tolerized a~ T Cell Receptor (TCR)-deficient Mice Inhibit Contact Sensitivity-effector T Cells in Vivo, and Their Interferon-y Production in Vitro," The Journal of Experimental Medicine, Dec. 1, 1996, vol. 184, pp. 2129-2139.
Trickett et al., Journal of Immunological Methods 275 (2003) 251-255.
Wormley, F. et al., "Resistance of T-Cell Receptor o-Chain-Deficient Mice to Experimental Candida Albicans Vaginitis," Infection and Immunity, Nov. 2001, vol. 69, No. 11, pp. 7162-7164.
Wilson et al., Biochimie 91 (2009) 1342-1345.
Kudo K, Imai C, Lorenzini P, Kamiya T, Kono K, Davidoff AM, Chng WJ, Campana D. T lymphocytes expressing a CD16 signaling receptor exert antibody-dependent cancer cell killing. Cancer research. Jan. 1, 2014;74(1):93-103.
Kumagai MA, Coustan-Smith E, Murray DJ, Silvennoinen O, Murti KG, Evans WE, Malavasi F, Campana D. Ligation of CD38 suppresses human B lymphopoiesis. The Journal of experimental medicine. Mar. 1, 1995;181(3):1101-10.
Labrecque N et al. How Much TCR Does a T Cell Need? Immunity. Jul. 2001;15(1):71-82.
Lake DF, Salgaller ML, Van Der Bruggen P, Bernstein RM, Marchalonis JJ. Construction and binding analysis of recombinant single-chain TCR derived from tumor-infiltrating lymphocytes and a cytotoxic T lymphocyte clone directed against MAGE-1. Int Immunol. 1999;11(5):745-51.
Lamers CHJ, Willemsen RA, Luider BA, Debets R, Bolhuis RLH. Protocol for gene transduction and expansion of human T lymphocytes for clinical immunogene therapy of cancer. Cancer Gene Ther. 2002;9(7):613-23.
Lampson LA. Beyond inflammation: site-directed immunotherapy. Immunol Today. 1998;19(1):17-22.
Lapteva N, Durett AG, Sun J, Rollins LA, Huye LL, Fang J, Dandekar V, Mei Z, Jackson K, Vera J, Ando J. Large-scale ex vivo expansion and characterization of natural killer cells for clinical applications. Cytotherapy. Oct. 1, 2012;14(9):1131-43.
Lee DA, Verneris MR, Campana D. Acquisition, preparation, and functional assessment of human NK cells for adoptive immunotherapy. In: Immunotherapy of Cancer: Methods and Protocols. Humana Press; 2010. p. 61-77.
Leibman RS, Riley JL Engineering T cells to Functionally Cure HIV-1 Infection. Mol Ther. 2015;23(7):1149-59.
Leivas A, Pérez-Martínez A, Blanchard MJ, Clavero EM, Campana D, Lahuerta JJ, Martínez-López J. Autologous Activated and Expanded Natural Killer Cells Are Safe and Clinically Actives in Multiple Myeloma. Blood. Dec. 3, 2015;126(23):1856.
Leivas A, Pérez-Martínez A, Blanchard MJ, Clavero EM, Campana D, Lahuerta JJ, Martínez-López J. Multiple Infusions of Autologous Activated and Expanded Natural Killer Cells: A New Therapeutic Option for Multiple Myeloma. Clinical Lymphoma Myeloma and Leukemia. Sep. 1, 2015;15:e297-8.
Leivas A, Risueño RM, Pérez-Martinez A, Campana D, Lahuerta JJ, Martínez-López J. Autologous Activated and Expanded Natural Killer Cells Destroy Multiple Myeloma Clonogenic Tumor Cells through NKG2D and Its Ligands. Clinical Lymphoma Myeloma and Leukemia. Sep. 1, 2015;15:e245-6.
Leung W, Campana D, Yang J, Pei D, Coustan-Smith E, Gan K, Rubnitz JE, Sandlund JT, Ribeiro RC, Srinivasan A, Hartford C. High success rate of hematopoietic cell transplantation regardless of donor source in children with very high-risk leukemia. Blood. Jul. 14, 2011;118(2):223-30.
Li L, Wolfraim L, Allen C, Viley A, Fujisaki H, Campana D, Fratantoni JC, Peshwa MV. A Highly Efficient, Clinically Applicable Transfection Method to Redirect the Specificity of Immune Cells and Enhance Their Anti-Tumor Capacity. Blood. Nov. 16, 2008;112(11):3894.
Liao KW, Chou WC, Lo YC, Roller SR. Design of transgenes for efficient expression of active chimeric proteins on mammalian cells. Biotechnol Bioeng. 2001;73(4):313-23.
Lim KS, Kua LF, Mimura K, Shiraishi K, Chng WJ, Yong WP, Campana D, Kono K. Implication of highly cytotoxic natural killer cells for esophageal cancer treatment. Cancer Research. Aug. 1, 2015;75(15 Supplement):3148.
Liu C, Ma X, Liu B, Chen C, Zhang H. HIV-1 functional cure: will the dream come true? BMC Med. 2015;13(1):284.
Liu L, Patel B, Ghanem MH, Bundoc V, Zheng Z, Morgan RA, et al. Novel CD4-based bispecific chimeric antigen receptor designed for enhanced anti-HIV potency and absence of HIV entry receptor activity. J Virol. 2015;89(13):6685-94.
Lund JA, Spach DH, Collier AC. Future Anti-HIV Therapy. In: Spach DH, Hooton TM, editors. The HIV Manual: A Guide to Diagnosis and Treatment. Oxford University Press; 1996. p. 89-104.
Lund O, Lund OS, Gram G, Nielsen SD, Schønning K, Nielsen JO, et al. Gene therapy of T helper cells in HIV infection: mathematical model of the criteria for clinical effect. Bull Math Biol. 1997;59(4):725-45.
Luszczek W, Morales-Tirado V, van der Merwe M, Kudo K, Campana D, Pillai A. Expanded human regulatory iNKT cells exhibit direct cytotoxicity against hematolymphoid tumor targets. Cancer Research. Apr. 15, 2012;72(8 Supplement):3512.
Ma Q, Gonzalo-Daganzo RM, Junghans RP. Genetically engineered T cells as adoptive immunotherapy of cancer. Cancer Chemother Biol Response Modif. 2002;20:315-41.
Ma Q, Safar M, Holmes E, Wang Y, Boynton AL, Junghans RP. Anti-prostate specific membrane antigen designer T cells for prostate cancer therapy. Prostate. 2004;61(1):12-25.
Marathe JG, Wooley DP. Is gene therapy a good therapeutic approach for HIV-positive patients? Genet Vaccines Ther. 2007;5:5.

(56) References Cited

OTHER PUBLICATIONS

Marin V, Kakuda H, Dander E, Imai C, Campana D, Biondi A, D'Amico G. Enhancement of the anti-leukemic activity of cytokine induced killer cells with an anti-CD19 chimeric receptor delivering a 4-1BB-ζ activating signal. Experimental hematology. Sep. 30, 2007;35(9)1388-97.
Martinius HO. Präklinische Untersuchungen zur Gentherapie der HIV-Infektion mit dem retroviralen Vektor M87o (Preclinical examinations on genetherapy of HIV infection with the retroviral vector M870). (Thesis.) Goethe University Frankfurt; 2007.
Masiero S, Del Vecchio C, Gavioli R, Mattiuzzo G, Cusi MG, Micheli L, et al. T-cell engineering by a chimeric T-cell receptor with antibody-type specificity for the HIV-1 gp120. Gene Ther. 2005;12:299-310.
McGuinness RP, Ge Y, Patel SD, Kashmiri SVS, Lee H-S, Hand PH, et al. Anti-tumor activity of human T cells expressing the CC49-zeta chimeric immune receptor. Hum Gene Ther. 1999;10(2):165-73.
Mihara K, Imai C, Coustan-Smith E, Dome JS, Dominici M, Vanin E, Campana D. Development and functional characterization of human bone marrow mesenchymal cells immortalized by enforced expression of telomerase. British journal of haematology. Mar. 1, 2003;120(5):846-9.
Mihara K, Yanagihara K, Imai C, Kimura A, Campana D. Development of Effective Immunotherapy for B-Cell Non-Hodgkin's Lymphoma with CD19-Specific Cytotoxic T Cells. Blood. Nov. 16, 2004;104(11):3277.
Mihara K, Yanagihara K, Takigahira M, Imai C, Kitanaka A, Takihara Y, Kimura A. Activated T-cell-mediated Immunotherapy With a Chimeric Receptor Against CD38 in B-cell Non-Hodgkin Lymphoma. Journal of Immunotherapy. Sep. 1, 2009;32(7):737-43.
Mihara K, Yanagihara K, Takigahira M, Kitanaka A, Imai C, Bhattacharyya J, Kubo T, Takei Y, Yasunaga SI, Takihara Y, Kimura A. Synergistic and persistent effect of T-cell immunotherapy with anti-CD19 or anti-CD38 chimeric receptor in conjunction with rituximab on B-cell non-Hodgkin lymphoma. British journal of haematology. Oct. 1, 2010;151(1):37-46.
Milone MC, Fish JD, Carpenito C, Carroll RG, Binder GK, Teachey D, Samanta M, Lakhal M, Gloss B, Danet-Desnoyers G, Campana D. Chimeric receptors containing CD137 signal transduction domains mediate enhanced survival of T cells and increased antileukemic efficacy in vivo. Molecular Therapy. Aug. 1, 2009;17(8):1453-64.
Mimura K, Kamiya T, Shiraishi K, Kua LF, Shabbir A, So J, Yong WP, Suzuki Y, Yoshimoto Y, Nakano T, Fujii H. Therapeutic potential of highly cytotoxic natural killer cells for gastric cancer. International Journal of Cancer. Sep. 15, 2014;135(6):1390-8.
Mitra AK, Crews KR, Pounds S, Cao X, Feldberg T, Ghodke Y, Gandhi V, Plunkett W, Dolan ME, Hartford C, Raimondi S. Genetic variants in cytosolic 5'-nucleotidase II are associated with its expression and cytarabine sensitivity in HapMap cell lines and in patients with acute myeloid leukemia. Journal of Pharmacology and Experimental Therapeutics. Oct. 1, 2011;339(1):9-23.
Mitsuyasu RT, Anton PA, Deeks SG, Scadden DT, Connick E, Downs MT, et al. Prolonged survival and tissue trafficking following adoptive transfer of CD4zeta gene-modified autologous CD4(+) and CD8(+) T cells in human immunodeficiency virus-infected subjects. Blood. 2000;96(3):785-93.
Muniappan A, Banapour B, Lebkowski J, Talib S. Ligand-mediated cytolysis of tumor cells: use of heregulin-zeta chimeras to redirect cytotoxic T lymphocytes. Cancer Gene Ther. 2000;7(1):128-34.
Nešić D, Vukmanović S. MHC class I is required for peripheral accumulation of CD8+ thymic emigrants. The Journal of Immunology. Apr. 15, 1998;160(8):3705-12.
Nguyen PT, Duthoit CT, Geiger TL. Induction of tolerance and immunity by redirected B cell-specific cytolytic T lymphocytes. Gene Ther. 2007;14(24):1739-49.
Ni Z, Knorr DA, Bendzick L, Allred J, Kaufman DS. Expression of chimeric receptor CD4ζ by natural killer cells derived from human pluripotent stem cells improves in vitro activity but does not enhance suppression of HIV infection in vivo. Stem Cells. 2014;32(4):1021-31.

Palù G, Li Pira G, Gennari F, Fenoglio D, Parolin C, Manca F. Genetically modified immunocompetent cells in HIV infection. Gene Ther. 2001;8(21):1593-600.
Patel SD, Moskalenko M, Smith D, Maske B, Finer MH, McArthur JG. Impact of chimeric immune receptor extracellular protein domains on T cell function. Gene Ther. 1999;6(3):412-9.
Patel SD, Moskalenko M, Tian T, Smith D, McGuinness R, Chen L, et al. T-cell killing of heterogenous tumor or viral targets with bispecific chimeric immune receptors. Cancer Gene Ther. 2000;7(8):1127-34.
Petrausch U, Schirrmann T. Chimeric Antigen Receptors—"CARs." In: Dübel S, Reichert JM, editors. Handbook of Therapeutic Antibodies. Weinheim, Germany: Wiley-VCH Verlag GmbH & Co; 2014. p. 519-60.
Pinthus JH, Eshhar Z. The T-body approach: towards cancer immunogene therapy. In: Stuhler G, Walden P, editors. Cancer Immune Therapy: Current and Future Strategies. John Wiley & Sons; 2002. p. 287-98.
Pircher M, Schirrmann T, Petrausch U. T Cell Engineering. In: Immuno-Oncology. Basel: Karger; 2015. p. 110-35.
Poeschla EM, Wong-Staal F. Advances in Gene Therapy for HIV and Other Viral Infections. In: The Development of Human Gene Therapy. Cold Spring Harbor Laboratory Press; 1999. p. 573-606.
Prapa M, Caldrer S, Spano C, Bestagno M, Golinelli G, Grisendi G, Petrachi T, Conte P, Horwitz EM, Campana D, Paolucci P. A novel anti-GD2/4-1BB chimeric antigen receptor triggers neuroblastoma cell killing. Oncotarget. Sep. 22, 2015;6(28):24884.
Prapa M, Cerioli D, Caldrer S, Spano C, Bestagno M, Golinelli G, Grisendi G, Sardi I, Da Ros M, Iorio A, Bambi F. Adoptive CAR T Cell Therapy Targeting GD2-Positive Cancers. Cytotherapy. Jun. 1, 2016;18(6):S101.
Protzer U, Abken H. Can engineered "designer" T cells outsmart chronic hepatitis B? Hepat Res Treat. 2010;2010:901216.
Imai C, Iwamoto S, Campana D. A Novel Method for Propagating Primary Natural Killer (NK) Cells Allows Highly Efficient Expression of Anti-CD19 Chimeric Receptors and Generation of Powerful Cytotoxicity Against NK-Resistant Acute Lymphoblastic Leukemia Cells. Blood. Nov. 16, 2004;104(11):306.
Imai C, Iwamoto S, Campana D. Genetic modification of primary natural killer cells overcomes inhibitory signals and induces specific killing of leukemic cells. Blood. Jul. 1, 2005;106(1):376-83.
Imai C, Mihara K, Andreansky M, Nicholson IC, Pui CH, Geiger TL, Campana D. Chimeric receptors with 4-1BB signaling capacity provoke potent cytotoxicity against acute lymphoblastic leukemia. Leukemia. Apr. 1, 2004;18(4):676-84.
Cho D, Campana D. Expansion and activation of natural killer cells for cancer immunotherapy. The Korean journal of laboratory medicine. Apr. 1, 2009;29(2):89-96.
Altvater B, Landmeier S, Pscherer S, Temme J, Schweer K, Kailayangiri S, Campana D, Juergens H, Pule M, Rossig C. 2B4 (CD244) signaling by recombinant antigen-specific chimeric receptors costimulates natural killer cell activation to leukemia and neuroblastoma cells. Clinical Cancer Research. Aug. 1, 2009;15(15):4857-66.
Li L, Liu LN, Feller S, Allen C, Shivakumar R, Fratantoni J, Wolfraim LA, Fujisaki H, Campana D, Chopas N, Dzekunov S. Expression of chimeric antigen receptors in natural killer cells with a regulatory-compliant non-viral method. Cancer gene therapy. Mar. 1, 2010;17(3):147-54.
Shook DR, Campana D. Natural killer cell engineering for cellular therapy of cancer. Tissue antigens. Dec. 1, 2011;78(6):409-15.
Shimasaki N, Fujisaki H, Cho D, Masselli M, Lockey T, Eldridge P, Leung W, Campana D. A clinically adaptable method to enhance the cytotoxicity of natural killer cells against B-cell malignancies. Cytotherapy. Aug. 1, 2012;14(7):830-40.
Shimasaki N, Campana D. Natural killer cell reprogramming with chimeric immune receptors. Synthetic Messenger RNA and Cell Metabolism Modulation: Methods and Protocols. 2013:203-20.
Kamiya T, Chang YH, Campana D. Expanded and Activated Natural Killer Cells for Immunotherapy of Hepatocellular Carcinoma. Cancer immunology research. Jul. 2016;4(7):574-81.
Imai C, Kakuda H, Fujisaki H, Iwamoto S, Campana D. Genetic Modification of Natural Killer Cells for Leukemia Therapies. Antiinflamm Antiallergy Agents Med Chem. 2007;6(2):101-8.

(56) References Cited

OTHER PUBLICATIONS

Moisini I. Humanized Chimeric Receptors in the Therapy of Multiple Sclerosis. (Thesis.) University of Tennessee; 2007.
Wayne A, Kreitman R, Pastan I. Monoclonal antibodies and immunotoxins as new therapeutic agents for childhood acute lymphoblastic leukemia. Am Soc Clin Oncol. 2007;596-601.
Tassev DV. Generation and use of HLA-A2-restricted, peptide-specific monoclonal antibodies and chimeric antigen receptors. (Thesis.) Gernster Sloan Kettering Graduate School of Biomedical Sciences; 2011.
Xu J. Viral and Plasmid Transduction Systems: Methods to Modify Immune Cells for Cancer Immunotherapy. (Thesis.) Uppsala University; 2011.
Hombach AA, Holzinger A, Abken H. The weal and woe of costimulation in the adoptive therapy of cancer with chimeric antigen receptor (CAR)-redirected T cells. Curr Mol Med. 2013;13(7):1079-88.
Torikai H, Reik A, Liu PQ, Zhou Y, Zhang L, Maiti S, Huls H, Miller JC, Kebriaei P, Rabinovitch B, Lee DA. A foundation for universal T-cell based immunotherapy: T cells engineered to express a CD19-specific chimeric-antigen-receptor and eliminate expression of endogenous TCR. Blood. Jun. 14, 2012;119(24):5697-705.
Markiewicz MA, Girao C, Opferman JT, Sun J, Hu Q, Agulnik AA, Bishop CE, Thompson CB, Ashton-Rickardt PG. Long-term T cell memory requires the surface expression of self-peptide/major histocompatibility complex molecules. Proceedings of the National Academy of Sciences. Mar. 17, 1998;95(6):3065-70.
Viret C, Wong FS, Janeway CA. Designing and maintaining the mature TCR repertoire: the continuum of self-peptide: self-MHC complex recognition. Immunity. May 1, 1999;10(5):559-68.
Witherden D, van Oers N, Waltzinger C, Weiss A, Benoist C, Mathis D. Tetracycline-controllable selection of CD4+ T cells: half-life and survival signals in the absence of major histocompatibility complex class II molecules. The Journal of experimental medicine. Jan. 17, 2000;191(2):355-64.
Obst R, van Santen HM, Mathis D, Benoist C. Antigen persistence is required throughout the expansion phase of a CD4+ T cell response. The Journal of experimental medicine. May 16, 2005;201(10):1555-65.
Takada K and Jameson SC. Self-class I MHC molecules support survival of naive CD8 T cells, but depress their functional sensitivity through regulation of CD8 expression levels. J Exp Med. Sep. 28, 2009;206(10):2253-69.
De Riva A, Bourgeois C, Kassiotis G, Stockinger B. Noncognate interaction with MHC class II molecules is essential for maintenance of T cell metabolism to establish optimal memory CD4 T cell function. The Journal of Immunology. May 1, 2007;178(9):5488-95.
Kirberg J, Berns A, Von Boehmer H. Peripheral T cell survival requires continual ligation of the T cell receptor to major histocompatibility complex-encoded molecules. The Journal of experimental medicine. Oct. 20, 1997;186(8):1269-75.
Seddon B, Legname G, Tomlinson P, Zamoyska R. Long-term survival but impaired homeostatic proliferation of naive T cells in the absence of p56lck. Science. Oct. 6, 2000;290(5489):127-31.
Polic B, Kunkel D, Scheffold A, Rajewsky K How αβ T cells deal with induced TCRα ablation. Proceedings of the National Academy of Sciences. Jul. 17, 2001;98(15):8744-9.
Seddon B, Zamoyska R. TCR signals mediated by Src family kinases are essential for the survival of naive T cells. The Journal of Immunology. Sep. 15, 2002;169(6):2997-3005.
Tanchot C, Lemonnier FA, Pérarnau B, Freitas AA, Rocha B. Differential requirements for survival and proliferation of CD8 naive or memory T cells. Science. Jun. 27, 1997;276(5321):2057-62.
Markiewicz MA, Brown I, Gajewski TF. Death of peripheral CD8+ T cells in the absence of MHC class I is Fas-dependent and not blocked by Bcl-xL. European journal of immunology. Oct. 1, 2003;33(10):2917-26.

Boyman O, Cho JH, Tan JT, Surh CD, Sprent J. A major histocompatibility complex class I—dependent subset of memory phenotype CD8+ cells. The Journal of experimental medicine. Jul. 10, 2006;203(7):1817-25.
Takeda S, Rodewald HR, Arakawa H, Bluethmann H, Shimizu T. MHC class II molecules are not required for survival of newly generated CD4+ T cells, but affect their long-term life span. Immunity. Sep. 1, 1996;5(3):217-28.
Brocker T. Survival of mature CD4 T lymphocytes is dependent on major histocompatibility complex class II-expressing dendritic cells. The Journal of experimental medicine. Oct. 20, 1997;186(8):1223-32.
Rooke R, Waltzinger C, Benoist C, Mathis D. Targeted complementation of MHC class II deficiency by intrathymic delivery of recombinant adenoviruses. Immunity. Jul. 1, 1997;7(1):123-34.
Kassiotis G, Garcia S, Simpson E, Stockinger B. Impairment of immunological memory in the absence of MHC despite survival of memory T cells. Nature immunology. Mar. 1, 2002;3(3):244-50.
Huppa JB, Gleimer M, Sumen C, Davis MM. Continuous T cell receptor signaling required for synapse maintenance and full effector potential. Nature immunology. Aug. 1, 2003;4(8):749-55.
Bhandoola A, Tai X, Eckhaus M, Auchincloss H, Mason K, Rubin SA, Carbone KM, Grossman Z, Rosenberg AS, Singer A. Peripheral expression of self-MHC-II influences the reactivity and self-tolerance of mature CD4+ T cells: evidence from a lymphopenic T cell model. Immunity. Oct. 31, 2002;17(4):425-36.
Fischer UB, Jacovetty EL, Medeiros RB, Goudy BD, Zell T, Swanson JB, Lorenz E, Shimizu Y, Miller MJ, Khoruts A, Ingulli E. MHC class II deprivation impairs CD4 T cell motility and responsiveness to antigen-bearing dendritic cells in vivo. Proceedings of the National Academy of Sciences. Apr. 24, 2007;104(17):7181-6.
Isaaz S, Baetz K, Olsen K, Podack E, Griffiths GM. Serial killing by cytotoxic T lymphocytes: T cell receptor triggers degranulation, re-filling of the lytic granules and secretion of lytic proteins via a non-granule pathway. European journal of immunology. Apr. 1, 1995;25(4):1071-9.
Berg NN, Puente LG, Dawicki W, Ostergaard HL. Sustained TCR signaling is required for mitogen-activated protein kinase activation and degranulation by cytotoxic T lymphocytes. The Journal of Immunology. Sep. 15, 1998;161(6)2919-24.
Hudrisier D, Riond J, Mazarguil H, Gairin JE, Joly E. Cutting edge: CTLs rapidly capture membrane fragments from target cells in a TCR signaling-dependent manner. The Journal of Immunology. Mar. 15, 2001;166(6):3645-9.
Doucey MA, Legler DF, Boucheron N, Cerottini JC, Bron C, Luescher IF. CTL activation is induced by cross-linking of TCR/MHC-peptide-CD8/p56lck adducts in rafts. European journal of immunology. May 1, 2001;31(5):1561-70.
Kassiotis G, Zamoyska R, Stockinger B. Involvement of avidity for major histocompatibility complex in homeostasis of naive and memory T cells. The Journal of experimental medicine. Apr. 21, 2003;197(8):1007-16.
Lee KH, Holdorf AD, Dustin ML, Chan AC, Allen PM, Shaw AS. T cell receptor signaling precedes immunological synapse formation. Science. Feb. 22, 2002;295(5559):1539-42.
Abken H, Hombach A, Heuser C. Immune response manipulation: recombinant immunoreceptors endow T-cells with predefined specificity. Cuff Pharm Des. 2003;9(24):1992-2001.
Bahceci E, Rabinovich P, Budak-Alpdogan T, Komarovskaya M, Campana D, Weissman SM. Immunotherapy of B Cell Malignancies Using Transiently Redirected Cytotoxic T Cells. Blood. Nov. 16, 2007;110(11):2750.
Beecham EJ, Ma Q, Ripley R, Junghans RP. Coupling CD28 co-stimulation to immunoglobulin T-cell receptor molecules: the dynamics of T-cell proliferation and death. J Immunother. 2000;23(6):631-42.
Berger C, Berger M, Feng J, Riddell SR. Genetic modification of T cells for immunotherapy. Expert Opin Biol Ther. 2007;7(8):1167-82.
Bitton N, Gorochov G, Debre P, Eshhar Z. Gene therapy approaches to HIV-infection: immunological strategies: use of T bodies and universal receptors to redirect cytolytic T-cells. Front Biosci. 1999;4:D386-93.

(56) References Cited

OTHER PUBLICATIONS

Blankson JN, Persaud D, Siliciano RF. The challenge of viral reservoirs in HIV-1 infection. Annu Rev Med. 2002;53:557-93.
Bohne F, Protzer U. Adoptive T-cell therapy as a therapeutic option for chronic hepatitis B. Journal of Viral Hepatitis. 2007;14(Suppl 1):45-50.
Liu L, et al. "Adoptive T-cell therapy of B-cell malignancies: conventional and physiological chimeric antigen receptors," Cancer Lett. Mar. 2012;316(1):1-5.
Nagorsen D, et al. "Immunomodulatory therapy of cancer with T cell-engaging BiTE antibody blinatumomab," Exp Cell Res. May 15, 2011;317(9):1255-60.
Marin R, et al. "Analysis of HLA-E expression in human tumors," Immunogenetics. Feb. 2003;54(11):767-75.
Palmisano GL, et al. "HLA-E surface expression is independent of the availability of HLA class I signal sequence-derived peptides in human tumor cell lines," Hum Immunol. Jan. 2005;66(1):1-12.
Fujisaki H, Kakuda H, Lockey T, Eldridge PW, Leung W, Campana D. Expanded Natural Killer Cells for Cellular Therapy of Acute Myeloid Leukemia. Blood. Nov. 16, 2007;110(11):2743.
Fujisaki H, Kakuda H, Shimasaki N, Imai C, Ma J, Lockey T, Eldridge P, Leung WH, Campana D. Expansion of highly cytotoxic human natural killer cells for cancer cell therapy. Cancer research. May 1, 2009;69(9):4010-7.
Garg TK, Szmania S, Shi J, Stone K, Moreno-Bost A, Malbrough P, Campana D, Barlogie B, Afar D, van Rhee F. Ex vivo activated natural killer (NK) cells from myeloma patients kill autologous myeloma and killing is enhanced by elotuzumab. Blood. Nov. 16, 2008;112(11):3666.
Garg TK, Szmania SM, Khan JA, Hoering A, Malbrough PA, Moreno-Bost A, Greenway AD, Lingo JD, Li X, Yaccoby S, Suva LJ. Highly activated and expanded natural killer cells for multiple myeloma immunotherapy. Haematologica. Sep. 2012;97(9):1348-56.
Gilham DE, O'Neil A, Hughes C, Guest RD, Kirillova N, Lehane M, et al. Primary polyclonal human T lymphocytes targeted to carcino-embryonic antigens and neural cell adhesion molecule tumor antigens by CD3zeta-based chimeric immune receptors. J Immunother. 2002;25(2):139-51.
Gobbi M, Caligaris-Cappio F, Campana D, Tazzari PL, Bergui L, Cavo M, Tura S. Functional behaviour and immunological phenotype of circulating B lymphocytes in multiple myeloma. Studies with pokeweed mitogen. Clin Exp Immunol. Dec. 1984;58(3):625.
Gray D. A role for antigen in the maintenance of immunological memory. Nat Rev Immunol. Jan. 1, 2002;2(1):60-5.
Grossman Z, Paul WE. Adaptive cellular interactions in the immune system: the tunable activation threshold and the significance of subthreshold responses. Proceedings of the National Academy of Sciences. Nov. 1, 1992;89(21):10365-9.
Grossman Z, Paul WE. Autoreactivity, dynamic tuning and selectivity. Current opinion in immunology. Dec. 1, 2001;13(6):687-98.
Grossman Z, Paul WE. Self-tolerance: context dependent tuning of T cell antigen recognition. Seminars in immunology. Jun. 30, 2000;12(3):197-203.
Guest RD, Hawkins RE, Kirillova N, Cheadle EJ, Arnold J, O'Neill A, et al. The role of extracellular spacer regions in the optimal design of chimeric immune receptors: evaluation of four different scFvs and antigens. J Immunother. 2005;28(3):203-11.
Hamer DH. Can HIV be Cured? Mechanisms of HIV persistence and strategies to combat it. Curr HIV Res. 2004;2(2):99-111.
Hege KM, Cooke KS, Finer MH, Zsebo KM, Roberts MR. Systemic T cell-independent tumor immunity after transplantation of universal receptor-modified bone marrow into SCID mice. J Exp Med. 1996;184(6):2261-9.
Hege KM, Roberts MR. T-cell gene therapy. Curr Opin Biotechnol. 1996;7(6):629-34.
Ho WY, Blattman JN, Dossett ML, Yee C, Greenberg PD. Adoptive immunotherapy: Engineering T cell responses as biologic weapons for tumor mass destruction. Cancer Cell. 2003;3:431-7.

Hochberg J, Mar B, Ayello J, Day N, van de Ven C, Ricci A, Gurnani L, Cairo E, Campana D, Cairo MS. Genetic engineering and significant ex-vivo expansion of cord blood natural killer cells: implications for post-transplant adoptive cellular immunotherapy. Blood. Nov. 16, 2008;112(11):209-.
Hochberg J, Mar B, Ayello J, van de Ven C, Ricci A, Gurnani L, Campana D, Cairo MS. Genetically Reengineered K562 Cells (Antigen Presenting Cells, APC) Significantly Expand Cord Blood (CB) Natural Killer (NK) Cells for Use in Adoptive Cellular Immunotherapy. Pediatric Blood & Cancer. Apr. 24, 2009;52(6):698.
Hombach A, Heuser C, Sircar R, Tillmann T, Diehl V, Pohl C, et al. Characterization of a chimeric T-cell receptor with specificity for the Hodgkin's lymphoma-associated CD30 antigen. J Immunother. 1999;22(6):473-80.
Hombach A, Pohl C, Reinhold U, Abken H. Grafting T cells with tumor specificity: the chimeric receptor strategy for use in immunotherapy of malignant diseases. Hybridoma. 1999;18(1):57-61.
Hombach A, Sircar R, Heuser C, Tillmann T, Diehl V, Kruis W, et al. Chimeric anti-TAG72 receptors with immunoglobulin constant Fc domains and gamma or zeta signalling chains. Int J Mol Med. 1998;2(1):99-103.
Hua CK, Ackerman ME. Engineering broadly neutralizing antibodies for HIV prevention and therapy. Adv Drug Deliv Rev. 2016;103:157-73.
Imai C, Kakihara T, Watanabe A, Ikarashi Y, Hotta H, Tanaka A, Uchiyama M. Acute suppurative thyroiditis as a rare complication of aggressive chemotherapy in children with acute myelogeneous leukemia. Pediatric hematology and oncology. Jan. 1, 2002;19(4):247-53.
Imai C, Mihara K, Andreansky M, Geiger TL, Campana D. T-Cell immunotherapy for B-lineage acute lymphoblastic leukemia using chimeric antigen receptors that deliver 4-1BB-mediated costimulatory signals. Blood. Nov. 16, 2003;102(11):66A-67A.
Imai C, Ross ME, Reid G, Coustan-Smith E, Schultz KR, Pui CH, Downing JR, Campana D. Expression of the adaptor protein BLNK/SLP-65 in childhood acute lymphoblastic leukemia. Leukemia. May 1, 2004;18(5):922-5.
Imai C, Takachi T, Iwabuchi H, Imamura M, Nemoto T, Campana D, Uchiyama M. Interleukin-2 Gene Transduction in Human Natural Killer Cells Augments Their Survival and Anti-Leukemic Capacity. Blood. Nov. 16, 2008;112(11):5437.
Imami N, Gotch F. Prospects for immune reconstitution in HIV-1 infection. Clinical and Experimental Immunology. 2002;127:402-11.
Imamura M, Imai C, Takachi T, Nemoto T, Tanaka A, Uchiyama M. Juvenile myelomonocytic leukemia with less aggressive clinical course and KRAS mutation. Pediatric blood & cancer. Oct. 1, 2008;51(4):569.
Imamura M, Kakihara T, Kobayashi T, Imai C, Tanaka A, Uchiyama M. Anticancer Drugs Overexpress Fas-associated Phosphatase-1 in Some Leukemic Cells. Acta Medica et Biologica. 2004;52(3):81-9.
Imamura M, Shook D, Kamiya T, Shimasaki N, Chai SM, Coustan-Smith E, Imai C, Campana D. Autonomous growth and increased cytotoxicity of natural killer cells expressing membrane-bound interleukin-15. Blood. Aug. 14, 2014;124(7):1081-8.
Irving BA, Weiss A. Surface chimeric receptors as tools in study of lymphocyte activation. Methods Enzymol. 2000;327:210-28.
Iwabuchi H, Kakihara T, Kobayashi T, Imai C, Tanaka A, Uchiyama M, Fukuda T. A gene homologous to human endogenous retrovirus overexpressed in childhood acute lymphoblastic leukemia. Leukemia & lymphoma. Nov. 2004;45(11):2303-6.
Jameson SC, Masopust D. Diversity in T cell memory: an embarrassment of riches. Immunity. Dec. 18, 2009;31(6):859-71.
Jameson SC. Maintaining the norm: T-cell homeostasis. Nature Reviews Immunology. Aug. 1, 2002;2(8):547-56.
Janossy G, Caligaris-Cappio F, Bofill M, Campana D, Janossa M. Development of B Cell Subpopulations in Humans and its Relevance to Malignancy. In Modern Trends in Human Leukemia VI New Results in Clinical and Biological Research Including Pediatric Oncology 1985 (pp. 461-470). Springer Berlin Heidelberg.

(56) References Cited

OTHER PUBLICATIONS

Janossy G, Campana D, Akbar A. Kinetics of T lymphocyte development. In Cell Kinetics of the Inflammatory Reaction 1989 (pp. 59-99). Springer Berlin Heidelberg.
Janossy G, Campana D, Amlot PL. Leukaemia and lymphoma treatment with autologous bone marrow transplantation: preclinical studies. Cancer detection and prevention. 1988;12(1-6):597-604.
Janossy G, Prentice HG, Grob JP, Ivory K, Tidman N, Grundy J, Favrot M, Brenner MK, Campana D, Blacklock HA, Gilmore MJ. T lymphocyte regeneration after transplantation of T cell depleted allogeneic bone marrow. Clinical and experimental immunology. Mar. 1986;63(3):577.
Jensen MC, Tan G, Forman SJ, Wu AM, Raubitschek A. CD20 is a molecular target for scFvFc:zeta receptor redirected T cells: implications for cellular immunotherapy of CD20+ malignancy. Biol Blood Marrow Transplant. 1998;4(2):75-83.
June CH. Protocol for pilot study of autlogous T cells engineered to contain anti-CD19 attached to TCRζ and 4-1BB signaling domains in patients with chemotherapy resistant or refractory CD19+ leukemia and lymphoma. 2009. Retrieved from http://www.med.upenn.edu/junelab/docs/June_protocol_OLF.PDF on Oct. 13, 2016.
Junghans RP. Designer T Cells for Breast Cancer Therapy: Phase I Studies. Boston, Massachusetts; 2001. Retrieved from http://oai.dtic.mil/oai/oai?verb=getRecord&metadataPrefix=html&identifier=ADA398295 on Oct. 11, 2016.
Kanwar VS, Witthuhn B, Campana D, Ihle JN. Lack of constitutive activation of Janus kinases and signal transduction and activation of transcription factors in Philadelphia chromosome-positive acute lymphoblastic leukemia. Blood. Jun. 1, 1996;87(11):4911-2.
Kershaw MH, Darcy PK, Hulett MD, Hogarth PM, Trapani JA, Smyth MJ. Redirected cytotoxic effector function: Requirements for expression of chimeric single chain high affinity immunoglobulin E receptors. J Biol Chem. 1996;271(35):21214-20.
Kitanaka A, Ito C, Coustan-Smith E, Campana D. CD38 ligation in human B cell progenitors triggers tyrosine phosphorylation of CD19 and association of CD19 with lyn and phosphatidylinositol 3-kinase. The Journal of Immunology. Jul. 1, 1997;159(1):184-92.
Kitanaka A, Mano H, Conley ME, Campana D. Expression and activation of the nonreceptor tyrosine kinase Tec in human B cells. Blood. Feb. 1, 1998;91(3):940-8.
Kitanaka A, Suzuki T, Ito C, Nishigaki H, Coustan-Smith E, Tanaka T, Kubota Y, Campana D. CD38-Mediated Signaling Events in Murine Pro-B Cells Expressing Human CD38 With or Without Its Cytoplasmic Domain. J Immunol. Feb. 1999;162:1952-8.
Kitchen SG, Shimizu S, An DS. Stem cell-based anti-HIV gene therapy. Virology. 2011;411(2):260-72.
Kitchen SG, Zack J a. Stem cell-based approaches to treating HIV infection. Curr Opin HIV AIDS. 2011;6(1):68-73.
Koenig S. A lesson from the HIV patient: The immune response is still the bane (or promise) of gene therapy. Nat Med. 1996;2(2):165-167.
Koh S, Shimasaki N, Suwanarusk R, Ho ZZ, Chia A, Banu N, Howland SW, Ong AS, Gehring AJ, Stauss H, Renia L. A practical approach to immunotherapy of hepatocellular carcinoma using T cells redirected against hepatitis B virus. Molecular Therapy—Nucleic Acids. Aug. 1, 2013;2(8):e114.
Krampera M, Perbellini O, Vincenzi C, Zampieri F, Pasini A, Scupoli MT, Guarini A, De Propris MS, Coustan-Smith E, Campana D, Foa R. Methodological approach to minimal residual disease detection by flow cytometry in adult B-lineage acute lymphoblastic leukemia. Haematologica. Jan. 1, 2006;91(8):1109-12.
Pui CH, Relling MV, Sandlund JT, Campana D, Evans WE. Education Session 1: Treatment OF Acute Leukemia. Oct. 1999. Retrieved from: http://citeseerx.ist.psu.edu/viewdoc/download?doi=10.1.1.622.3615&rep=rep1&type=pdf on Sep. 15, 2016.
Pule M, Finney HM, Lawson ADG. Artificial T-cell receptors. Cytotherapy. 2003;5(3):211-26.
Quinn ER, Lum LG, Trevor KT. T cell activation modulates retrovirus-mediated gene expression. Hum Gene Ther. 1998;9(10):1457-67.
Rabinovich PM, Komarovskaya ME, Ye ZJ, Imai C, Campana D, Bahceci E, Weissman SM. Synthetic messenger RNA as a tool for gene therapy. Human gene therapy. Oct. 1, 2006;17(10):1027-35.
Regueiro JR, Martin-Fernandez JM, Melero I. Immunity and gene therapy: benefits and risks. Inmunologia. 2004;23(1):56-62.
Riley JL, Jun. CH. Genetically Modified T Cells for Human Gene Therapy. In: Dropulic B, Carter B, editors. Concepts in Genetic Medicine. Hoboken, New Jersey: John Wiley & Sons, Inc; 2008. p. 193-205.
Roberts MR, Cooke KS, Tran A-C, Smith KA, Lin WY, Wang M, et al. Antigen-specific cytolysis by neutrophils and NK cells expressing chimeric immune receptors bearing zeta or gamma signaling domains. J Immunol. 1998;161(1):375-84.
Roberts MR, Qin L, Zhang DE, Smith DH, Tran AC, Dull TJ, Groopman JE, Capon DJ, Byrn RA, Finer MH. Targeting of human immunodeficiency virus-infected cells by CD8+ T lymphocytes armed with universal T-cell receptors. Blood. Nov. 1, 1994;84(9):2878-89.
Rondon IJ, Marasco WA. Gene Therapy for HIV-1 Using Intracellular Antibodies Against HIV-1 Gag Proteins. In: Marasco WA, editor. Intrabodies: Basic Research and Clinical Gene Therapy Applications. Springer Berlin Heidelberg; 1998. p. 163-81.
Rondon IJ, Marasco WA. Intracellular antibodies (intrabodies) for gene therapy of infectious diseases. Annu Rev Microbiol. 1997;51:257-83.
Rossi JJ, June CH, Kohn DB. Genetic therapies against HIV. Nat Biotechnol. 2007;25(12):1444-54.
Rossig C, Bollard CM, Nuchtem JG, Rooney CM, Brenner MK. Epstein-Barr virus-specific human T lymphocytes expressing antitumor chimeric T-cell receptors: potential for improved immunotherapy. Blood. 2002;99(6):2009-16.
Rossig C, Brenner MK. Chimeric T-cell receptors for the targeting of cancer cells. Acta Haematol. 2003;110(2-3):154-9.
Rossig C, Brenner MK. Genetic modification of T lymphocytes for adoptive immunotherapy. Mol Ther. 2004;10(1):5-18.
Roszkowski JJ, Nishimura MI. Retroviral-Mediated Gene Transfer for Engineering Tumor-Reactive T-Cells. In: Disis ML, editor. Immunotherapy of Cancer. Humana Press; 2006. p. 213-33.
Bahu GK, Sango K, Selliah N, Ma Q, Skowron G, Junghans RP. Anti-HIV designer T cells progressively eradicate a latently infected cell line by sequentially inducing HIV reactivation then killing the newly gp120-positive cells. Virology. 2013;446(1-2):268-75.
Schirrmann T, Pecher G. Emerging Therapeutic Concepts III: Chimeric Immunoglobulin T Cell Receptors, T-Bodies. In: Dübel S, editor. Handbook of Therapeutic Antibodies. Weinheim, Germany: Wiley-VCH Verlag GmbH; 2008. p. 533-71.
Scholler J, Brady TL, Binder-Scholl G, Hwang W-T, Plesa G, Hege KM, et al. Decade-long safety and function of retroviral-modified chimeric antigen receptor T cells. Sci Transl Med. 2012;4(132):132ra53.
Seow SV, Chai SMH, Tan PL, Yeoh AEJ, Campana D. Expansion and activation of allogeneic NK cells for adoptive immunotherapy of advanced leukemia / lymphoma. In International Immunology Meeting Abstracts Aug. 1, 2010 (vol. 22, No. Suppl 1 Pt 2, pp. ii121-ii123). Oxford University Press.
Severino ME, Sarkis PTN, Walker BD, Yang OO. Chimeric immune receptor T cells bypass class I requirements and recognize multiple cell types relevant in HIV-1 infection. Virology. 2003;306(2):371-5.
Shi J, Szmania S, Tricot G, Garg TK, Malaviarachchi PA, Moreno-Bost A, Stone K, Zhan F, Campana D, Shaughnessy J, Barlogie B. Activation and Expansion of Natural Killer (NK) Cells with Potent Cytotoxicity for Multiple Myeloma. Blood. Nov. 16, 2008;112(11):2758.
Shibaguchi H, Luo NX, Kuroki M, Zhao J, Huang J, Hachimine K, et al. A fully human chimeric immune receptor for retargeting T-cells to CEA-expressing tumor cells. Anticancer Res. 2006;26(6A):4067-72.
Shimasaki N, Coustan-Smith E, Kamiya T, Campana D. Expanded and armed natural killer cells for cancer treatment. Cytotherapy. Nov. 30, 2016;18(11):1422-34.
Sorg T, Methali M. Gene therapy for AIDS. Transfusion science. Jun. 30, 1997;18(2)277-89.
Sprent J, Surh CD. T cell memory. Annual review of immunology. Apr. 2002;20(1):551-79.

(56) References Cited

OTHER PUBLICATIONS

Starr TK, Jameson SC, Hogquist KA. Positive and negative selection of T cells. Annual review of immunology. Apr. 2003;21(1):139-76.
Surh CD, Sprent J. Homeostasis of naive and memory T cells. Immunity. Dec. 19, 2008;29(6):848-62.
Surh CD, Sprent J. Regulation of mature T cell homeostasis. In: Seminars in immunology Jun. 30, 2005 (vol. 17, No. 3, pp. 183-191). Academic Press.
Szmania S, Garg TK, Lapteva N, Lingo JD, Greenway AD, Stone K, Woods E, Khan J, Stivers J, Nair B, Baxter-Lowe LA. Fresh ex vivo expanded natural killer cells demonstrate robust proliferation in vivo in high-risk relapsed multiple myeloma (MM) patients. Blood. Nov. 16, 2012;120(21):579.
Szmania S, Lapteva N, Garg T, Greenway A, Lingo J, Nair B, Stone K, Woods E, Khan J, Stivers J, Panozzo S. Ex Vivo Expanded Natural Killer Cells Demonstrate Robust Proliferation In Vivo in High-Risk Relapsed Multiple Myeloma Patients. Journal of immunotherapy. Jan. 2015;38(1):24.
Szmania S, Lapteva N, Garg TK, Lingo JD, Greenway AD, Bost A, Stone K, Khan J, Woods E, Nair B, Campana D. Expanded natural killer (NK) cells for immunotherapy: fresh and made to order. Blood. Nov. 16, 2012;120(21):1912.
Takachi T, Iwabuchi H, Imamura M, Imai C. Lymphoblastic lymphoma with mature b-cell immunophenotype and MLL-AF9 in a child. Pediatric blood & cancer. Dec. 15, 2011;57(7):1251-2.
Todisco E, Suzuki T, Srivannaboon K, Coustan-Smith E, Raimondi SC, Behm FG, Kitanaka A, Campana D. CD38 ligation inhibits normal and leukemic myelopoiesis. Blood. Jan. 15, 2000;95(2):535-42.
Tsui L V, Kelly M, Zayek N, Rojas V, Ho K, Ge Y, et al. Production of human clotting Factor IX without toxicity in mice after vascular delivery of a lentiviral vector. Nat Biotechnol. 2002;20(1):53-7.
Uherek C, Groner B, Wels W. Chimeric antigen receptors for the retargeting of cytotoxic effector cells. J Hematother Stem Cell Res. 2001;10(4):523-34.
Von Boehmer H, Kisielow P. Self-nonself discrimination by T cells. Science. Jun. 15, 1990;248(4961):1369-73.
Von Laer D, Baum C, Protzer U. Antiviral gene therapy. In: Kräusslich H-G, Bartenschlager R, editors. Handbook of Experimental Pharmacology. Springer Berlin Heidelberg; 2009. p. 265-97.
Voskens CJ, Watanabe R, Rollins S, Campana D, Hasumi K, Mann DL. Ex-vivo expanded human NK cells express activating receptors that mediate cytotoxicity of allogeneic and autologous cancer cell lines by direct recognition and antibody directed cellular cytotoxicity. Journal of Experimental & Clinical Cancer Research. Oct. 11, 2010;29(1):1.
Walker BD. Immunotherapy with immune reconstitution and HIV. 2001;1-40. Retrieved from aids-chushi.or.jp on Oct. 13, 2016.
Walker RE, Bechtel CM, Natarajan V, Baseler M, Hege KM, Metcalf JA, et al. Long-term in vivo survival of receptor-modified syngeneic T cells in patients with human immunodeficiency virus infection. Blood. 2000;96(2):467-74.
Wang G, Chopra RK, Royal RE, Yang JC, Rosenberg SA, Hwu P. A T cell-independent antitumor response in mice with bone marrow cells retrovirally transduced with an antibody/Fc-γ chain chimeric receptor gene recognizing a human ovarian cancer antigen. Nat Med. 1998;4(2):168-72.
Wang W, Erbe AK, Alderson KA, Phillips E, Gallenberger M, Gan J, Campana D, Hank JA, Sondel PM. Human NK cells maintain licensing status and are subject to killer immunoglobulin-like receptor (KIR) and KIR-ligand inhibition following ex vivo expansion. Cancer Immunology, Immunotherapy. Sep. 1, 2016;65(9)1047-59.
Weijtens MEM, Hart EH, Bolhuis RLH. Functional balance between T cell chimeric receptor density and tumor associated antigen density: CTL mediated cytolysis and lymphokine production. Gene Ther. 2000;7(1):35-42.
Weijtens MEM, Willemsen RA, Hart EH, Bolhuis RLH. A retroviral vector system "STITCH" in combination with an optimized single chain antibody chimeric receptor gene structure allows efficient gene transduction and expression in human T lymphocytes. Gene Ther. 1998;5:1195-203.
Weijtens MEM. Immune-gene therapy for renal cancer chimeric receptor-mediated lysis of tumor cells. (Thesis.) Erasmus University Rotterdam; 2001.
Wickremasinghe RG, Piga A, Campana D, Yaxley JC, Hoffbrand AV. Rapid down-regulation of protein kinase C and membrane association in phorbol ester-treated leukemia cells. FEBS letters. Oct. 7, 1985;190(1):50-4.
Willcox N, Schluept M, Sommer N, Campana D, Janossy G, Brown AN, Newsom-Davist J. Variable corticosteroid sensitivity of thymic cortex and medullary peripheral-type lymphoid tissue in myasthenia gravis patients: structural and functional effects. QJM. Nov. 1, 1989;73(2):1071-87.
Willemsen RA, Debets R, Chames P, Bolhuis RLH. Genetic engineering of T cell specificity for immunotherapy of cancer. Hum Immunol. 2003;64(1):56-68.
Willemsen RA, Debets R, Hart EH, Hoogenboom HR, Bolhuis RLH, Chames P. A phage display selected fab fragment with MHC class I-restricted specificity for MAGE-A1 allows for retargeting of primary human T lymphocytes. Gene Ther. 2001;8(21):1601-8.
Wong Jr. KK, Chatterjee S. Adeno-associated virus based vectors as antivirals. In: Berns KI, Giraud C, editors. Adeno-Associated Virus (AAV) Vectors in Gene Therapy. Springer-Verlag Berlin Heidelberg; 1996. p. 145-70.
Wu AM, Tan GJ, Sherman MA, Clarke P, Olafsen T, Forman SJ, et al. Multimerization of a chimeric anti-CD20 single-chain Fv-Fc fusion protein is mediated through variable domain exchange. Protein Eng. 2001;14(12):1025-33.
Wu C-Y, Roybal KT, Puchner EM, Onuffer J, Lim WA. Remote control of therapeutic T cells through a small molecule-gated chimeric receptor. Science. 2015;350(6258):aab4077.
Yang OO, Nguyen PT, Kalams SA, Dorfman T, Gottlinger HG, Stewart S, et al. Nef-Mediated Resistance of Human Immunodeficiency Virus Type 1 to Antiviral Cytotoxic T Lymphocytes. J Virol. 2002;76(4):1626-31.
Yang OO, Tran A-C, Kalams SA, Johnson RP, Roberts MR, Walker BD. Lysis of HIV-1-infected cells and inhibition of viral replication by universal receptor T cells. Proc Natl Acad Sci U S A. 1997;94(21):11478-83.
Yang OO, Walker BD. CD8+ cells in human immunodeficiency virus type 1 pathogenesis: cytolytic and noncytolytic inhibition of viral replication. Adv Immunol. 1997;66:273-311.
Yel L, Minegishi Y, Coustan-Smith E, Buckley RH, Trübel H, Pachman LM, Kitchingman GR, Campana D, Rohrer J, Conley ME Mutations in the mu heavy-chain gene in patients with agammaglobulinemia. New England Journal of Medicine. Nov. 14, 1996;335(20):1486-93.
Yun CO, Nolan KF, Beecham EJ, Reisfeld RA, Junghans P. Targeting of T Lymphocytes to Melanoma Cells Through Chimeric Anti-GD3 Immunoglobulin T-Cell Receptors. Neoplasia. 2000;2(5):449-59.
Zhu Y, Liu H, Wang Y, Wang B, Qian Q. Screening and Functional Research on Jurkat Cell Strain of Stable Chimeric Antigen Receptor Expression. Sci online. 2013. Retrieved from http://www.paper.edu.cn/download/downPaper/201302-359 on Oct. 13, 2016.
Zhu Y, Liu H, Wang Y, Wang B, Qian Q. Screening of Jurkat cells expressing FLT1-CAR and their chemotaxis to VEGF. Chinese J Cancer Biother. 2013;20(5):559-64.
Sigma-Aldrich in their Cook Book of Sep. 2010, vol. 12, Fundamental Techniques in Cell Culture Laboratory Handbook—2nd Edition, pp. 1-4.
Bisset et al., Eur J. Haematol 2004: 72: 203-212.
Groh et al., Nat Immunol Mar. 2001;2(3):255-60.
Kowolik et al., Cancer Res 2006;66(22):10995-1004.
Okamotoa et al., Cancer Res Nov. 10, 2009;69(23):9003-11.
Yang et al., International Immunology 2007;19(9):1083-1093.
Cooper et al., Blood Feb. 15, 2005;105(4):1622-31.
Pardoll, Nat Biotechnol Dec. 2002;20(12):1207-8.
Cooper et al., Cytotherapy 2006;8(2):105-117.

(56) References Cited

OTHER PUBLICATIONS

Merriam-Webster dictionary definition for "isolated," <http://www.merriam-webster.com/dictionary/isolated> downloaded Oct. 14, 2014, pp. 1-2.
Pamela Stanley lab wiki, "Transfection of Cells with DNA," <http://stanxterm.aecom.yu.edu/wiki/index.php?page=Transfection> Aug. 13, 2009, pp. 1-4.
Schwab et al., J. of Imm. Sep. 1985;135(3):1714-8.
Alegre et al., J. of Imm., Jun. 1992;148(11):3461-68.
Bridgeman et al., J Immunol 2010;184:6938-6949.
Barber et al., Experimental Hematology 2008;36:1318-1328.
Schumacher, Nat Rev Immunol. Jul. 2002;2(7):512-9.
Eagle et al., Curr Immunol Rev. Feb. 2009;5(1):22-34.
Basu et al., Clinical Immunology 2008;129:325-332.
Scheer et al., Methods Mol. Biol. Jul. 1, 2008;506:207-19.
Llano et al., Methods Mol Biol. Jan. 1, 2008;485:257-70.
Polic et al., PNAS Jul. 17, 2001;98(15):8744-9.
Gascoigne et al., J. Biol. Chem. 1990;265:9296-9301.
Rubin et al., Microscopy Research and Technique 2000;51:112-120.
Chan SM, et al. "Single-cell analysis of siRNA-mediated gene silencing using multiparameter flow cytometry," Cytometry A. Feb. 2006;69(2):59-65.
Imai et al. "Genetic modification of T cells for cancer therapy," J Biol Regul Homeost Agents. Jan.-Mar. 2004;18(1):62-71.
Kambayashi T, et al. "IL-2 down-regulates the expression of TCR and TCR-associated surface molecules on CD8(+) T cells," Eur J Immunol. Nov. 2001;31(11):3248-54.
Okamoto S, et al. "Improved expression and reactivity of transduced tumor-specific TCRs in human lymphocytes by specific silencing of endogenous TCR," Cancer Res. Dec. 1, 2009;69(23):9003-11.
Irving BA, et al. "The cytoplasmic domain of the T cell receptor zeta chain is sufficient to couple to receptor-associated signal transduction pathways," Cell. Mar. 8, 1991;64(5):891-901.
Levin SD, et al. "A dominant-negative transgene defines a role for p56Ick in thymopoiesis," EMBO J. Apr. 1993;12(4):1671-80.
Wu J, et al. "A functional T-cell receptor signaling pathway is required for p95vav activity," Mol Cell Biol. Aug. 1995;15(8):4337-46.
"Viral Antigens." ProSpec Protein Specialists. Web. Sep. 10, 2010. < http://www.prospecbio.com/Viral_Antigens/>. Internet Archive. <https://web.archive.org/web/20100910230148/http://www.prospecbio.com:80/Viral_Antigens/>.
"Products & Ordering—Recombinant Proteins." Jena Bioscience. Web. Sep. 2, 2010. <http://www.jenabioscience.com/cms/en/1/browse/110_recombinant_proteins.html>. Internet Archive. <https://web.archive.org/web/20100902050651/http://www.jenabioscience.com/cms/en/1/browse/110_recombinant_proteins.html>.

* cited by examiner

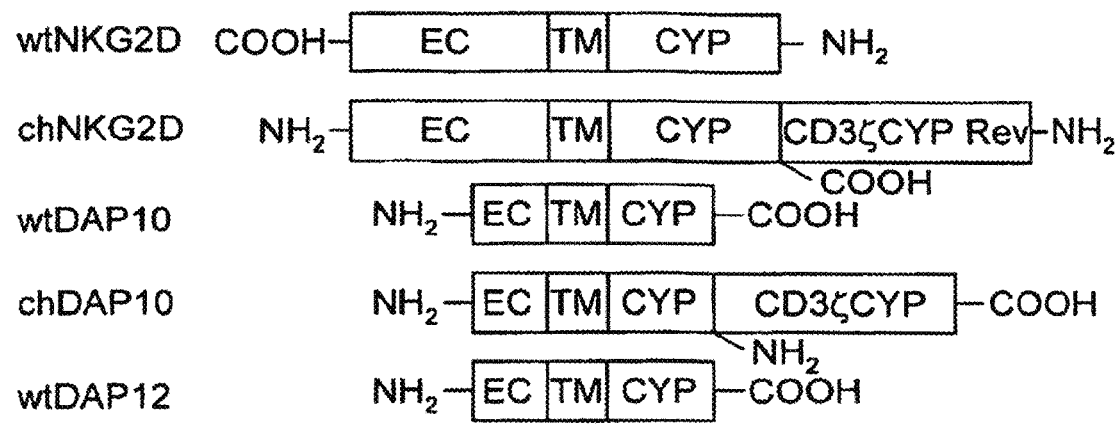

T-CELL RECEPTOR-DEFICIENT T CELL COMPOSITIONS

CROSS-REFERENCE TO RELATED APPLICATIONS

This application is a divisional of U.S. patent application Ser. No. 15/383,717, filed on Dec. 19, 2016, now U.S. Pat. No. 9,821,011, which is a divisional of U.S. patent application Ser. No. 14/934,256, filed Nov. 6, 2015, which is a divisional of U.S. patent application Ser. No. 13/502,978, filed Aug. 7, 2012, now U.S. Pat. No. 9,181,527, which is a 371 national stage of international application no. PCT/US2010/54846, filed Oct. 29, 2010, which claims the benefit of priority to U.S. provisional patent application No. 61/255,980, filed Oct. 29, 2009, the disclosures of all of which are herein incorporated by reference in their entirety.

This invention was made with government support under contract number CA 130911 awarded by the National Institutes of Health. The government has certain rights in the invention.

SEQUENCE LISTING

The sequence listing in the file named "48307o0115" having a size of 32,049 bytes that was created Nov. 16, 2017 is hereby incorporated by reference in its entirety.

BACKGROUND OF THE INVENTION

Field of the Invention

The invention is directed to TCR-deficient T cells, methods of making and using TCR-deficient T cells, and methods of using these TCR-deficient T cells to address diseases and disorders. In one embodiment, the invention broadly relates to TCR-deficient T cells, isolated populations thereof, and compositions comprising the same. In another embodiment of the invention, said TCR-deficient T cells are further designed to express a functional non-TCR receptor. The invention also pertains to methods of making said TCR-deficient T cells, and methods of reducing or ameliorating, or preventing or treating, diseases and disorders using said TCR-deficient T cells, populations thereof, or compositions comprising the same.

Description of Related Art

The global burden of cancer doubled between 1975 and 2000, and cancer is expected to become the leading cause of death worldwide by 2010. According to the American Cancer Society, it is projected to double again by 2020 and to triple by 2030. Thus, there is a need for more effective therapies to treat various forms of cancer. Ideally, any cancer therapy should be effective (at killing cancerous cells), targeted (i.e. selective, to avoid killing healthy cells), permanent (to avoid relapse and metastasis), and affordable. Today's standards of care for most cancers fall short in some or all of these criteria.

Cellular immunotherapy has been shown to result in specific tumor elimination and has the potential to provide specific and effective cancer therapy (Ho, W. Y. et al. 2003. *Cancer Cell* 3:1318-1328; Morris, E. C. et al. 2003. *Clin. Exp. Immunol.* 131:1-7; Rosenberg, S. A. 2001. *Nature* 411:380-384; Boon, T. and P. van der Bruggen. 1996. 1 Exp. Med. 183:725-729). T cells have often been the effector cells of choice for cancer immunotherapy due to their selective recognition and powerful effector mechanisms. T cells recognize specific peptides derived from internal cellular proteins in the context of self-major histocompatability complex (MHC) using their T cell receptors (TCR).

It is recognized in the art that the TCR complex associates in precise fashion by the formation of dimers and association of these dimers (TCR-alpha/beta, CD3-gamma/epsilon, CD3-delta/epsilon, and CD3-zeta dimer) into one TCR complex that can be exported to the cell surface. The inability of any of these complexes to form properly will inhibit TCR assembly and expression (Call, M. E. et al., (2007) Nature Rev. Immunol., 7:841-850; Call, M. E. et al., (2005) Annu. Rev. Immunol., 23:101-125).

Particular amino acid residues in the respective TCR chains have been identified as important for proper dimer formation and TCR assembly. In particular, for TCR-alpha, these key amino acids in the transmembrane portion are arginine (for association with CD3-zeta) and lysine (for association with the CD3-epsilon/delta dimer). For TCR-beta, the key amino acid in the transmembrane portion is a lysine (for association with CD3-epsilon/gamma dimer). For CD3-gamma, the key amino acid in the transmembrane portion is a glutamic acid. For CD3-delta, the key amino acid in the transmembrane portion is an aspartic acid. For CD3-epsilon, the key amino acid in the transmembrane portion is an aspartic acid. For CD3-zeta, the key amino acid in the transmembrane portion is an aspartic acid (Call, M. E. et al., (2007) Nature Rev. Immunol., 7:841-850; Call, M. E. et al., (2005) Annu. Rev. Immunol., 23:101-125).

Peptides derived from altered or mutated proteins in tumors can be recognized by specific TCRs. Several key studies have led to the identification of antigens associated with specific tumors that have been able to induce effective cytotoxic T lymphocyte (CTL) responses in patients (Ribas, A. et al. 2003. *J. Clin. Oncol.* 21:2415-2432). T cell effector mechanisms include the ability to kill tumor cells directly and the production of cytokines that activate other host immune cells and change the local tumor microenvironment. Theoretically, T cells could identify and destroy a tumor cell expressing a single mutated peptide. Adoptive immunotherapy with CTL clones specific for MART1 or gp100 with low dose IL-2 has been effective in reduction or stabilization of tumor burden in some patients (Yee, C. et al. 2002. *Proc. Natl. Acad. Sci. USA* 99:16168-16173). Other approaches use T cells with a defined anti-tumor receptor. These approaches include genetically modifying CTLs with new antigen-specific T cell receptors that recognize tumor peptides and MHC, chimeric antigen receptors (CARS) derived from single chain antibody fragments (scFv) coupled to an appropriate signaling element, or the use of chimeric NK cell receptors (Ho, W. Y. et al. 2003. Cancer Cell 3:431-437; Eshhar, Z. et al. 1993. Proc. Natl. Acad. Sci. USA 90:720-724; Maher, J. and E. T. Davies. 2004. Br. J. Cancer 91:817-821; Zhang, T. et al. 2005. *Blood* 106:1544-1551).

Cell-based therapies are used in patients who have failed conventional chemotherapy or radiation treatments, or have relapsed, often having attempted more than one type of therapy. The immune cells from patients with advanced cancer, who may have gone through rounds of chemotherapy, do not respond as robustly as healthy individuals. Moreover, cancer patients are often elderly and may suffer from other diseases that may limit the potential of their immune cells to become primed effector cells, even after in vitro activation and expansion. In addition, each cancer patient must provide a sufficient number of their own immune cells in order for them to be engineered to express a new immune receptor. Because each therapy must be custom made for the patient, this process requires weeks from the time the decision to undertake such therapy is made; meanwhile, the cancer continues to grow. U.S. patent application publication no. US 2002/0039576 discloses a method for modulating T cell activity, where the T cells used have a phenotype of $CD3^+$-$\alpha\beta$-$TcR^+CD4^-CD8^-CD28^-$ $NK1.1^-$. U.S. patent application publication no. US 2006/0166314 discloses use of mutated T cells to treat cancer where the T cells are ones with a T cell response-mediating MDM2 protein-specific $\alpha\beta$-T cell receptor.

Cancer is not the only disease wherein T cell manipulation could be effective therapy. It is known that active T cell receptors on T cells are critical to the response of the body to stimulate immune system activity. For example, it has been shown that T cell receptor diversity plays a role in graft-versus-host-disease (GVHD), in particular chronic GVHD (Anderson et al. (2004) *Blood* 104:1565-1573). In fact, administration of T cell receptor antibodies has been shown to reduce the symptoms of acute GVHD (Maeda et al. (2005) *Blood* 106:749-755).

There remains a need for more effective T cell-based therapies for the treatment of certain diseases and disorders, and methods of treatment based on the design of new types of T cells.

BRIEF SUMMARY OF THE INVENTION

In one embodiment, this invention broadly relates to isolated, modified T cells that do not express a functional T cell receptor (TCR). In this embodiment, the T cells are TCR-deficient in the expression of a functional TCR. In another embodiment of the invention, TCR-deficient T cells are engineered to express a functional non-TCR receptor, such as for example a chimeric receptor. These cells also function as a platform to allow the expression of other targeting receptors, receptors that may be useful in specific diseases, while retaining the effector functions of T cells, albeit without a functioning TCR.

The invention contemplates populations of TCR-deficient T cells, and compositions comprising the same. The invention also contemplates methods of making said TCR-deficient T cells, and methods of reducing or ameliorating, or preventing or treating, diseases and disorders using said TCR-deficient T cells, populations thereof, or therapeutic compositions comprising the same. In one embodiment, this composition can be used to treat cancer, infection, one or more autoimmune disorders, radiation sickness, or to prevent or treat graft versus host disease (GVHD) or transplantation rejection in a subject undergoing transplant surgery.

BRIEF DESCRIPTION OF THE DRAWING

FIG. 1 illustrates chimeric NK receptors described herein. Extracellular (EC), transmembrane (TM), and cytoplasmic (Cyp) portions are indicated. Wild-type (WT) and chimeric (CH) forms of the receptors are indicated, wherein $NH_2$ denotes the N-terminus and COOH denotes the C-terminus.

DETAILED DESCRIPTION OF PREFERRED EMBODIMENTS

Definitions

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention which will be limited only by the appended claims.

As used herein the singular forms "a", "and", and "the" include plural referents unless the context clearly dictates otherwise. Thus, for example, reference to "a cell" includes a plurality of such cells and reference to "the protein" includes reference to one or more proteins and equivalents thereof known to those skilled in the art, and so forth. All technical and scientific terms used herein have the same meaning as commonly understood to one of ordinary skill in the art to which this invention belongs unless clearly indicated otherwise.

In the context of the present invention, by a "TCR-deficient T cell", or a similar phrase is intended an isolated T cell(s) that lacks expression of a functional TCR, is internally capable of inhibiting its own TCR production, and further wherein progeny of said T cell(s) may also be reasonably expected to be internally capable of inhibiting their own TCR production. Internal capability is important in the context of therapy where TCR turnover timescales (~ hours) are much faster than demonstrable efficacy timescales (days-months), i.e., internal capability is required to maintain the desired phenotype during the therapeutic period. This may e.g., be accomplished by different means as described infra, e.g., by engineering a T cell such that it does not express any functional TCR on its cell surface, or by engineering the T cell such that it does not express one or more of the subunits that comprise a functional TCR and therefore does not produce a functional TCR or by engineering a T cell such that it produces very little functional TCR on its surface, or which expresses a substantially impaired TCR, e.g by engineering the T cell to express mutated or truncated forms of one or more of the subunits that comprise the TCR, thereby rendering the T cell incapable of expressing a functional TCR or resulting in a cell that expresses a substantially impaired TCR. The different subunits that comprise a functional TCR are described infra. Whether a cell expresses a functional TCR may be determined using known assay methods such as are known in the art described herein. By a "substantially impaired TCR" applicants mean that this TCR will not substantially elicit an adverse immune reaction in a host, e.g., a GVHD reaction.

As described in detail infra, optionally these TCR-deficient cells may be engineered to comprise other mutations or transgenes that e.g., mutations or transgenes that affect T cell growth or proliferation, result in expression or absence of expression of a desired gene or gene construct, e.g., another receptor or a cytokine or other immunomodulatory or therapeutic polypeptide or a selectable marker such as a dominant selectable marker gene, e.g., DHFR or neomycin transferase.

"Allogeneic T cell" refers to a T cell from a donor having a tissue HLA type that matches the recipient. Typically, matching is performed on the basis of variability at three or more loci of the HLA gene, and a perfect match at these loci is preferred. In some instances allogeneic transplant donors may be related (usually a closely HLA matched sibling), syngeneic (a monozygotic 'identical' twin of the patient) or unrelated (donor who is not related and found to have very close degree of HLA matching). The HLA genes fall in two categories (Type I and Type II). In general, mismatches of the Type-I genes (i.e. HLA-A, HLA-B, or HLA-C) increase the risk of graft rejection. A mismatch of an HLA Type II gene (i.e. HLA-DR, or HLA-DQB1) increases the risk of graft-versus-host disease.

In the context of the present invention, a "bank of tissue matched TCR-deficient T cells" refers to different compositions each containing T cells of a specific HLA allotype which are rendered TCR-deficient according to the invention. Ideally this bank will comprise compositions containing T cells of a wide range of different HLA types that are representative of the human population. Such a bank of engineered TCR-deficient T cells will be useful as it will facilitate the availability of T cells suitable for use in different recipients such as cancer patients.

In the context of the present invention, a "therapeutically effective amount" is identified by one of skill in the art as being an amount of TCR-deficient T cells that, when administered to a patient, alleviates the signs and or symptoms of the disease (e.g., cancer, infection or GVHD). The actual amount to be administered can be determined based on studies done either in vitro or in vivo where the functional TCR-deficient T cells exhibit pharmacological activity against disease. For example, the functional TCR-deficient T cells may inhibit tumor cell growth either in vitro or in vivo and the amount of functional TCR-deficient T cells that inhibits such growth is identified as a therapeutically effective amount.

A "pharmaceutical composition" refers to a chemical or biological composition suitable for administration to a mammal. Such compositions may be specifically formulated for administration via one or more of a number of routes, including but not limited to buccal, intraarterial, intracardial, intracerebroventricular, intradermal, intramuscular, intraocular, intraperitoneal, intraspinal, intrathecal, intravenous, oral, parenteral, rectally via an enema or suppository, subcutaneous, subdermal, sublingual, transdermal, and transmucosal. In addition, administration can occur by means of injection, liquid, gel, drops, or other means of administration.

As used herein, a nucleic acid construct or nucleic acid sequence is intended to mean a DNA molecule which can be transformed or introduced into a T cell and be transcribed and translated to produce a product (e.g., a chimeric receptor or a suicide protein).

Nucleic acids are "operably linked" when placed into a functional relationship with another nucleic acid sequence. For example, DNA for a signal sequence is operably linked to DNA for a polypeptide if it is expressed as a preprotein that participates in the secretion of the polypeptide; a promoter or enhancer is operably linked to a coding sequence if it affects the transcription of the sequence. Generally, "operably linked" means that the DNA sequences being linked are contiguous, and, in the case of a secretory leader, contiguous and in reading frame. However, enhancers do not have to be contiguous. Linking is accomplished by ligation at convenient restriction sites or alternatively via a PCR/recombination method familiar to those skilled in the art (Gateway® Technology; Invitrogen, Carlsbad Calif.). If such sites do not exist, the synthetic oligonucleotide adapters or linkers are used in accordance with conventional practice.

The invention contemplates compositions and methods for reducing or ameliorating, or preventing or treating, diseases or conditions such as cancer, infectious disease, GVHD, transplantation rejection, one or more autoimmune disorders, or radiation sickness. In a non-limiting embodiment, the compositions are based on the concept of providing an allogeneic source of isolated human T cells, namely TCR-deficient T cells, that can be manufactured in advance of patient need and inexpensively. The ability to create a single therapeutic product at a single site using processes that are well controlled is attractive in terms of both cost and quality considerations. The change from an autologous to an allogeneic source for T cells offers significant advantages. For example, it has been estimated that a single healthy donor could supply T cells sufficient to treat dozens of patients after transduction and expansion.

According to the present invention, modified allogeneic T cells are produced that do not express functional T cell receptors (TCRs). It is to be understood that some, or even all, of the TCR subunits/dimers may be expressed on the cell surface, but that the T cell does not express enough functional TCR to induce an undesirable reaction in the host. Without functional TCRs on their surface, the allogeneic T cells fail to mount an undesired immune response to host cells. As a result, these TCR-deficient T cells fail to cause GVHD, for example, as they cannot recognize the host MHC molecules. Additionally, these TCR-deficient T cells can be engineered to simultaneously express functional, non-TCR, disease-specific receptors.

As is well known to one of skill in the art, various methods are readily available for isolating allogeneic T cells from a subject. For example, using cell surface marker expression or using commercially available kits (e.g., ISO-CELL™ from Pierce, Rockford, Ill.).

For cancer therapy, the approach encompasses producing an isolated pool of TCR-deficient T effector cells, e.g., of a desired tissue allotype that do not express a functional form of their endogenous TCR or which express substantially reduced levels of endogenous TCR compared to wild type T cells such that they do not elicit an immune response upon administration (such as GVHD), but instead express a functional, non-TCR receptor that recognizes tumor cells, or express another polypeptide that does not appreciably, or at all, attack non-disease associated cells, e.g., normal (non-tumorigenic) cells that do not express the antigen or ligand recognized by the tumor specific receptor or which express said antigen or ligand at reduced levels relative to tumor cells. It is understood by those skilled in the art that certain tumor-associated antigens are expressed in non-cancerous tissues, but they arc viable therapeutic targets in a tumor-bearing host. With respect thereto it is generally understood by those skilled in the art that certain non-TCR, tumor-specific receptors are expressed in non-cancerous tissues, but are viable therapeutic targets in a tumor-bearing host as they may be expressed at significantly reduced levels in normal than tumor cells.

While not necessary for most therapeutic usages of the subject TCR-deficient T cells, in some instances it may be desirable to remove some or all of the donor T cells from the host shortly after they have mediated their anti-tumor effect. This may be facilitated by engineering the T cells to express additional receptors or markers that facilitate their removal and/or identification in the host such as GFP and the like. While the present invention should substantially eliminate any possibility of GVHD or other adverse immune reaction in the recipient this may be desired in some individuals. This should not compromise efficacy as it has already been shown that donor T cells do not need to remain long in the host for a long-term anti-tumor effect to be initiated (Zhang, T., et al. 2007. Cancer Res. 67:11029-11036; Barber, A. et al. 2008. *J. Immunol.* 180:72-78).

In one embodiment of the invention, nucleic acid constructs introduced into engineered T cells further contains a suicide gene such as thymidine kinase (TK) of the HSV virus (herpesvirus) type I (Bonini, et al. (1997) Science 276:1719-1724), a Fas-based "artificial suicide gene" (Thomis, et al. (2001) Blood 97:1249-1257), or *E. coli* cytosine deaminase gene which are activated by gancyclovir, AP1903, or 5-fluorocytosine, respectively. The suicide gene is advantageously included in the nucleic acid construct of the present invention to provide for the opportunity to ablate the transduced T cells in case of toxicity and to destroy the chimeric construct once a tumor has been reduced or eliminated. The use of suicide genes for eliminating transformed or transduced cells is well-known in the art. For example, Bonini, et al. ((1997) Science 276:1719-1724) teach that donor lymphocytes transduced with the HSV-TK suicide gene provide antitumor activity in patients for up to one year and elimination of the transduced cells is achieved using ganciclovir. Further, Gonzalez, et al. ((2004) J. Gene Med. 6:704-711) describe the targeting of neuroblastoma with cytotoxic T lymphocyte clones genetically modified to express a chimeric scFvFc:zeta immunoreceptor specific for an epitope on L1-CAM, wherein the construct further expresses the hygromycin thymidine kinase (HyTK) suicide gene to eliminate the transgenic clones.

It is contemplated that the suicide gene can be expressed from the same promoter as the shRNA, minigene, or non-TCR receptor, or from a different promoter. Generally, however, nucleic acid sequences encoding the suicide protein and shRNA, minigene, or non-TCR receptor reside on the same construct or vector. Expression of the suicide gene from the same promoter as the shRNA, minigene, or non-TCR receptor can be accomplished using any well-known internal ribosome entry site (IRES). Suitable IRES sequences which can be used in the nucleic acid construct of the present invention include, but are not limited to, IRES from EMCV, c-myc, FGF-2, poliovirus and HTLV-1. By way of illustration only, a nucleic acid construct for expressing a chimeric receptor can have the following structure: promoter→chimeric receptor→1RES→suicidal gene. Alternatively, the suicide gene can be expressed from a different promoter than that of the chimeric receptor (e.g., promoter 1→chimeric receptor→promoter 2→suicidal gene).

Because of the broad application of T cells for cell therapies, and the improved nature of the T cells of the invention, the present invention encompasses any method or composition wherein T cells are therapeutically desirable. Such compositions and methods include those for reducing or ameliorating, or preventing or treating cancer, GVHD, transplantation rejection, infection, one or more autoimmune disorders, radiation sickness, or other diseases or conditions that are based on the use of T cells derived from an allogeneic source that lack expression of functional TCR.

As indicated, further embodiments of the invention embrace recombinant expression of receptors in said TCR-deficient T cells, such as chimeric NKG2D, chimeric Fv domains, NKG2D, or any other receptor to initiate signals to T cells, thereby creating potent, specific effector T cells. One of skill in the art can select the appropriate receptor to be expressed by the TCR-deficient T cell based on the disease to be treated. For example, receptors that can be expressed by the TCR-deficient T cell for treatment of cancer would include any receptor to a ligand that has been identified on cancer cells. Such receptors include, but are not limited to, NKG2D, NKG2A, NKG2C, NKG2F, LLT1, AICL, CD26, NKRP1, NKp30, NKp44, NKp46, CD244 (2B4), DNAM-1, and NKp80.

In another embodiment of the invention, such receptors include, but are not limited to, chimeric receptors comprising a ligand binding domain obtained from NKG2D, NKG2A, NKG2C, NKG2F, LLT1, AICL, CD26, NKRP1, NKp30, NKp44, NKp46, CD244 (2B4), DNAM-1, and NKp80, or an anti-tumor antibody such as anti-Her2neu or anti-EGFR, and a signaling domain obtained from CD3-zeta, Dap10, CD28, 41BB, and CD40L. In one embodiment of the invention, the chimeric receptor binds MIC-A, MIC-B, Her2neu, EGFR, mesothelin, CD38, CD20, CD19, PSA, MUC1, MUC2, MUC3A, MUC3B, MUC4, MUC5AC, MUC5B, MUC6, MUC7, MUC8, MUC12, MUC13, MUC15, MUC16, MUC17, MUC19, MUC20, estrogen receptor, progesterone receptor, RON, or one or more members of the ULBP/RAET1 family including ULBP1, ULBP2, ULBP3, ULBP4, ULBP5, and ULBP6.

In the methods of the present invention a patient suffering from cancer, GVHD, transplantation rejection, infection, one or more autoimmune disorders, or radiation sickness is administered a therapeutically effective amount of a composition comprising said TCR-deficient T cells. In another embodiment of the invention, a therapeutically effective amount of a composition comprising said TCR-deficient T cells is administered to prevent, treat, or reduce GVHD, transplantation rejection, or cancer.

Methods of Producing TCR-Deficient T-Cells

T cells stably lacking expression of a functional TCR according to the invention may be produced using a variety of approaches. T cells internalize, sort, and degrade the entire T cell receptor as a complex, with a half-life of about 10 hours in resting T cells and 3 hours in stimulated T cells (von Essen, M. et al. 2004. J. Immunol. 173:384-393). Proper functioning of the TCR complex requires the proper stoichiometric ratio of the proteins that compose the TCR complex. TCR function also requires two functioning TCR zeta proteins with ITAM motifs. The activation of the TCR upon engagement of its MHC-peptide ligand requires the engagement of several TCRs on the same T cell, which all must signal properly. Thus, if a TCR complex is destabilized with proteins that do not associate properly or cannot signal optimally, the T cell will not become activated sufficiently to begin a cellular response.

In one embodiment of the invention, TCR expression is eliminated using small-hairpin RNAs (shRNAs) that target nucleic acids encoding specific TCRs (e.g., TCR-α and TCR-β) and/or CD3 chains in primary T cells. By blocking expression of one or more of these proteins, the T cell will no longer produce one or more of the key components of the TCR complex, thereby destabilizing the TCR complex and preventing cell surface expression of a functional TCR. Even though some TCR complexes can be recycled to the cell surface, the shRNA will prevent new production of TCR proteins resulting in degradation and removal of the entire TCR complex, resulting in the production of a T cell having a stable deficiency in functional TCR expression.

Expression of shRNAs in primary T cells can be achieved using any conventional expression system, e.g., a lentiviral expression system. Although lentiviruses are useful for targeting resting primary T cells, not all T cells will express the shRNAs. Some of these T cells may not express sufficient amounts of the shRNAs to allow enough inhibition of TCR expression to alter the functional activity of the T cell. Thus, T cells that retain moderate to high TCR expression after viral transduction can be removed, e.g., by cell sorting or separation techniques, so that the remaining T cells are deficient in cell surface TCR or CD3, enabling the expansion of an isolated population of T cells deficient in expression of functional TCR or CD3.

In a non-limiting embodiment of the invention, exemplary targeting shRNAs have been designed for key components of the TCR complex as set forth below (Table 1).

TABLE 1

| Target | Target base | shRNA Sequence | GC % | SEQ ID NO: |
|---|---|---|---|---|
| TCR-β | 18[a] | AGTGCGAGGAGATTCGGCAGCTTAT | 52 | 1 |
|  | 21[a] | GCGAGGAGATTCGGCAGCTTATTTC | 52 | 2 |
|  | 48[a] | CCACCATCCTCTATGAGATCTTGCT | 48 | 3 |
|  | 54[a] | TCCTCTATGAGATCTTGCTAGGGAA | 44 | 4 |
| TCR-α | 3[b] | TCTATGGCTTCAACTGGCTAGGGTG | 52 | 5 |
|  | 76[b] | CAGGTAGAGGCCTTGTCCACCTAAT | 52 | 6 |
|  | 01[b] | GCAGCAGACACTGCTTCTTACTTCT | 48 | 7 |
|  | 07[b] | GACACTGCTTCTTACTTCTGTGCTA | 44 | 8 |
| CD3-ε | 89[c] | CCTCTGCCTCTTATCAGTTGGCGTT | 52 | 9 |
|  | 27[c] | GAGCAAAGTGGTTATTATGTCTGCT | 40 | 10 |
|  | 62[c] | AAGCAAACCAGAAGATGCGAACTTT | 40 | 11 |
|  | 45 | GACCTGTATTCTGGCCTGAATCAGA | 48 | 12 |
|  |  | GGCCTCTGCCTCTTATCAGTT | 52 | 13 |
|  |  | GCCTCTGCCTCTTATCAGTTG | 52 | 14 |
|  |  | GCCTCTTATCAGTTGGCGTTT | 48 | 15 |
|  |  | AGGATCACCTGTCACTGAAGG | 52 | 16 |
|  |  | GGATCACCTGTCACTGAAGGA | 52 | 17 |
|  |  | GAATTGGAGCAAAGTGGTTAT | 38 | 18 |
|  |  | GGAGCAAAGTGGTTATTATGT | 38 | 19 |
|  |  | GCAAACCAGAAGATGCGAACT | 48 | 20 |
|  |  | ACCTGTATTCTGGCCTGAATC | 48 | 21 |
|  |  | GCCTGAATCAGAGACGCATCT | 52 | 22 |
|  |  | CTGAAATACTATGGCAACACAAT-GATAAA | 31 | 23 |
|  |  | AAACATAGGCAGTGATGAGGATC-ACCTGT | 45 | 24 |
|  |  | ATTGTCATAGTGGACATCTGCATC-ACTGG | 45 | 25 |
|  |  | CTGTATTCTGGCCTGAATCAGAGA-CGCAT | 48 | 26 |
| CD3-δ[d] |  | GATACCTATAGAGGAACTTGA | 38 | 27 |
|  |  | GACAGAGTGTTTGTGAATTGC | 43 | 28 |
|  |  | GAACACTGCTCTCAGACATTA | 43 | 29 |
|  |  | GGACCCACGAGGAATATATAG | 48 | 30 |
|  |  | GGTGTAATGGGACAGATATAT | 38 | 31 |
|  |  | GCAAGTTCATTATCGAATGTG | 38 | 32 |
|  |  | GGCTGGCATCATTGTCACTGA | 52 | 33 |
|  |  | GCTGGCATCATTGTCACTGAT | 48 | 34 |
|  |  | GCATCATTGTCACTGATGTCA | 43 | 35 |
|  |  | GCTTTGGGAGTCTTCTGCTTT | 48 | 36 |
|  |  | TGGAACATAGCACGTTTCTCTCTG-GCCTG | 52 | 37 |
|  |  | CTGCTCTCAGACATTACAAGACTG-GACCT | 48 | 38 |
|  |  | ACCGTGGCTGGCATCATTGTCACT-GATGT | 52 | 39 |
|  |  | TGATGCTCAGTACAGCCACCTTGG-AGGAA | 52 | 40 |
| CD3-γ[e] |  | GGCTATCATTCTTCTTCAAGG | 43 | 41 |
|  |  | GCCCAGTCAATCAAAGGAAAC | 48 | 42 |
|  |  | GGTTAAGGTGTATGACTATCA | 38 | 43 |
|  |  | GGTTCGGTACTTCTGACTTGT | 48 | 44 |
|  |  | GAATGTGTCAGAACTGCATTG | 43 | 45 |
|  |  | GCAGCCACCATATCTGGCTTT | 52 | 46 |
|  |  | GGCTTTCTCTTTGCTGAAATC | 43 | 47 |
|  |  | GCTTTCTCTTTGCTGAAATCG | 43 | 48 |
|  |  | GCCACCTTCAAGGAAACCAGT | 52 | 49 |
|  |  | GAAACCAGTTGAGGAGGAATT | 43 | 50 |
|  |  | GGCTTTCTCTTTGCTGAAATCGTCA-GCAT | 45 | 51 |
|  |  | AGGATGGAGTTCGCCAGTCGAGAG-CTTCA | 55 | 52 |
|  |  | CCTCAAGGATCGAGAAGATGACCA-GTACA | 48 | 53 |
|  |  | TACAGCCACCTTCAAGGAAACCAG-TTGAG | 48 | 54 |

[a]With reference to Accession No. EU030678.
[b]With reference to Accession No. AY247834.
[c]With reference to Accession No. NM_000733.
[d]With reference to Accession No. NM_000732.
[e]With reference to Accession No. NM_000073.

TCR-alpha, TCR-beta, TCR-gamma, TCR-delta, CD3-gamma, CD3-delta, CD3-epsilon, or CD3-zeta mRNAs can be targeted separately or together using a variety of targeting shRNAs. The TCR-β and TCR-α chains are composed of variable and constant portions. Several targeting shRNAs have been designed for the constant portions of these TCR/CD3 sequences. One or a combination of shRNAs can be used for each molecular target to identify the most efficient inhibitor of TCR expression. Using established protocols, each shRNA construct is cloned into, e.g., a pLko.1 plasmid, with expression controlled by a promoter routinely used in the art, e.g., the U6p promoter. The resulting construct can be screened and confirmed for accuracy by sequencing. The shRNA expression plasmid can then be transfected into any suitable host cell (e.g., 293T), together with a packaging plasmid and an envelope plasmid for packaging. Primary human peripheral blood mononuclear cells (PBMCs) are isolated from healthy donors and activated with low dose soluble anti-CD3 and 25 U/ml rhuIL-2 for 48 hours. Although it is not required to activate T cells for lentiviral transduction, transduction works more efficiently and allows the cells to continue to expand in IL-2. The activated cells are washed and transduced, e.g., using a 1 hour spin-fection at 30° C., followed by a 7 hour resting period.

In another embodiment of the invention, over-expression of a dominant-negative inhibitor protein is capable of interrupting TCR expression or function. In this embodiment of the invention, a minigene that incorporates part, or all, of a polynucleotide encoding for one of the TCR components (e.g., TCR-alpha, TCR-beta, CD3-gamma, CD3-delta, CD3-epsilon, or CD3-zeta) is prepared, but is modified so that: (1) it lacks key signaling motifs (e.g. an ITAM) required for protein function; (2) is modified so it does not associate properly with its other natural TCR components; or (3) can associate properly but does not bind ligands (e.g. a truncated TCR beta minigene).

These minigenes may also encode a portion of a protein that serves as a means to identify the over-expressed minigene. For example, polynucleotides encoding a truncated CD19 protein, which contains the binding site for anti-CD19 mAbs, can be operably linked to the minigene so that the resulting cell that expresses the minigene will express the encoded protein and can be identified with anti-CD19 mAbs. This identification enables one to determine the extent of minigene expression and isolate cells expressing this protein (and thus lack a functional TCR).

In one embodiment of the invention, over-expression of a minigene lacking a signaling motif(s) lead to a TCR complex that cannot signal properly when the TCR is engaged by its MHC-peptide ligand on an opposing cell. In a non-limiting embodiment of the invention, high expression of this minigene (and the encoded polypeptide) outcompetes the natural complete protein when the TCR components associate, resulting in a TCR complex that cannot signal. In another embodiment of the invention, the minigene comprises, or alternatively consists of, a polynucleotide encoding full or partial CD3-zeta, CD3-gamma, CD3-delta, or CD3-epsilon polypeptides lacking the ITAM motifs required for signaling. The CD3-zeta protein contains three ITAM motifs in the cytoplasmic portion, and in one embodiment of the invention, removal of all of these through truncation inhibits proper TCR signaling in any complexes where this modified protein is incorporated. The construct may incorporate ITIM or other signaling motifs, which are known to alter cell signaling and promote inhibitory signals through the recruitment of phosphatases such as SHP1 and SHP2.

In another embodiment of the invention, over-expression of a minigene is modified so that the encoded polypeptide can associate with some, but not all, of its natural partners, creating competition with the normal protein for those associating proteins. In another non-limiting hypothesis of the invention, high level expression of the minigene (and the encoded polypeptide) outcompetes the natural partner proteins and prevents assembly of a functional TCR complex, which requires all components to associate in the proper ratios and protein-protein interactions. In another embodiment of the invention, minigenes comprise, or alternatively consist of, all or part of the polynucleotides encoding full-length proteins (e.g., TCR-alpha, TCR-beta, CD3-gamma, CD3-delta, CD3-epsilon, or CD3-zeta), but containing selected deletions in the sequence coding for amino acids in the transmembrane portion of the protein that are known to be required for assembly with other TCR/CD3 proteins.

In a preferred embodiment of the invention, selected deletions in the sequence coding for amino acids in the transmembrane portion of the protein known to be required for assembly with other TCR/CD3 proteins include, but are not limited to: the arginine residue at position 5 in the TCR-alpha transmembrane region; the lysine residue at position 10 in the TCR-alpha transmembrane region; the lysine residue at position 9 in the TCR-beta transmembrane region; the glutamic acid residue in the transmembrane region of CD3-gamma; the aspartic acid residue in the transmembrane region of CD3-delta-epsilon; the aspartic acid residue in the transmembrane region of CD3-epsilon; and the aspartic acid residue in the transmembrane region of CD3-zeta.

Over-expression of a truncated TCR-alpha, TCR-beta, TCR-gamma, or TCR-delta protein results in a TCR complex that cannot bind to MHC-peptide ligands, and thus will not function to activate the T cell. In another embodiment of the invention, minigenes comprise, or alternatively consist of, polynucleotides encoding the entire cytoplasmic and transmembrane portions of these proteins and portions of the extracellular region, but lacks polynucleotides encoding all or part of the first extracellular domain (i.e., the most outer domain containing the ligand binding site). In a preferred embodiment, said minigene polynucleotides do not encode Valpha and Vbeta polypeptides of the TCR-alpha and TCR-beta chains. In one embodiment, the minigene polynucleotides may be operably linked to polynucleotides encoding a protein epitope tag (e.g. CD19), thereby allowing mAb identification of cells expressing these genes.

In another embodiment, these minigenes can be expressed using a strong viral promoter, such as the 5'LTR of a retrovirus, or a CMV or SV40 promoter. Typically, this promoter is immediately upstream of the minigene and leads to a high expression of the minigene mRNA. In another embodiment, the construct encodes a second polynucleotide sequence under the same promoter (using for example an IRES DNA sequence between) or another promoter. This second polynucleotide sequence may encode for a functional non-TCR receptor providing specificity for the T cell. Examples of this polynucleotide include, but are not limited to, chimeric NKG2D, chimeric NKp30, chimeric NKp46, or chimeric anti-Her2neu. In a further embodiment, promoter-minigenes are constructed into a retroviral or other suitable expression plasmid and transfected or transduced directly into T cells using standard methods (Zhang, T. et al., (2006) Cancer Res., 66(11) 5927-5933; Barber, A. et al., (2007) Cancer Res., 67(10):5003-5008).

After viral transduction and expansion using any of the methods discussed previously, any T cells that still express TCR/CD3 are removed using anti-CD3 mAbs and magnetic beads using Miltenyi selection columns as previously described (Barber, A. et al., (2007) Cancer Res., 67(10): 5003-5008). The T cells are subsequently washed and cultured in IL-2 (25 U/ml) for 3 to 7 days to allow expansion of the effector cells in a similar manner as for use of the cells in vivo.

The expression of TCR $\alpha\beta$ and CD3 can be evaluated by flow cytometry and quantitative real-time PCR (QRT-PCR). Expression of TCR-$\alpha$, TCR-$\beta$, CD3$\varepsilon$, CD3-$\zeta$, and GAPDH (as a control) mRNA can be analyzed by QRT-PCR using an ABI7300 real-time PCR instrument and gene-specific TAQMAN® primers using methods similar to those used in Sentman, C. L. et al. ((2004) J. Immunol. 173:6760-6766). Changes in cell surface expression can be determined using antibodies specific for TCR-$\alpha$, TCR-$\beta$, CD3$\varepsilon$, CD8, CD4, CD5, and CD45.

It is possible that a single shRNA species may not sufficiently inhibit TCR expression on the cell surface. In this case, multiple TCR shRNAs may be used simultaneously to target multiple components of the TCR complex. Each component is required for TCR complex assembly at the cell surface, so a loss of one of these proteins can result in loss of TCR expression at the cell surface. While some or even all TCR expression may remain, it is the receptor function which determines whether the receptor induces an immune response. The functional deficiency, rather than complete cell surface absence, is the critical measure. In general, the lower the TCR expression, the less likely sufficient TCR cross-linking can occur to lead to T cell activation via the TCR complex. While particular embodiments embrace the targeting of TCR-alpha, TCR-beta, and CD3-epsilon, other components of the TCR complex, such as CD3-gamma, CD3-delta, or CD3-zeta, can also be targeted.

The primary aim of removing the TCR from the cell surface is to prevent the activation of the T cell to incompatible MHC alleles. To determine whether the reduction in TCR expression with each shRNA or minigene construct is sufficient to alter T cell function, the T cells can be tested for: (1) cell survival in vitro; (2) proliferation in the presence of mitomycin C-treated allogeneic PBMCs; and (3) cytokine production in response to allogeneic PBMCs, anti-CD3 mAbs, or anti-TCR mAbs.

To test cell survival, transduced T cells are propagated in complete RPMI medium with rhuIL-2 (25 U/ml). Cells are plated at similar densities at the start of culture and a sample may be removed for cell counting and viability daily for 7 or more days. To determine whether the T cells express sufficient TCR to induce a response against allogeneic cells, transduced or control T cells are cultured with mitomycin C-treated allogeneic or syngeneic PBMCs. The T cells are preloaded with CFSE, which is a cell permeable dye that divides equally between daughter cells after division. The extent of cell division can be readily determined by flow cytometry. Another hallmark of T cell activation is production of cytokines. To determine whether each shRNA construct inhibits T cell function, transduced T cells are cultured with anti-CD3 mAbs (25 ng/ml). After 24 hours, cell-free supernatants are collected and the amount of IL-2 and IFN-$\gamma$ produced is quantified by ELISA. PMA/ionomycin are used as a positive control to stimulate the T cells and T cells alone are used as a negative control.

It is possible that removal of TCR-alpha or TCR-beta components may allow the preferential expansion of TCR-gamma/delta T cells. These T cells are quite rare in the blood, however the presence of these cells can be determined with anti-TCR-gamma/delta antibodies. If there is an outgrowth of these cells, the targeting of CD3-epsilon, which is required for cell surface expression of both TCR-alpha/beta and TCR-gamma/delta at the cell surface, can be used. Both IL-2 and IFN-γ are key effector cytokines that drive T cell expansion and macrophage activation. Therefore, lack of production of these cytokines is a sign of functional inactivation. It is also possible to measure changes in other cytokines, such as TNF-α. Any reduction in T cell survival upon elimination of TCR expression can be determined by culturing the TCR-deficient T cells with PBMCs, which better reflects the in vivo environment and provides support for T cell survival.

In another embodiment of the invention, The T cells stably deficient in functional TCR expression express a functional, non-TCR receptor. In this embodiment, the removal of TCR function (as described previously) is further combined with expression of one or more exogenous non-TCR targeting receptors (such as for example chimeric NKG2D (chNKG2D) or Fv molecules). This embodiment provides "universal" cell products, which can be stored for future therapy of any patient with any type of cancer, provided a suitable targeting receptor is employed.

Further embodiments of the invention embrace recombinant expression of receptors in said TCR-deficient T cells, such as chNKG2D, chimeric Fv domains, NKG2D, or any other receptor to initiate signals to T cells, thereby creating potent, specific effector T cells. One of skill in the art can select the appropriate receptor to be expressed by the TCR-deficient T cell based on the disease to be treated. For example, receptors that can be expressed by the TCR-deficient T cell for treatment of cancer would include any receptor to a ligand that has been identified on cancer cells. Such receptors include, but are not limited to, NKG2D (GENBANK accession number BC039836), NKG2A (GENBANK accession number AF461812), NKG2C (GENBANK accession number AJ001684), NKG2F, LLT1, AICL, CD26, NKRP1, NKp30 (e.g., GENBANK accession number AB055881), NKp44 (e.g., GENBANK accession number AJ225109), NKp46 (e.g., GENBANK accession number AJ001383), CD244 (2B4), DNAM-1, and NKp80.

In another embodiment of the invention, such receptors include, but not limited to, chimeric receptors comprising a ligand binding domain obtained from NKG2D, NKG2A, NKG2C, NKG2F, LLT1, AICL, CD26, NKRP1, NKp30, NKp44, NKp46, CD244 (2B4), DNAM-1, and NKp80, or an anti-tumor antibody, such as anti-Her2neu and anti-EGFR, and a signaling domain obtained from CD3-zeta (CD3ζ) (e.g., GENBANK accession number human NM_198053), Dap10 (e.g., GENBANK accession number AF072845), CD28, 41BB, and/or CD40L.

In a further embodiment of the invention, the chimeric receptor binds MIC-A, MIC-B, Her2neu, EGFR, mesothelin, CD38, CD20, CD19, PSA, MUC1, MUC2, MUC3A, MUC3B, MUC4, MUC5AC, MUC5B, MUC6, MUC7, MUC8, MUC12, MUC13, MUC15, MUC16, MUC17, MUC19, MUC20, estrogen receptor, progesterone receptor, RON, or one or more members of the ULBP/RAET1 family including ULBP1, ULBP2, ULBP3, ULBP4, ULBP5, and ULBP6.

By way of illustration only, shRNAs or minigenes shown to eliminate cell surface expression of the TCR complex are co-expressed with the chNKG2D receptor via one or more viral vectors. To achieve co-expression in one vector, the shRNA can be driven by a U6 promoter and the chNKG2D receptor by a PGK promoter. In another embodiment, if an IRES sequence is used to separate the genetic elements then only one promoter is used.

A C-type lectin-like NK cell receptor protein particularly suitable for use in the chimeric receptor includes a receptor expressed on the surface of natural killer cells, wherein upon binding to its cognate ligand(s) it alters NK cell activation. The receptor can work alone or in concert with other molecules. Ligands for these receptors are generally expressed on the surface of one or more tumor cell types, e.g., tumors associated with cancers of the colon, lung, breast, kidney, ovary, cervix, and prostate; melanomas; myelomas; leukemias; and lymphomas (Wu, et al. (2004) J. Clin. Invest. 114:60-568; Groh, et al. (1999) Proc. Natl. Acad. Sci. USA 96:6879-6884; Pende, et al. (2001) Eur. J. Immunol. 31:1076-1086) and are not widely expressed on the surface of cells of normal tissues.

Examples of such ligands include, but are not limited to, MIC-A, MIC-B, heat shock proteins, ULBP binding proteins (e.g., ULPBs 1-4), and non-classical HLA molecules such as HLA-E and HLA-G, whereas classical MHC molecules such as HLA-A, HLA-B, or HLA-C and alleles thereof are not generally considered strong ligands of the C-type lectin-like NK cell receptor protein of the present invention. C-type lectin-like NK cell receptors which bind these ligands generally have a type II protein structure, wherein the N-terminal end of the protein is intracellular. In addition to any NK cell receptors previously listed above, further exemplary NK cell receptors of this type include, but are not limited to, Dectin-1 (GENBANK accession number AJ312373 or AJ312372), Mast cell function-associated antigen (GENBANK accession number AF097358), HNKR-P1A (GENBANK accession number U11276), LLT1 (GENBANK accession number AF133299), CD69 (GENBANK accession number NM_001781), CD69 homolog, CD72 (GENBANK accession number NM_001782), CD94 (GENBANK accession number NM_002262 or NM_007334), KLRF1 (GENBANK accession number NM_016523), Oxidised LDL receptor (GENBANK accession number NM_002543), CLEC-1, CLEC-2 (GENBANK accession number NM_016509), NKG2D (GENBANK accession number BC039836), NKG2C (GENBANK accession number AJ001684), NKG2A (GENBANK accession number AF461812), NKG2E (GENBANK accession number AF461157), WUGSC:H_DJ0701016.2, or Myeloid DAP12-associating lectin (MDL-1; GENBANK accession number AJ271684). In a preferred embodiment of the invention, the NK cell receptor is human NKG2D (SEQ ID NO:58) or human NKG2C (SEQ ID NO:59).

Similar type I receptors which would be useful in the chimeric receptor include NKp46 (GENBANK accession number AJ001383), NKp30 (GENBANK accession number AB055881), or NKp44 (GENBANK accession number AJ225109).

As an alternative to the C-type lectin-like NK cell receptor protein, a protein associated with a C-type lectin-like NK cell receptor protein can be used in the chimeric receptor protein. In general, proteins associated with C-type lectin-like NK cell receptor are defined as proteins that interact with the receptor and transduce signals therefrom. Suitable human proteins which function in this manner further include, but are not limited to, DAP10 (e.g., GENBANK accession number AF072845)(SEQ ID NO:60), DAP12 (e.g., GENBANK accession number AF019562)(SEQ ID NO:61) and FcR gamma.

To the N-terminus of the C-type lectin-like NK cell receptor is fused an immune signaling receptor having an immunoreceptor tyrosine-based activation motif (ITAM), (Asp/Glu)-Xaa-Xaa-Tyr*-Xaa-Xaa-(Ile/Leu)-Xaa$_{6-8}$-Tyr*-Xaa-Xaa-(Ile/Leu) (SEQ ID NOS: 55-57) which is involved in the activation of cellular responses via immune receptors. Similarly, when employing a protein associated with a C-type lectin-like NK cell receptor, an immune signaling receptor can be fused to the C-terminus of said protein (FIG. 1). Suitable immune signaling receptors for use in the chimeric receptor of the present invention include, but are not limited to, the zeta chain of the T-cell receptor, the eta chain which differs from the zeta chain only in its most C-terminal exon as a result of alternative splicing of the zeta mRNA, the delta, gamma and epsilon chains of the T-cell receptor (CD3 chains) and the gamma subunit of the FcR1 receptor. In particular embodiments, in addition to immune signaling receptors identified previously, the immune signaling receptor is CD3-zeta (CD3) (e.g., GENBANK accession number human NM_198053)(SEQ ID NO:62), or human Fc epsilon receptor-gamma chain (e.g., GENBANK accession number M33195)(SEQ ID NO:63) or the cytoplasmic domain or a splicing variant thereof.

In particular embodiments, a chimeric receptor of the present invention is a fusion between NKG2D and CD3-zeta, or Dap10 and CD3-zeta.

In the nucleic acid construct of the present invention, the promoter is operably linked to the nucleic acid sequence encoding the chimeric receptor of the present invention, i.e., they are positioned so as to promote transcription of the messenger RNA from the DNA encoding the chimeric receptor. The promoter can be of genomic origin or synthetically generated. A variety of promoters for use in T cells are well-known in the art (e.g., the CD4 promoter disclosed by Marodon, et al. (2003) Blood 101(9):3416-23). The promoter can be constitutive or inducible, where induction is associated with the specific cell type or a specific level of maturation. Alternatively, a number of well-known viral promoters are also suitable. Promoters of interest include the β-actin promoter, SV40 early and late promoters, immunoglobulin promoter, human cytomegalovirus promoter, retrovirus promoter, and the Friend spleen focus-forming virus promoter. The promoters may or may not be associated with enhancers, wherein the enhancers may be naturally associated with the particular promoter or associated with a different promoter.

The sequence of the open reading frame encoding the chimeric receptor can be obtained from a genomic DNA source, a cDNA source, or can be synthesized (e.g., via PCR), or combinations thereof. Depending upon the size of the genomic DNA and the number of introns, it may be desirable to use cDNA or a combination thereof as it is found that introns stabilize the mRNA or provide T cell-specific expression (Barthel and Goldfeld (2003) J. Immunol. 171 (7):3612-9). Also, it may be further advantageous to use endogenous or exogenous non-coding regions to stabilize the mRNA.

For expression of a chimeric receptor of the present invention, the naturally occurring or endogenous transcriptional initiation region of the nucleic acid sequence encoding N-terminal component of the chimeric receptor can be used to generate the chimeric receptor in the target host. Alternatively, an exogenous transcriptional initiation region can be used which allows for constitutive or inducible expression, wherein expression can be controlled depending upon the target host, the level of expression desired, the nature of the target host, and the like.

Likewise, the signal sequence directing the chimeric receptor to the surface membrane can be the endogenous signal sequence of N-terminal component of the chimeric receptor. Optionally, in some instances, it may be desirable to exchange this sequence for a different signal sequence. However, the signal sequence selected should be compatible with the secretory pathway of T cells so that the chimeric receptor is presented on the surface of the T cell.

Similarly, a termination region can be provided by the naturally occurring or endogenous transcriptional termination region of the nucleic acid sequence encoding the C-terminal component of the chimeric receptor. Alternatively, the termination region can be derived from a different source. For the most part, the source of the termination region is generally not considered to be critical to the expression of a recombinant protein and a wide variety of termination regions can be employed without adversely affecting expression.

As will be appreciated by one of skill in the art, in some instances, a few amino acids at the ends of the C-type lectin-like natural killer cell receptor (or protein associated therewith) or immune signaling receptor can be deleted, usually not more than 10, more usually not more than 5 residues. Also, it may be desirable to introduce a small number of amino acids at the borders, usually not more than 10, more usually not more than 5 residues. The deletion or insertion of amino acids will usually be as a result of the needs of the construction, providing for convenient restriction sites, ease of manipulation, improvement in levels of expression, or the like. In addition, the substitute of one or more amino acids with a different amino acid can occur for similar reasons, usually not substituting more than about five amino acids in any one domain.

The chimeric construct, which encodes the chimeric receptor can be prepared in conventional ways. Since, for the most part, natural sequences are employed, the natural genes are isolated and manipulated, as appropriate (e.g., when employing a Type II receptor, the immune signaling receptor component may have to be inverted), so as to allow for the proper joining of the various components. Thus, the nucleic acid sequences encoding for the N-terminal and C-terminal proteins of the chimeric receptor can be isolated by employing the polymerase chain reaction (PCR), using appropriate primers which result in deletion of the undesired portions of the gene. Alternatively, restriction digests of cloned genes can be used to generate the chimeric construct. In either case, the sequences can be selected to provide for restriction sites which are blunt-ended, or have complementary overlaps.

The various manipulations for preparing the chimeric construct can be carried out in vitro and in particular embodiments the chimeric construct is introduced into vectors for cloning and expression in an appropriate host using standard transformation or transfection methods. Thus, after each manipulation, the resulting construct from joining of the DNA sequences is cloned, the vector isolated, and the sequence screened to insure that the sequence encodes the desired chimeric receptor. The sequence can be screened by restriction analysis, sequencing, or the like.

It is contemplated that the chimeric construct can be introduced into T cells as naked DNA or in a suitable vector. Methods of stably transfecting T cells by electroporation using naked DNA are known in the art. See, e.g., U.S. Pat. No. 6,410,319. Naked DNA generally refers to the DNA encoding a chimeric receptor of the present invention contained in a plasmid expression vector in proper orientation for expression. Advantageously, the use of naked DNA reduces the time required to produce T cells expressing the chimeric receptor of the present invention.

Alternatively, a viral vector (e.g., a retroviral vector, adenoviral vector, adeno-associated viral vector, or lentiviral vector) can be used to introduce the chimeric construct into T cells. Suitable vectors for use in accordance with the method of the present invention are non-replicating in the subject's T cells. A large number of vectors are known which are based on viruses, where the copy number of the virus maintained in the cell is low enough to maintain the viability of the cell. Illustrative vectors include the pFB-neo vectors (STRATAGENE™) as well as vectors based on HIV, SV40, EBV, HSV or BPV. Once it is established that the transfected or transduced T cell is capable of expressing the chimeric receptor as a surface membrane protein with the desired regulation and at a desired level, it can be determined whether the chimeric receptor is functional in the host cell to provide for the desired signal induction (e.g., production of Rantes, Mipl-alpha, GM-CSF upon stimulation with the appropriate ligand).

As described above, primary human PBMCs are isolated from healthy donors and activated with low-dose soluble anti-CD3 and rhuIL-2, anti-CD3/anti-CD28 beads and rhuIL-2, or irradiated antigen presenting cells and rhuIL-2. Although it is not required to activate T cells for lentiviral transduction, transduction is more efficient and the cells continue to expand in IL-2. The activated cells are washed and transduced as described herein, followed by a resting period. The cells are washed and cultured in IL-2 for 3 to 7 days to allow expansion of the effector cells in a similar manner as for use of the cells in vivo.

The expression of TCRαβ, CD3, and NKG2D can be evaluated by flow cytometry and quantitative QRT-PCR as discussed herein. The number of CD4+ and CD8+ T cells can also be determined. Overall cell numbers and the percentage of TCR complex-deficient, TCR-competent, and chNKG2D-expressing T cells can be determined by flow cytometry. These numbers can be compared to PBMCs that have been transduced with the shRNA or chNKG2D genes alone (as controls). Vector-only transduced cells can also be included as controls.

After viral transduction and expansion, the TCR+ and TCR− cells can be separated by mAbs with magnetic beads over Miltenyi columns and TCR-deficient T cells expressing the chNKG2D receptor are identified and isolated. For example, chNKG2D expression can be verified by QRT-PCR using specific primers for the chNKG2D receptor (Zhang, T. et al. (2007) Cancer Res. 67:11029-11036; Barber, A. et al. (2008) J. Immunol. 180:72-78). Function of these TCR-deficient chNKG2D+cells can be determined by culturing the cells with allogeneic PBMCs or tumor cells that express NKG2D ligands. T cell proliferation and cytokine production (IFN-γ and IL-2) can be determined by flow cytometry and ELISA, respectively. To determine whether the T cells that have lost TCR function and retained chNKG2D function, transduced or control T cells will be cultured with anti-CD3 (25 ng/ml) or mitomycin C-treated allogeneic PBMCs, or syngeneic PBMCs. The extent of cytokine production (IFN-γ and IL-2) can be determined by ELISA. The T cells can be preloaded with CFSE, which is a cell permeable dye that divides equally between daughter cells after division. The extent of cell division can be readily determined by flow cytometry.

Another hallmark of T cell activation is production of cytokines. To determine whether TCR-deficient chNKG2D+ cells induce T cell activation, the T cells are cocultured with mitomycin C-treated allogeneic PBMCs, syngeneic PBMCs, or tumor cells: P815-MICA (a murine tumor expressing human MICA, a ligand for NKG2D), P815, A2008 (a human ovarian tumor cell, NKG2D ligand+), and U266 (a human myeloma cell line, NKG2D ligand+). After 24 hours, cell-free supernatants are collected and the amount of IL-2 and IFN-γ produced is quantified by ELISA. T cells alone and culture with syngeneic PBMCs are used as a negative control.

Subsequently, the transduced T cells are reintroduced or administered to the subject to activate anti-tumor responses in said subject. To facilitate administration, the transduced T cells according to the invention can be made into a pharmaceutical composition or made implant appropriate for administration in vivo, with appropriate carriers or diluents, which further can be pharmaceutically acceptable. The means of making such a composition or an implant have been described in the art (see, for instance, Remington's Pharmaceutical Sciences, 16th Ed., Mack, ed. (1980)). Where appropriate, the transduced T cells can be formulated into a preparation in semisolid or liquid form, such as a capsule, solution, injection, inhalant, or aerosol, in the usual ways for their respective route of administration. Means known in the art can be utilized to prevent or minimize release and absorption of the composition until it reaches the target tissue or organ, or to ensure timed-release of the composition. Desirably, however, a pharmaceutically acceptable form is employed which does not ineffectuate the cells expressing the chimeric receptor. Thus, desirably the transduced T cells can be made into a pharmaceutical composition containing a balanced salt solution, preferably Hanks' balanced salt solution, or normal saline.

Methods of Ameliorating or Reducing Symptoms of or Treating, or Preventing, Diseases and Disorders Using TCR-Deficient T-Cells The invention is also directed to methods of reducing or ameliorating, or preventing or treating, diseases and disorders using the TCR-deficient T cells described herein, isolated populations thereof, or therapeutic compositions comprising the same. In one embodiment, the TCR-deficient T cells described herein, isolated populations thereof, or therapeutic compositions comprising the same are used to reduce or ameliorate, or prevent or treat, cancer, infection, one or more autoimmune disorders, radiation sickness, or to prevent or treat graft versus host disease (GVHD) or transplantation rejection in a subject undergoing transplant surgery.

The TCR-deficient T cells described herein, isolated populations thereof, or therapeutic compositions comprising the same are useful in altering autoimmune or transplant rejection because these effector cells can be grown in TGF-β during development and will differentiate to become induced T regulatory cells. In one embodiment, the functional non-TCR is used to give these induced T regulatory cells the functional specificity that is required for them to perform their inhibitory function at the tissue site of disease. Thus, a large number of antigen-specific regulatory T cells are grown for use in patients. The expression of FoxP3, which is essential for T regulatory cell differentiation, can be analyzed by flow cytometry, and functional inhibition of T cell proliferation by these T regulatory cells can be analyzed by examining decreases in T cell proliferation after anti-CD3 stimulation upon co-culture.

Another embodiment of the invention is directed to the use of TCR-deficient T cells described herein, isolated populations thereof, or therapeutic compositions comprising the same for the prevention or treatment of radiation sickness. One challenge after radiation treatment or exposure (e.g. dirty bomb exposure, radiation leak) or other condition that ablates bone marrow cells (certain drug therapies) is to reconstitute the hematopoietic system. In patients undergoing a bone marrow transplant, the absolute lymphocyte count on day 15 post-transplant is correlated with successful outcome. Those patients with a high lymphocyte count reconstitute well, so it is important to have a good lymphocyte reconstitution. The reason for this effect is unclear, but it may be due to lymphocyte protection from infection and/or production of growth factors that favors hematopoietic reconstitution.

In this embodiment, TCR-deficient T cells described herein, isolated populations thereof, or therapeutic compositions comprising the same result in the production of a large number of T cells that are unable to respond to allogeneic MHC antigens. Hence, these T cells may be used to reconstitute people and offer protection from infection, leading to faster self-reconstitution of people suffering from full or partial bone marrow ablation due to radiation exposure. In the event of a catastrophic or unexpected exposure to high doses of radiation, TCR-deficient T cells described herein having another functional receptor, isolated populations thereof, or therapeutic compositions comprising the same can be infused rapidly into patients to offer some reconstitution of their immune response and growth factor production for days to weeks until their own hematopoietic cells have reconstituted themselves, or until the person has been treated with an additional source of hematopoietic stem cells (e.g. a bone marrow transplant).

One of skill would understand how to treat cancer, infection, transplantation rejection, one or more autoimmune disorders, radiation sickness, or GVHD based on their experience with use of other types of T cells.

In addition to the illustrative TCR-deficient chNKG2D+ T cells described herein, it is contemplated that TCR-deficient T cells can be modified or developed to express other functional receptors useful in treatment of diseases such as cancer or infection as described previously. Briefly, the treatment methods of the invention contemplate the use of TCR-deficient T cells expressing functional non-TCR receptors, such as chNKG2D, chimeric Fv domains, NKG2D, or any other receptor to initiate signals to T cells, thereby creating potent, specific effector T cells. One of skill in the art can select the appropriate receptor to be expressed by the TCR-deficient T cell based on the disease to be treated. For example, receptors that can be expressed by the TCR-deficient T cell for treatment of cancer would include any receptor that binds to a ligand that has been identified on cancer cells. Such receptors include, but are not limited to, NKG2D, NKG2A, NKG2C, NKG2F, LLT1, AICL, CD26, NKRP1, NKp30, NKp44, NKp46, CD244 (2B4), DNAM-1, and NKp80.

In another embodiment of the invention, such receptors include, but not limited to, chimeric receptors comprising a ligand binding domain obtained from NKG2D, NKG2A, NKG2C, NKG2F, LLT1, AICL, CD26, NKRP1, NKp30, NKp44, NKp46, CD244 (2B4), DNAM-1, and NKp80, or an anti-tumor antibody such as anti-Her2neu and anti-EGFR, and a signaling domain obtained from CD3zeta, Dap10, CD28, 41BB, and CD40L.

In a further embodiment of the invention, the chimeric receptor binds MIC-A, MIC-B, Her2neu, EGFR, mesothelin, CD38, CD20, CD19, PSA, MUC1, MUC2, MUC3A, MUC3B, MUC4, MUC5AC, MUC5B, MUC6, MUC7, MUC8, MUC12, MUC13, MUC15, MUC16, MUC17, MUC19, MUC20, estrogen receptor, progesterone receptor, RON, or one or more members of the ULBP/RAET1 family including ULBP1, ULBP2, ULBP3, ULBP4, ULBP5, and ULBP6.

Also embraced by the present invention are TCR-deficient T cells that express a non-TCR pathogen-associated receptor and the use of the TCR-deficient T cells expressing the pathogen receptor to treat or prevent infectious disease. In this embodiment, the non-TCR receptor binds to virus antigen or viral-induced antigen found on the surface of an infected cell. The infection to be prevented or treated, for example may be caused by a virus, bacteria, protozoa, or parasite. Viruses which can be treated include, but are not limited to, HCMV, EBV, hepatitis type A, hepatitis type B (HBV), hepatitis type C (HCV), ebola virus, VSV, influenza, varicella, adenovirus, herpes simplex type I (HSV-1), herpes simplex type 2 (HSV-2), rinderpest, rhinovirus, echovirus, rotavirus, respiratory syncytial virus, papilloma virus, cytomegalovirus (CMV), echinovirus, arbovirus, hantavirus, coxsackie virus, mumps virus, measles virus, rubella virus, polio virus, and/or human immunodeficiency virus type 1 or type 2 (HIV-1, HIV-2). Non-viral infections which can be treated using the TCR-deficient T cells include, but are not limited to, infectious *Staphylococcus* sp., *Enterococcus* sp., *Bacillus anthracis, Lactobacillus* sp., *Listeria* sp., *Corynebacterium diphtherias, Nocardia* sp., *Streptococcus* sp., *Pseudomonas* sp., *Gardnerella* sp., *Streptomyces* sp., *Thermoactinotnyces vulgaris, Treponema* sp., *Camplyobacter* sp., *Raeruginosa* sp., *Legionella* sp., *N. gonorrhoeae, N. meningitides, F. meningosepticurn, F. odoraturn, Brucella* sp., *B. pertussis, B. bronchiseptica, E. coli, Klebsiella, Enterobacter, S. marcescens, S. liquefaciens, Edwardsiella, P. mirabilis, P. vulgaris, Streptobacillus, R. fickettsfi, C. psittaci, C. trachornatis, M tuberculosis, M. intracellulare, M. folluiturn, M. laprae, M. avium, M. bovis, M. africanum, M. kansasii, M. lepraernurium, trypanosomes, Chlamydia,* or *rickettsia.*

Efficacy of the compositions of the present invention can be demonstrated in the most appropriate in vivo model system depending on the type of drug product being developed. The medical literature provides detailed disclosure on the advantages and uses of a wide variety of such models. For example, there are many different types of cancer models that are used routinely to examine the pharmacological activity of drugs against cancer such as xenograft mouse models (e.g., Mattern, J. et al. 1988. *Cancer Metastasis Rev.* 7:263-284; Macor, P. et al. 2008. Curr. Pharm. Des. 14:2023-2039) or even the inhibition of tumor cell growth in vitro. In the case of GVHD, there are models in mice of both acute GVHD (e.g., He, S. et al. 2008. *J. Immunol.* 181:7581-7592) and chronic GVHD (e.g., Xiao, Z. Y. et al. 2007. *Life Sci.* 81:1403-1410).

Once the compositions of the present invention have been shown to be effective in vivo in animals, clinical studies may be designed based on the doses shown to be safe and effective in animals. One of skill in the art can design such clinical studies using standard protocols as described in textbooks such as Spilker (2000. *Guide to Clinical Trials.* Lippincott Williams & Wilkins: Philadelphia).

Administration

In one embodiment of the invention, the TCR-deficient T cells are administered to a recipient subject at an amount of between about $10^6$ to $10^{11}$ cells. In a preferred embodiment of the invention, the TCR-deficient T cells are administered to a recipient subject at an amount of between $10^8$ to $10^9$ cells. In a preferred embodiment of the invention, the TCR-deficient T cells are administered to a recipient subject with a frequency of once every twenty-six weeks or less, such as once every sixteen weeks or less, once every eight weeks or less, or once every four weeks or less.

These values provide general guidance of the range of transduced T cells to be utilized by the practitioner upon optimizing the method of the present invention for practice of the invention. The recitation herein of such ranges by no means precludes the use of a higher or lower amount of a component, as might be warranted in a particular application. For example, the actual dose and schedule can vary depending on whether the compositions are administered in combination with other phaituaceutical compositions, or depending on interindividual differences in phaiinacokinetics, drug disposition, and metabolism. One skilled in the art readily can make any necessary adjustments in accordance with the exigencies of the particular situation.

A person of skill in the art would be able to determine an effective dosage and frequency of administration based on teachings in the art or through routine experimentation, for example guided by the disclosure herein and the teachings in Goodman, L. S., Gilman, A., Brunton, L. L., Lazo, J. S., & Parker, K. L. (2006). Goodman & Gilman's the pharmacological basis of therapeutics. New York: McGraw-Hill; Howland, R. D., Mycek, M. J., Harvey, R. A., Champe, P. C., & Mycek, M. J. (2006). Phaimacology. Lippincott's illustrated reviews. Philadelphia: Lippincott Williams & Wilkins; and Golan, D. E. (2008). Principles of pharmacology: the pathophysiologic basis of drug therapy. Philadelphia, Pa., [etc.]: Lippincott Williams & Wilkins. The dosing schedule can be based on well-established cell-based therapies (see, e.g., Topalian and Rosenberg (1987) Acta Haematol. 78 Suppl 1:75-6; U.S. Pat. No. 4,690,915) or an alternate continuous infusion strategy can be employed.

In another embodiment of the invention, the TCR-deficient T cells are administered to a subject in a pharmaceutical formulation.

In one embodiment of the invention, the TCR-deficient T cells may be optionally administered in combination with one or more active agents. Such active agents include analgesic, antipyretic, anti-inflammatory, antibiotic, antiviral, and anti-cytokine agents. Active agents include agonists, antagonists, and modulators of TNF-α, IL-2, IL-4, IL-6, IL-10, IL-12, IL-13, IL-18, IFN-α, IFN-γ, BAFF, CXCL13, IP-10, VEGF, EPO, EGF, HRG, Hepatocyte Growth Factor (HGF), Hepcidin, including antibodies reactive against any of the foregoing, and antibodies reactive against any of their receptors. Active agents also include 2-Arylpropionic acids, Aceclofenac, Acemetacin, Acetylsalicylic acid (Aspirin), Alclofenac, Alminoprofen, Amoxiprin, Ampyrone, Arylalkanoic acids, Azapropazone, Benorylate/Benorilate, Benoxaprofen, Bromfenac, Carprofen, Celecoxib, Choline magnesium salicylate, Clofezone, COX-2 inhibitors, Dexibuprofen, Dexketoprofen, Diclofenac, Diflunisal, Droxicam, Ethenzamide, Etodolac, Etoricoxib, Faislamine, fenamic acids, Fenbufen, Fenoprofen, Flufenamic acid, Flunoxaprofen, Flurbiprofen, Ibuprofen, Ibuproxam, Indometacin, Indoprofen, Kebuzone, Ketoprofen, Ketorolac, Lomoxicam, Loxoprofen, Lumiracoxib, Magnesium salicylate, Meclofenamic acid, Mefenamic acid, Meloxicam, Metamizole, Methyl salicylate, Mofebutazone, Nabumetone, Naproxen, N-Arylanthranilic acids, Nerve Growth Factor (NGF), Oxametacin, Oxaprozin, Oxicams, Oxyphenbutazone, Parecoxib, Phenazone, Phenylbutazone, Phenylbutazone, Piroxicam, Pirprofen, profens, Proglumetacin, Pyrazolidine derivatives, Rofecoxib, Salicyl salicylate, Salicylamide, Salicylates, Sulfinpyrazone, Sulindac, Suprofen, Tenoxicam, Tiaprofenic acid, Tolfenamic acid, Tolmetin, and Valdecoxib.

Antibiotics include Amikacin, Aminoglycosides, Amoxicillin, Ampicillin, Ansamycins, Arsphenamine, Azithromycin, Azlocillin, Aztreonam, Bacitracin, Carbacephem, Carbapenems, Carbenicillin, Cefaclor, Cefadroxil, Cefalexin, Cefalothin, Cefalotin, Cefamandole, Cefazolin, Cefdinir, Cefditoren, Cefepime, Cefixime, Cefoperazone, Cefotaxime, Cefoxitin, Cefpodoxime, Cefprozil, Ceftazidime, Ceftibuten, Ceftizoxime, Ceftobiprole, Ceftriaxone, Cefuroxime, Cephalosporins, Chloramphenicol, Cilastatin, Ciprofloxacin, Clarithromycin, Clindamycin, Cloxacillin, Colistin, Co-trimoxazole, Dalfopristin, Demeclocycline, Dicloxacillin, Dirithromycin, Doripenem, Doxycycline, Enoxacin, Ertapenem, Erythromycin, Ethambutol, Flucloxacillin, Fosfomycin, Furazolidone, Fusidic acid, Gatifloxacin, Geldanamycin, Gentamicin, Glycopeptides, Herbimycin, Imipenem, Isoniazid, Kanamycin, Levofloxacin, Lincomycin, Linezolid, Lomefloxacin, Loracarbef, Macrolides, Mafenide, Meropenem, Meticillin, Metronidazole, Mezlocillin, Minocycline, Monobactams, Moxifloxacin, Mupirocin, Nafcillin, Neomycin, Netilmicin, Nitrofurantoin, Norfloxacin, Ofloxacin, Oxacillin, Oxytetracycline, Paromomycin, Penicillin, Penicillins, Piperacillin, Platensimycin, Polymyxin B, Polypeptides, Prontosil, Pyrazinamide, Quinolones, Quinupristin, Rifampicin, Rifampin, Roxithromycin, Spectinomycin, Streptomycin, Sulfacetamide, Sulfamethizole, Sulfanilimide, Sulfasalazine, Sulfisoxazole, Sulfonamides, Teicoplanin, Telithromycin, Tetracycline, Tetracyclines, Ticarcillin, Tinidazole, Tobramycin, Trimethoprim, Trimethoprim-Sulfamethoxazole, Troleandomycin, Trovafloxacin, and Vancomycin.

Active agents also include Aldosterone, Beclometasone, Betamethasone, Corticosteroids, Cortisol, Cortisone acetate, Deoxycorticosterone acetate, Dexamethasone, Fludrocortisone acetate, Glucocorticoids, Hydrocortisone, Methylprednisolone, Prednisolone, Prednisone, Steroids, and Triamcinolone. Any suitable combination of these active agents is also contemplated.

A "pharmaceutical excipient" or a "pharmaceutically acceptable excipient" is a carrier, usually a liquid, in which an active therapeutic agent is formulated. In one embodiment of the invention, the active therapeutic agent is a population of TCR-deficient T cells. In one embodiment of the invention, the active therapeutic agent is a population of TCR-deficient T cells expressing a functional, non-TCR receptor. The excipient generally does not provide any pharmacological activity to the formulation, though it may provide chemical and/or biological stability. Exemplary formulations can be found, for example, in Remington's Pharmaceutical Sciences, $19^{th}$ Ed., Grennaro, A., Ed., 1995 which is incorporated by reference.

As used herein "pharmaceutically acceptable carrier" or "excipient" includes any and all solvents, dispersion media, coatings, antibacterial and antifungal agents, isotonic and absorption delaying agents that are physiologically compatible. In one embodiment, the carrier is suitable for parenteral administration. Alternatively, the carrier can be suitable for intravenous, intraperitoneal, intramuscular, or sublingual administration. Pharmaceutically acceptable carriers include sterile aqueous solutions or dispersions for the extemporaneous preparation of sterile injectable solutions or dispersions. The use of such media and agents for pharmaceutically active substances is well known in the art. Except insofar as any conventional media or agent is incompatible with the active compound, use thereof in the pharmaceutical compositions of the invention is contemplated. Supplementary active compounds can also be incorporated into the compositions.

In a particularly preferred embodiment of the invention, appropriate carriers include, but are not limited to, Hank's Balanced Salt Solution (HBSS), Phosphate Buffered Saline (PBS), or any freezing medium having for example 10% DMSO and 90% human serum.

Phaimaceutical compositions typically must be sterile and stable under the conditions of manufacture and storage. The invention contemplates that the pharmaceutical composition is present in lyophilized form. The composition can be foi ululated as a solution. The carrier can be a dispersion medium containing, for example, water.

For each of the recited embodiments, the compounds can be administered by a variety of dosage forms. Any biologically-acceptable dosage form known to persons of ordinary skill in the art, and combinations thereof, are contemplated. Examples of such dosage forms include, without limitation, liquids, solutions, suspensions, emulsions, injectables (including subcutaneous, intramuscular, intravenous, and intradermal), infusions, and combinations thereof.

The above description of various illustrated embodiments of the invention is not intended to be exhaustive or to limit the invention to the precise form disclosed. While specific embodiments of, and examples for, the invention are described herein for illustrative purposes, various equivalent modifications are possible within the scope of the invention, as those skilled in the relevant art will recognize. The teachings provided herein of the invention can be applied to other purposes, other than the examples described above.

These and other changes can be made to the invention in light of the above detailed description. In general, in the following claims, the terms used should not be construed to limit the invention to the specific embodiments disclosed in the specification and the claims. Accordingly, the invention is not limited by the disclosure, but instead the scope of the invention is to be deter mined entirely by the following claims.

The invention may be practiced in ways other than those particularly described in the foregoing description and examples. Numerous modifications and variations of the invention are possible in light of the above teachings and, therefore, are within the scope of the appended claims.

Certain teachings related to T-cell receptor deficient T-cell compositions and methods of use thereof were disclosed in U.S. Provisional patent application No. 61/255,980, filed Oct. 29, 2009, the disclosure of which is herein incorporated by reference in its entirety.

Certain teachings related to the production of T cells expressing chimeric receptors and methods of use thereof were disclosed in U.S. patent application publication no. US 2010/0029749, published Feb. 4, 2010, the disclosure of which is herein incorporated by reference in its entirety.

Certain polynucleotide sequences useful in the production of T-cell receptor deficient T-cells of the invention are disclosed in the sequence listing accompanying this patent application filing, and the disclosure of said sequence listing is herein incorporated by reference in its entirety.

The entire disclosure of each document cited (including patents, patent applications, journal articles, abstracts, manuals, books, or other disclosures) in the Background of the Invention, Detailed Description, and Examples is herein incorporated by reference in their entireties.

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

EXAMPLES

Example 1: Production of T Cell Receptor (TCR)-Deficient T Cells

Minigenes are encoded on a retrovirus expression plasmid (e.g. pFB-neo or pSFG) containing 5' and 3' LTR sequences. The plasmids are packaged in a retroviral packaging cell line, such as PT67 or PG13, and viral particles are collected once the packaging cells have grown to confluence. T cells are then activated by PHA, anti-CD3, or anti-CD3/28 mAbs for 1 to 3 days in complete medium (or serum free medium) plus rIL-2 (25 U/ml), and T cells are transduced by spinoculation at 32° C. in the presence of retronectin or polybrene. After resting for some 5 to 7 hours, the cells arc washed and placed in fresh medium plus IL-2 for 2 to 7 days. Cells are counted periodically to avoid excessive cell concentration (i.e., >$2\times10^6$ cells/ml) and re-plated at $7\times10^5$ cells/ml. Selection medium to remove non-transduced T cells is optionally used after 2 days for a period of 3 to 5 days. Live cells are harvested by Lymphoprep™ (Sentinel, Milan, Italy) gradient and further expanded for 1 to 3 days.

Following incubation, cells are analyzed for expression and function of the TCR. Functional non-TCR receptor expression may also be analyzed at this time, if appropriate. Flow cytometry is used to test for TCR/CD3 expression using fluorochrome-labeled antibodies. Live cells are stained with antibodies against CD5, CD8, and CD4, in combination with an antibody against CD3ε, TCRα, TCRβ, TCRγ, or TCRδ. If the expression of either the CD3 or TCR genes is used, the expression of both TCR proteins and CD3 proteins should be severely reduced compared to control vector treated T cells. Isotype control antibodies are used to control for background fluorescence. To identify T cells, cells are gated on CD5, then expression of CD4, CD8, CD3, and TCR is determined. Multiple samples are used for each treatment and appropriate compensation of fluorochrome emission spectra is used. The expression of another receptor (e.g. chNKG2D) is determined using specific antibodies and flow cytometry, as previously described in the art (Zhang, T. et al., (2006) Cancer Res., 66(11) 5927-5933; Barber, A. et al., (2007) Cancer Res., 67(10):5003-5008).

To test for functional deficiency of the TCR, anti-CD3 stimulation of effector cells is used at the end of culture to measure interferon (IFN)-gamma production after 24 hours. T cells ($2\times10^5$) are cultured with soluble anti-CD3 (OKT3) mAbs in complete medium. After 24 hours, cell-free conditioned medium is collected and assayed by ELISA for IFN-gamma. Changes in TCR expression or function should be reflected in reduced IFN-gamma production.

To test for the function of the functional non-TCR, specific cytokine production by T cells incubated with tumor cells that do, or do not, express their specific ligand is used. For example, to test the function of chNKG2D, $10^5$ T cells are incubated with $10^5$ P815-MICA tumor cells (ligand+), $10^5$ P815 (ligand-) cells, $10^5$ RPMI8226 cells (ligand+) or T cells alone. After 24 hours, cell-free conditioned medium is collected and IFN-g measured by ELISA. Chimeric NKG2D T cells produce IFN-g after culture with ligand-expressing tumor cells (Zhang, T. et al., (2006) Cancer Res., 66(11) 5927-5933; Barber, A. et al., (2007) Cancer Res., 67(10): 5003-5008). It is also possible to test cellular cytotoxicity against ligand+tumor cells, as previously described in the art (Zhang, T. et al., (2006) Cancer Res., 66(11) 5927-5933). Specificity is shown using ligand-tumor cells or specific receptor blocking mAbs.

Example 2: Production of T Cell Receptor (TCR)-Deficient T Cells Expressing chNKG2D In this example, simultaneous expression of a chNKG2D receptor and inhibition of endogenous TCR expression is performed. In this example, a murine chNKG2D receptor is used, composed of NKG2D in combination with a N-terminally attached CD3-zeta. The chNKG2D receptor is generated and expressed in murine T-cells. NKG2D is a type II protein, in which the N-terminus is located intracellularly (Raulet (2003) Nat. Rev. Immunol. 3:781-790), whereas the CD3-zeta chain is type I protein with the C-terminus in the cytoplasm (Weissman, et al. (1988) Proc. Natl. Acad. Sci. USA 85:9709-9713). To generate a chimeric NKG2D-CD3-zeta fusion protein, an initiation codon ATG is placed ahead of the coding sequence for the cytoplasmic region of the CD3-zeta chain (without a stop codon TAA) followed by a wild-type NKG2D gene. Upon expression, the orientation of the CD3-zeta portion is reversed inside the cells. The extracellular and transmembrane domains are derived from NKG2D. A second chimeric gene encoding the Dap10 gene followed by a fragment coding for the CD3-zeta cytoplasmic domain is also constructed. FIG. 1 presents the structures of the chimeric and wild-type receptors.

An shRNA is operably linked in a lentiviral vector with the chNKG2D receptor. To achieve expression of both genes, the shRNA is driven by a U6 promoter and the chNKG2D receptor by a PGK promoter. Primary human PBMCs are isolated from healthy donors and activated with low-dose soluble anti-CD3 and 25 U/ml rhuIL-2 for 48 hours. Although it is not required to activate T cells for lentiviral transduction, the transduction will work more efficiently and allow the cells to continue to expand in IL-2. The activated cells are washed and transduced using a 1 h spin-fection at 30° C., followed by a resting period for 7 h. The cells are washed and cultured in 25 U/ml IL-2 for 3 to 7 d to allow expansion of the effector cells in a similar manner as we do for use of the cells in vivo. The expression of TCRαβ, CD3, and NKG2D is evaluated by flow cytometry and quantitative realtime-PCR (QRT-PCR). The number of CD4+ and CD8+ T cells are determined by flow cytometry. Overall cell numbers and the percentage of TCR complex deficient and expressing T cells are deter mined by flow cytometry. These are compared to PBMCs that are transduced with the shRNA or chNKG2D genes alone (as controls). Vector-only transduced cells are also included as controls.

It is anticipated that those cells with no or little TCR expression at the cell surface will express higher amounts of cell surface NKG2D because of co-expression of the chNKG2D receptor.

As an alternative, transduction may occur with two viruses at the same time, one with the shRNA construct and one with the chNKG2D receptor. A larger amount of the chNKG2D virus is used to ensure high expression of chNKG2D in those T cells that lack TCR expression. TCR+ T cells that may remain are removed to obtain TCR−, chNKG2D+ T cells.

After viral transduction and expansion, the TCR+ and TCR− cells are separated by mAbs with magnetic beads over Miltenyi columns. Verification of chNKG2D expression is performed by QRT-PCR using specific primers for the chNKG2D receptor.

To determine whether the T cells have lost TCR function and retained chNKG2D function, transduced or control T cells are cultured with mitomycin C-treated allogeneic PBMCs or syngeneic PBMCs. The T cells are preloaded with CFSE, which is a cell permeable dye that divides equally between daughter cells after division. The extent of cell division can be easily determined by flow cytometry.

To determine whether the shRNA construct can inhibit TCR function and allow chNKG2D receptor function, transduced T cells are cultured with mitomycin C-treated allogeneic PBMCs, syngeneic PBMCs, or tumor cells: P815-MICA (a murine tumor expressing human MICA, a ligand for NKG2D), P815, A2008 (a human ovarian tumor cell, NKG2D ligand+), and U266 (a human myeloma cell line, NKG2D ligand+). After 48 hours, cell-free supernatants are collected and the amount of IL-2 and IFN-γ produced will be quantitated by ELISA. T cells alone are used as a negative control.

Example 3: In Vivo Administration of T Cell Receptor (TCR)-Deficient T Cells Expressing chNKG2D In this example, the TCR-deficient T cells expressing a murine chNKG2D receptor as produced in Example 2 are administered to mice to evaluate the in vivo therapeutic potential of said T cells on certain cancers. The chimeric NKG2D-bearing T cells ($10^6$) are co-injected with RMA/Rae-1β tumor cells ($10^5$) subcutaneously to C57BL/6 mice. Chimeric NKG2D-bearing, TCR-deficient T cell-treated mice that are tumor-free or have tumor-inhibited growth of RMA/Rae-1β tumors after 30 days reflects therapeutic anti-cancer activity in these mice.

In a second and more stringent model, transduced T cells ($10^7$) are adoptively transferred i.v. into B6 mice one day before RMA/Rae-1β s.c. tumor inoculation in the right flank. Suppression of the growth of the RMA/Rae-1β tumors (s.c.) compared with control vector-modified T cells reflects therapeutic anti-cancer activity in these mice. As for toxicity of treatment with chimeric NKG2D-modified T cells, it is anticipated that the animals will not show any overt evidence of inflammatory damage (i.e., ruffled hair, hunchback or diarrhea, etc.) when treated with chimeric NKG2D-bearing T cells, which would be reflective of a lack of overt toxicity.

In a more stringent model of established ovarian tumors (ID8), transduced chNKG2D T cells ($5 \times 10^6$ T cells, i.p.) are injected into mice bearing tumors for 5 weeks. Mice are further injected with T cells at 7 and 9 weeks following tumor challenge. Under these conditions, mice treated with chNKG2D T cells will remain tumor-free for more than 250 days, whereas mice treated on a similar schedule with control T cells will die from tumor growth within 100 days. As for toxicity of treatment with chimeric NKG2D-modified T cells, it is anticipated that the animals will not show any overt evidence of inflammatory damage (i.e., ruffled hair, hunchback or diarrhea, etc.) when treated with chimeric NKG2D-bearing T cells, which would be reflective of a lack of overt toxicity.

In a model of multiple myeloma, mice bearing 5T33MM tumor cells are treated on day 12 post tumor cell infusion with chNKG2D T cells ($5 \times 10^6$ cells, i.v.). This treatment will result in an increased life-span of all mice and about half of these mice will be long-tumor-free survivors. Mice treated with control T cells will succumb to their tumors within 30 days. No overt evidence of toxicity will be observed due to treatment with the chNKG2D T cells.

Because the immune system can select for tumor variants, the most effective immunotherapies for cancer are likely going to be those that induce immunity against multiple tumor antigens. In a third experiment, it is tested whether treatment with chimeric NKG2D-bearing T cells will induce host immunity against wild-type tumor cells. Mice that are treated with chimeric NKG2D-bearing T cells and 5T33MM tumor cells, and are tumor-free after 80 days, are challenged with 5T33MM tumor cells. Tumor-free surviving mice are resistant to a subsequent challenge of 5T33MM cells ($3\times10^5$), compared to control naive mice which succumb to the tumor within an average of 27 days. However, tumor-free surviving mice are not resistant to a subsequent challenge of RMA-Rael tumor cells ($3\times10^5$), and succumb to the tumor in a similar time-span as naïve mice (20 days). This indicates that adoptive transfer of chimeric NKG2D-bearing T cells will allow hosts to generate tumor-specific T cell memory.

What is claimed is:

1. A method of treating cancer in a human subject in need thereof which comprises administering a pharmaceutically effective amount of isolated primary human T cells or progeny thereof, which isolated primary human T cells:
   (i) have been modified to functionally impair and/or to reduce expression of the endogenous T cell receptor (TCR); and
   (ii) have been modified to express at least one functional exogenous non-TCR receptor comprising a ligand binding domain which binds to a ligand expressed by tumor cells of said subject, which exogenous ligand binding domain directly or indirectly mediates T cell signaling upon the binding of the ligand binding domain to a ligand expressed by a tumor cell in the treated subject.

2. The method of treating cancer of claim 1, wherein a pool of said isolated modified human T cells or progeny thereof is administered to the subject.

3. The method of treating cancer of claim 1, wherein the cell comprises an exogenous signaling domain which initiates T cell signaling.

4. The method of treating cancer of claim 1, wherein the ligand binding domain which binds to a ligand expressed by tumor cells is an anti-tumor antigen receptor or an anti-tumor antibody.

5. The method of treating cancer of claim 1, wherein the expression of the endogenous TCR is reduced in the administered isolated modified primary human T cells or progeny thereof.

6. The method of treating cancer of claim 1, wherein the functionality of the endogenous TCR is impaired in the administered isolated modified primary human T cells or progeny thereof.

7. The method of treating cancer of claim 1, wherein the administered isolated modified primary human T cells or progeny thereof elicit a reduced graft versus host disease (GVHD) response against allogeneic (HLA-mismatched) cells in a treated subject compared to that elicited by isolated primary human T cells which express the same endogenous TCR but which endogenous TCR is not impaired.

8. The method of treating cancer of claim 1, wherein the administered isolated modified primary human T cells or progeny thereof do not elicit a GVHD response in a histoincompatible human recipient.

9. The method of treating cancer of claim 3, wherein the administered isolated modified primary human T cells or progeny thereof do not elicit a GVHD response in a histoincompatible human recipient.

10. The method of treating cancer of claim 1, wherein the non-TCR receptor expressed by the isolated primary human T cells which binds to a ligand expressed by tumor cells comprises a NKG2D, NKG2A, NKG2C, NKG2F, LLT1, AICL, CD26, or NKRP1 polypeptide.

11. The method of treating cancer of claim 1, wherein the non-TCR receptor expressed by the isolated primary human T cells which binds to a ligand expressed by tumor cells comprises a chimeric Fv.

12. The method of treating cancer of claim 1, wherein the non-TCR receptor is a chimeric receptor which comprises (1) said ligand binding domain which binds to a ligand expressed by a ligand expressed by tumor cells of the treated subject and further comprises (2) a signaling domain.

13. The method of treating cancer of claim 12, wherein the ligand binding domain of the chimeric receptor binds to a receptor selected from MIC-A, MIC-B, estrogen, progesterone, RON, or one or more members of the ULBP/RAET1 family.

14. The method of treating cancer of claim 12, wherein the receptor ligand binding domain comprised in said chimeric receptor comprises a NKG2D, NKG2A, NKG2C, NKG2F, LLT1, AICL, CD26, or NKRP1 polypeptide.

15. The method of treating cancer of claim 1, wherein the ligand binding domain which binds to a ligand expressed by tumor cells comprises an NKG2D polypeptide.

16. The method of treating cancer of claim 1, wherein the ligand binding domain which binds to a ligand expressed by tumor cells comprises a natural killer (NK) cell receptor.

17. The method of treating cancer of claim 1, wherein the non-TCR receptor is a chimeric receptor which comprises: (1) said ligand binding domain which binds to a ligand expressed by tumor cells of the treated subject; and (2) a signaling domain, wherein said ligand binding domain comprises a NKG2D ligand binding domain, and said signaling domain comprises a CD3ζ signaling domain.

18. The method of treating cancer of claim 1, wherein the administered isolated primary human T cells or progeny thereof are derived from allogeneic T cells or primary human PBMCs of a human subject.

19. The method of treating cancer of claim 1, wherein the administered isolated primary human T cells or progeny thereof express CD4.

20. The method of treating cancer of claim 1, wherein the administered isolated primary human T cells or progeny thereof express CD8.

21. The method of treating cancer of claim 1, wherein the administered isolated primary human T cells or progeny thereof are capable of differentiating into T regulatory cells.

* * * * *

SEQUENCE LISTING

```
<160> NUMBER OF SEQ ID NOS: 63

<210> SEQ ID NO 1
<211> LENGTH: 25
<212> TYPE: DNA
<213> ORGANISM: Artificial Sequence
<220> FEATURE:
<223> OTHER INFORMATION: TCR-beta shRNA sequence

<400> SEQUENCE: 1
agtgcgagga gattcggcag cttat                                          25

<210> SEQ ID NO 2
<211> LENGTH: 25
<212> TYPE: DNA
<213> ORGANISM: Artificial Sequence
<220> FEATURE:
<223> OTHER INFORMATION: TCR-beta shRNA sequence

<400> SEQUENCE: 2
gcgaggagat tcggcagctt atttc                                          25

<210> SEQ ID NO 3
<211> LENGTH: 25
<212> TYPE: DNA
<213> ORGANISM: Artificial Sequence
<220> FEATURE:
<223> OTHER INFORMATION: TCR-beta shRNA sequence

<400> SEQUENCE: 3
ccaccatcct ctatgagatc ttgct                                          25

<210> SEQ ID NO 4
<211> LENGTH: 25
<212> TYPE: DNA
<213> ORGANISM: Artificial Sequence
<220> FEATURE:
<223> OTHER INFORMATION: TCR-beta shRNA sequence

<400> SEQUENCE: 4
tcctctatga gatcttgcta gggaa                                          25

<210> SEQ ID NO 5
<211> LENGTH: 25
<212> TYPE: DNA
<213> ORGANISM: Artificial Sequence
<220> FEATURE:
<223> OTHER INFORMATION: TCR-alpha shRNA sequence

<400> SEQUENCE: 5
tctatggctt caactggcta gggtg                                          25

<210> SEQ ID NO 6
<211> LENGTH: 25
<212> TYPE: DNA
<213> ORGANISM: Artificial Sequence
<220> FEATURE:
<223> OTHER INFORMATION: TCR-alpha shRNA sequence
```

```
<400> SEQUENCE: 6
caggtagagg ccttgtccac ctaat                                              25

<210> SEQ ID NO 7
<211> LENGTH: 25
<212> TYPE: DNA
<213> ORGANISM: Artificial Sequence
<220> FEATURE:
<223> OTHER INFORMATION: TCR-alpha shRNA sequence

<400> SEQUENCE: 7
gcagcagaca ctgcttctta cttct                                              25

<210> SEQ ID NO 8
<211> LENGTH: 25
<212> TYPE: DNA
<213> ORGANISM: Artificial Sequence
<220> FEATURE:
<223> OTHER INFORMATION: TCR-alpha shRNA sequence

<400> SEQUENCE: 8
gacactgctt cttacttctg tgcta                                              25

<210> SEQ ID NO 9
<211> LENGTH: 25
<212> TYPE: DNA
<213> ORGANISM: Artificial Sequence
<220> FEATURE:
<223> OTHER INFORMATION: CD3-epsilon shRNA sequence

<400> SEQUENCE: 9
cctctgcctc ttatcagttg gcgtt                                              25

<210> SEQ ID NO 10
<211> LENGTH: 25
<212> TYPE: DNA
<213> ORGANISM: Artificial Sequence
<220> FEATURE:
<223> OTHER INFORMATION: CD3-epsilon shRNA sequence

<400> SEQUENCE: 10
gagcaaagtg gttattatgt ctgct                                              25

<210> SEQ ID NO 11
<211> LENGTH: 25
<212> TYPE: DNA
<213> ORGANISM: Artificial Sequence
<220> FEATURE:
<223> OTHER INFORMATION: CD3-epsilon shRNA sequence

<400> SEQUENCE: 11
aagcaaacca gaagatgcga acttt                                              25

<210> SEQ ID NO 12
<211> LENGTH: 25
<212> TYPE: DNA
<213> ORGANISM: Artificial Sequence
<220> FEATURE:
<223> OTHER INFORMATION: CD3-epsilon shRNA sequence

<400> SEQUENCE: 12
gacctgtatt ctggcctgaa tcaga                                              25

<210> SEQ ID NO 13
```

```
<211> LENGTH: 21
<212> TYPE: DNA
<213> ORGANISM: Artificial Sequence
<220> FEATURE:
<223> OTHER INFORMATION: CD3-epsilon shRNA sequence

<400> SEQUENCE: 13
ggcctctgcc tcttatcagt t                                              21

<210> SEQ ID NO 14
<211> LENGTH: 21
<212> TYPE: DNA
<213> ORGANISM: Artificial Sequence
<220> FEATURE:
<223> OTHER INFORMATION: CD3-epsilon shRNA sequence

<400> SEQUENCE: 14
gcctctgcct cttatcagtt g                                              21

<210> SEQ ID NO 15
<211> LENGTH: 21
<212> TYPE: DNA
<213> ORGANISM: Artificial Sequence
<220> FEATURE:
<223> OTHER INFORMATION: CD3-epsilon shRNA sequence

<400> SEQUENCE: 15
gcctcttatc agttggcgtt t                                              21

<210> SEQ ID NO 16
<211> LENGTH: 21
<212> TYPE: DNA
<213> ORGANISM: Artificial Sequence
<220> FEATURE:
<223> OTHER INFORMATION: CD3-epsilon shRNA sequence

<400> SEQUENCE: 16
aggatcacct gtcactgaag g                                              21

<210> SEQ ID NO 17
<211> LENGTH: 21
<212> TYPE: DNA
<213> ORGANISM: Artificial Sequence
<220> FEATURE:
<223> OTHER INFORMATION: CD3-epsilon shRNA sequence

<400> SEQUENCE: 17
ggatcacctg tcactgaagg a                                              21

<210> SEQ ID NO 18
<211> LENGTH: 21
<212> TYPE: DNA
<213> ORGANISM: Artificial Sequence
<220> FEATURE:
<223> OTHER INFORMATION: CD3-epsilon shRNA sequence

<400> SEQUENCE: 18
gaattggagc aaagtggtta t                                              21

<210> SEQ ID NO 19
<211> LENGTH: 21
<212> TYPE: DNA
<213> ORGANISM: Artificial Sequence
<220> FEATURE:
<223> OTHER INFORMATION: CD3-epsilon shRNA sequence

<400> SEQUENCE: 19
```

```
ggagcaaagt ggttattatg t                                          21

<210> SEQ ID NO 20
<211> LENGTH: 21
<212> TYPE: DNA
<213> ORGANISM: Artificial Sequence
<220> FEATURE:
<223> OTHER INFORMATION: CD3-epsilon shRNA sequence

<400> SEQUENCE: 20
gcaaaccaga agatgcgaac t                                          21

<210> SEQ ID NO 21
<211> LENGTH: 21
<212> TYPE: DNA
<213> ORGANISM: Artificial Sequence
<220> FEATURE:
<223> OTHER INFORMATION: CD3-epsilon shRNA sequence

<400> SEQUENCE: 21
acctgtattc tggcctgaat c                                          21

<210> SEQ ID NO 22
<211> LENGTH: 21
<212> TYPE: DNA
<213> ORGANISM: Artificial Sequence
<220> FEATURE:
<223> OTHER INFORMATION: CD3-epsilon shRNA sequence

<400> SEQUENCE: 22
gcctgaatca gagacgcatc t                                          21

<210> SEQ ID NO 23
<211> LENGTH: 29
<212> TYPE: DNA
<213> ORGANISM: Artificial Sequence
<220> FEATURE:
<223> OTHER INFORMATION: CD3-epsilon shRNA sequence

<400> SEQUENCE: 23
ctgaaatact atggcaacac aatgataaa                                  29

<210> SEQ ID NO 24
<211> LENGTH: 29
<212> TYPE: DNA
<213> ORGANISM: Artificial Sequence
<220> FEATURE:
<223> OTHER INFORMATION: CD3-epsilon shRNA sequence

<400> SEQUENCE: 24
aaacataggc agtgatgagg atcacctgt                                  29

<210> SEQ ID NO 25
<211> LENGTH: 29
<212> TYPE: DNA
<213> ORGANISM: Artificial Sequence
<220> FEATURE:
<223> OTHER INFORMATION: CD3-epsilon shRNA sequence

<400> SEQUENCE: 25
attgtcatag tggacatctg catcactgg                                  29

<210> SEQ ID NO 26
<211> LENGTH: 29
<212> TYPE: DNA
```

```
<213> ORGANISM: Artificial Sequence
<220> FEATURE:
<223> OTHER INFORMATION: CD3-epsilon shRNA sequence

<400> SEQUENCE: 26
ctgtattctg gcctgaatca gagacgcat                                    29

<210> SEQ ID NO 27
<211> LENGTH: 21
<212> TYPE: DNA
<213> ORGANISM: Artificial Sequence
<220> FEATURE:
<223> OTHER INFORMATION: CD3-delta shRNA sequence

<400> SEQUENCE: 27
gatacctata gaggaacttg a                                            21

<210> SEQ ID NO 28
<211> LENGTH: 21
<212> TYPE: DNA
<213> ORGANISM: Artificial Sequence
<220> FEATURE:
<223> OTHER INFORMATION: CD3-delta shRNA sequence

<400> SEQUENCE: 28
gacagagtgt ttgtgaattg c                                            21

<210> SEQ ID NO 29
<211> LENGTH: 21
<212> TYPE: DNA
<213> ORGANISM: Artificial Sequence
<220> FEATURE:
<223> OTHER INFORMATION: CD3-delta shRNA sequence

<400> SEQUENCE: 29
gaacactgct ctcagacatt a                                            21

<210> SEQ ID NO 30
<211> LENGTH: 21
<212> TYPE: DNA
<213> ORGANISM: Artificial Sequence
<220> FEATURE:
<223> OTHER INFORMATION: CD3-delta shRNA sequence

<400> SEQUENCE: 30
ggacccacga ggaatatata g                                            21

<210> SEQ ID NO 31
<211> LENGTH: 21
<212> TYPE: DNA
<213> ORGANISM: Artificial Sequence
<220> FEATURE:
<223> OTHER INFORMATION: CD3-delta shRNA sequence

<400> SEQUENCE: 31
ggtgtaatgg gacagatata t                                            21

<210> SEQ ID NO 32
<211> LENGTH: 21
<212> TYPE: DNA
<213> ORGANISM: Artificial Sequence
<220> FEATURE:
<223> OTHER INFORMATION: CD3-delta shRNA sequence

<400> SEQUENCE: 32
gcaagttcat tatcgaatgt g                                            21
```

<210> SEQ ID NO 33
<211> LENGTH: 21
<212> TYPE: DNA
<213> ORGANISM: Artificial Sequence
<220> FEATURE:
<223> OTHER INFORMATION: CD3-delta shRNA sequence

<400> SEQUENCE: 33
ggctggcatc attgtcactg a                                         21

<210> SEQ ID NO 34
<211> LENGTH: 21
<212> TYPE: DNA
<213> ORGANISM: Artificial Sequence
<220> FEATURE:
<223> OTHER INFORMATION: CD3-delta shRNA sequence

<400> SEQUENCE: 34
gctggcatca ttgtcactga t                                         21

<210> SEQ ID NO 35
<211> LENGTH: 21
<212> TYPE: DNA
<213> ORGANISM: Artificial Sequence
<220> FEATURE:
<223> OTHER INFORMATION: CD3-delta shRNA sequence

<400> SEQUENCE: 35
gcatcattgt cactgatgtc a                                         21

<210> SEQ ID NO 36
<211> LENGTH: 21
<212> TYPE: DNA
<213> ORGANISM: Artificial Sequence
<220> FEATURE:
<223> OTHER INFORMATION: CD3-delta shRNA sequence

<400> SEQUENCE: 36
gctttgggag tcttctgctt t                                         21

<210> SEQ ID NO 37
<211> LENGTH: 29
<212> TYPE: DNA
<213> ORGANISM: Artificial Sequence
<220> FEATURE:
<223> OTHER INFORMATION: CD3-delta shRNA sequence

<400> SEQUENCE: 37
tggaacatag cacgtttctc tctggcctg                                 29

<210> SEQ ID NO 38
<211> LENGTH: 29
<212> TYPE: DNA
<213> ORGANISM: Artificial Sequence
<220> FEATURE:
<223> OTHER INFORMATION: CD3-delta shRNA sequence

<400> SEQUENCE: 38
ctgctctcag acattacaag actggacct                                 29

<210> SEQ ID NO 39
<211> LENGTH: 29
<212> TYPE: DNA
<213> ORGANISM: Artificial Sequence
<220> FEATURE:

<223> OTHER INFORMATION: CD3-delta shRNA sequence

<400> SEQUENCE: 39
accgtggctg gcatcattgt cactgatgt                                29

<210> SEQ ID NO 40
<211> LENGTH: 29
<212> TYPE: DNA
<213> ORGANISM: Artificial Sequence
<220> FEATURE:
<223> OTHER INFORMATION: CD3-delta shRNA sequence

<400> SEQUENCE: 40
tgatgctcag tacagccacc ttggaggaa                                29

<210> SEQ ID NO 41
<211> LENGTH: 21
<212> TYPE: DNA
<213> ORGANISM: Artificial Sequence
<220> FEATURE:
<223> OTHER INFORMATION: CD3-gamma shRNA sequence

<400> SEQUENCE: 41
ggctatcatt cttcttcaag g                                        21

<210> SEQ ID NO 42
<211> LENGTH: 21
<212> TYPE: DNA
<213> ORGANISM: Artificial Sequence
<220> FEATURE:
<223> OTHER INFORMATION: CD3-gamma shRNA sequence

<400> SEQUENCE: 42
gcccagtcaa tcaaaggaaa c                                        21

<210> SEQ ID NO 43
<211> LENGTH: 21
<212> TYPE: DNA
<213> ORGANISM: Artificial Sequence
<220> FEATURE:
<223> OTHER INFORMATION: CD3-gamma shRNA sequence

<400> SEQUENCE: 43
ggttaaggtg tatgactatc a                                        21

<210> SEQ ID NO 44
<211> LENGTH: 21
<212> TYPE: DNA
<213> ORGANISM: Artificial Sequence
<220> FEATURE:
<223> OTHER INFORMATION: CD3-gamma shRNA sequence

<400> SEQUENCE: 44
ggttcggtac ttctgacttg t                                        21

<210> SEQ ID NO 45
<211> LENGTH: 21
<212> TYPE: DNA
<213> ORGANISM: Artificial Sequence
<220> FEATURE:
<223> OTHER INFORMATION: CD3-gamma shRNA sequence

<400> SEQUENCE: 45
gaatgtgtca gaactgcatt g                                        21

```
<210> SEQ ID NO 46
<211> LENGTH: 21
<212> TYPE: DNA
<213> ORGANISM: Artificial Sequence
<220> FEATURE:
<223> OTHER INFORMATION: CD3-gamma shRNA sequence

<400> SEQUENCE: 46
gcagccacca tatctggctt t                                             21

<210> SEQ ID NO 47
<211> LENGTH: 21
<212> TYPE: DNA
<213> ORGANISM: Artificial Sequence
<220> FEATURE:
<223> OTHER INFORMATION: CD3-gamma shRNA sequence

<400> SEQUENCE: 47
ggctttctct ttgctgaaat c                                             21

<210> SEQ ID NO 48
<211> LENGTH: 21
<212> TYPE: DNA
<213> ORGANISM: Artificial Sequence
<220> FEATURE:
<223> OTHER INFORMATION: CD3-gamma shRNA sequence

<400> SEQUENCE: 48
gctttctctt tgctgaaatc g                                             21

<210> SEQ ID NO 49
<211> LENGTH: 21
<212> TYPE: DNA
<213> ORGANISM: Artificial Sequence
<220> FEATURE:
<223> OTHER INFORMATION: CD3-gamma shRNA sequence

<400> SEQUENCE: 49
gccaccttca aggaaaccag t                                             21

<210> SEQ ID NO 50
<211> LENGTH: 21
<212> TYPE: DNA
<213> ORGANISM: Artificial Sequence
<220> FEATURE:
<223> OTHER INFORMATION: CD3-gamma shRNA sequence

<400> SEQUENCE: 50
gaaaccagtt gaggaggaat t                                             21

<210> SEQ ID NO 51
<211> LENGTH: 29
<212> TYPE: DNA
<213> ORGANISM: Artificial Sequence
<220> FEATURE:
<223> OTHER INFORMATION: CD3-gamma shRNA sequence

<400> SEQUENCE: 51
ggctttctct ttgctgaaat cgtcagcat                                     29

<210> SEQ ID NO 52
<211> LENGTH: 29
<212> TYPE: DNA
<213> ORGANISM: Artificial Sequence
<220> FEATURE:
<223> OTHER INFORMATION: CD3-gamma shRNA sequence
```

```
<400> SEQUENCE: 52
aggatggagt tcgccagtcg agagcttca                                        29

<210> SEQ ID NO 53
<211> LENGTH: 29
<212> TYPE: DNA
<213> ORGANISM: Artificial Sequence
<220> FEATURE:
<223> OTHER INFORMATION: CD3-gamma shRNA sequence

<400> SEQUENCE: 53
cctcaaggat cgagaagatg accagtaca                                        29

<210> SEQ ID NO 54
<211> LENGTH: 29
<212> TYPE: DNA
<213> ORGANISM: Artificial Sequence
<220> FEATURE:
<223> OTHER INFORMATION: CD3-gamma shRNA sequence

<400> SEQUENCE: 54
tacagccacc ttcaaggaaa ccagttgag                                        29

<210> SEQ ID NO 55
<211> LENGTH: 17
<212> TYPE: PRT
<213> ORGANISM: Artificial Sequence
<220> FEATURE:
<223> OTHER INFORMATION: Immunoreceptor tyrosine-based activation motif
      (ITAM)
<220> FEATURE:
<221> NAME/KEY: VARIANT
<222> LOCATION: (1)..(1)
<223> OTHER INFORMATION: Xaa may be Asp or Glu
<220> FEATURE:
<221> NAME/KEY: VARIANT
<222> LOCATION: (2)..(3)
<223> OTHER INFORMATION: Xaa may be any amino acid
<220> FEATURE:
<221> NAME/KEY: VARIANT
<222> LOCATION: (5)..(6)
<223> OTHER INFORMATION: Xaa may be any amino acid
<220> FEATURE:
<221> NAME/KEY: VARIANT
<222> LOCATION: (7)..(7)
<223> OTHER INFORMATION: Xaa may be Ile or Leu
<220> FEATURE:
<221> NAME/KEY: VARIANT
<222> LOCATION: (8)..(13)
<223> OTHER INFORMATION: Xaa may be any amino acid
<220> FEATURE:
<221> NAME/KEY: VARIANT
<222> LOCATION: (15)..(16)
<223> OTHER INFORMATION: Xaa may be any amino acid
<220> FEATURE:
<221> NAME/KEY: VARIANT
<222> LOCATION: (17)..(17)
<223> OTHER INFORMATION: Xaa may be Ile or Leu

<400> SEQUENCE: 55

Xaa Xaa Xaa Tyr Xaa Xaa Xaa Xaa Xaa Xaa Xaa Xaa Xaa Tyr Xaa Xaa
1               5                   10                  15

Xaa

<210> SEQ ID NO 56
<211> LENGTH: 18
<212> TYPE: PRT
<213> ORGANISM: Artificial Sequence
<220> FEATURE:
<223> OTHER INFORMATION: Immunoreceptor tyrosine-based activation motif
```

```
            (ITAM)
<220> FEATURE:
<221> NAME/KEY: VARIANT
<222> LOCATION: (1)..(1)
<223> OTHER INFORMATION: Xaa may be Asp or Glu
<220> FEATURE:
<221> NAME/KEY: VARIANT
<222> LOCATION: (2)..(3)
<223> OTHER INFORMATION: Xaa may be any amino acid
<220> FEATURE:
<221> NAME/KEY: VARIANT
<222> LOCATION: (5)..(6)
<223> OTHER INFORMATION: Xaa may be any amino acid
<220> FEATURE:
<221> NAME/KEY: VARIANT
<222> LOCATION: (7)..(7)
<223> OTHER INFORMATION: Xaa may be Ile or Leu
<220> FEATURE:
<221> NAME/KEY: VARIANT
<222> LOCATION: (8)..(14)
<223> OTHER INFORMATION: Xaa may be any amino acid
<220> FEATURE:
<221> NAME/KEY: VARIANT
<222> LOCATION: (16)..(17)
<223> OTHER INFORMATION: Xaa may be any amino acid
<220> FEATURE:
<221> NAME/KEY: VARIANT
<222> LOCATION: (18)..(18)
<223> OTHER INFORMATION: Xaa may be Ile or Leu

<400> SEQUENCE: 56

Xaa Xaa Xaa Tyr Xaa Xaa Xaa Xaa Xaa Xaa Xaa Xaa Xaa Xaa Tyr Xaa
1               5                   10                  15

Xaa Xaa

<210> SEQ ID NO 57
<211> LENGTH: 19
<212> TYPE: PRT
<213> ORGANISM: Artificial Sequence
<220> FEATURE:
<223> OTHER INFORMATION: Immunoreceptor tyrosine-based activation motify
      (ITAM)
<220> FEATURE:
<221> NAME/KEY: VARIANT
<222> LOCATION: (1)..(1)
<223> OTHER INFORMATION: Xaa may be Asp or Glu
<220> FEATURE:
<221> NAME/KEY: VARIANT
<222> LOCATION: (2)..(3)
<223> OTHER INFORMATION: Xaa may be any amino acid
<220> FEATURE:
<221> NAME/KEY: VARIANT
<222> LOCATION: (5)..(6)
<223> OTHER INFORMATION: Xaa may be any amino acid
<220> FEATURE:
<221> NAME/KEY: VARIANT
<222> LOCATION: (7)..(7)
<223> OTHER INFORMATION: Xaa may be Ile or Leu
<220> FEATURE:
<221> NAME/KEY: VARIANT
<222> LOCATION: (8)..(16)
<223> OTHER INFORMATION: Xaa may be any amino acid
<220> FEATURE:
<221> NAME/KEY: VARIANT
<222> LOCATION: (17)..(18)
<223> OTHER INFORMATION: Xaa may be any amino acid
<220> FEATURE:
<221> NAME/KEY: VARIANT
<222> LOCATION: (19)..(19)
<223> OTHER INFORMATION: Xaa may be Ile or Leu

<400> SEQUENCE: 57

Xaa Xaa Xaa Tyr Xaa Xaa Xaa Xaa Xaa Xaa Xaa Xaa Xaa Xaa Xaa Tyr
1               5                   10                  15
```

Xaa Xaa Xaa

<210> SEQ ID NO 58
<211> LENGTH: 1575
<212> TYPE: DNA
<213> ORGANISM: Homo sapien

<400> SEQUENCE: 58

```
tgaggacata tctaaatttt ctagttttat agaaggcttt tatccacaag aatcaagatc      60
ttccctctct gagcaggaat cctttgtgca ttgaagactt tagattcctc tctgcggtag     120
acgtgcactt ataagtattt gatggggtgg attcgtggtc ggaggtctcg acacagctgg     180
gagatgagtg aatttcataa ttataacttg gatctgaaga agagtgattt ttcaacacga     240
tggcaaaagc aaagatgtcc agtagtcaaa agcaaatgta gagaaaatgc atctccattt     300
tttttctgct gcttcatcgc tgtagccatg ggaatccgtt tcattattat ggtagcaata     360
tggagtgctg tattcctaaa ctcattattc aaccaagaag ttcaaattcc cttgaccgaa     420
agttactgtg gcccatgtcc taaaaactgg atatgttaca aaaataactg ctaccaattt     480
tttgatgaga gtaaaaactg gtatgagagc caggcttctt gtatgtctca aaatgccagc     540
cttctgaaag tatacagcaa agaggaccag gatttactta aactggtgaa gtcatatcat     600
tggatgggac tagtacacat tccaacaaat ggatcttggc agtgggaaga tggctccatt     660
ctctcaccca acctactaac aataattgaa atgcagaagg gagactgtgc actctatgcc     720
tcgagcttta aaggctatat agaaaactgt tcaactccaa atacatacat ctgcatgcaa     780
aggactgtgt aaagatgatc aaccatctca ataaaagcca ggaacagaga agagattaca     840
ccagcggtaa cactgccaac cgagactaaa ggaaacaaac aaaaacagga caaaatgacc     900
aaagactgtc agatttctta gactccacag gaccaaacca tagaacaatt tcactgcaaa     960
catgcatgat tctccaagac aaaagaagag agatcctaaa ggcaattcag atatccccaa    1020
ggctgcctct cccaccacaa gcccagagtg gatgggctgg gggaggggtg ctgttttaat    1080
ttctaaaggt aggaccaaca cccaggggat cagtgaagga agagaaggcc agcagatcag    1140
tgagagtgca acccccaccct ccacaggaaa ttgcctcatg gcagggcca cagcagagag    1200
acacagcatg ggcagtgcct tccctgcctg tgggggtcat gctgccactt ttaatgggtc    1260
ctccacccaa cggggtcagg gaggtggtgc tgccctagtg ggccatgatt atcttaaagg    1320
cattattctc cagccttaag atcttaggac gttttccttt ctatgatttg tacttgcttg    1380
agtcccatga ctgtttctct tcctctcttt cttccttttg gaatagtaat atccatccta    1440
tgtttgtccc actattgtat tttggaagca cataacttgt ttggtttcac aggttcacag    1500
ttaagaagga attttgcctc tgaataaata gaatcttgag tctcatgcaa aaaaaaaaa    1560
aaaaaaaaa aaaaa                                                      1575
```

<210> SEQ ID NO 59
<211> LENGTH: 6098
<212> TYPE: DNA
<213> ORGANISM: Homo sapien

<400> SEQUENCE: 59

```
gcagttatca tagagcacag tccctcacat cacacagctg cagagatgag taaacaaaga      60
ggaaccttct cagaagtgag tctggcccag gacccaaagc ggcagcaaag gaaacctaaa     120
ggcaataaaa gctccatttc aggaaccgaa caggaaatat tccaagtaga attaaatctt     180
caaaatcctt ccctgaatca tcaagggatt gataaaatat atgactgcca aggtaaaaca     240
```

```
ttaaatatat cttcaatatt attgttctag gatgtgcagt tgaatgcaga agggtgagga    300
aagattaggg aatattttgc acttgtgaga atcggagttc ataattggga tctaaaattc    360
taatatgaaa tcagaagact aattttattc gggcattgtt caactgtaat ctgcggtcca    420
ctcatggaac attatattta ctgaaaatga aatggtatat tctgagagaa agattactag    480
agtagatgta gatttagagg ccagagttta tcattatgtt tccctgtgca tgtgggttct    540
ctagtatgta attctctagt atgtaatcct aatcaactct ctatctcccc tctctcagtg    600
cctctatttc tctccctgca ggtttactgc cacctccaga gaagctcact gccgaggtcc    660
taggaatcat ttgcattgtc ctgatggcca ctgtgttaaa aacaatagtt cttattcctt    720
gtaagcatat tcttgaaaga ttagaaggga acgttttact ttaatgcttg gaagtgcctc    780
aaaatatttc atactgttga agaatagaac tcttatttta ctgtttcttt caaagatcta    840
ttacttcatt tattttttata gaaaaagtta attttattaa agattgtccc cattttaaat    900
aacacacaaa gttcaaagt aagaaactaa actcattatg gttatctaa atattacttt    960 ttataaaaat catttaatt tttctgttac agtcctggaa cagaacaatt cttccccaaa    1020
tacaagaacc cagaaaagta cattttt att ttcaaagttc tgatattagt acaatttgga    1080
accaaaagta atatggttat tctgaatttt tcacaacata aataacaaaa tcattgtaga    1140
gaacatgtgt ttattttttg tgtgtaatct atatatatgt atatacatac acacacaaag    1200
atattttctg atttcataat tcaaaggcat gctatagaag aaaagtattt agaaaaacaa    1260
attaattttt gaaagtggtt acatcaaata ctacaagaga tggtgaagtt tgtgctaaag    1320
tctttaaaaa tgtttatttc aaaggtctat tactttatat attttttatag aaaaagttaa    1380 ttttattaaa gattctcccc attttaaata acacacaaag tttcaaagta agaaactaaa    1440
ctcgttatgg ttcatctaga tatcagtttt tataaaaatc attttaattt ttctattaca    1500
gtcctggagc agaacaattc ttccccgaat acaagaacgc agaaaggtac attttt attt    1560 tcaatgttct gatattagta caatttatat tttgtgtctg ttttaaggca tgtaaaagaa    1620
tagtggcatt tttgcagaaa ataagccata aattcagcca taaatatttg taaagaaaga    1680
ttatgaggca gcatttcctt ttctccagtg agtagaaata ctcacttaaa atcattctac    1740
cctctttctc ccaattaaca gaggtttcct actgctgtga gatgatacca aataaataat    1800
tttactattc taaaaaagca gttgtgtatc agcgatgttc aacacatgtg tagagtgtat    1860
ttttgtttgt tcatttgctt tatatgggaa cacaattagg gaggagaggc taaccctttgt   1920 ctgtgcatgt gtgtatgact gactcagtta ttaaaaatat acatttataa gcctgtaagg    1980
atgcgtaaat atgttaagca catatatgtt tatactgttg aaatatgtga actaattttc    2040 attttttaaaa attcatattg gtctaaatag taattcatat ctttattagc acgtcattgt    2100
ggccattgtc ctgaggagtg gattacatat tccaacagtt gttattacat tggtaaggaa    2160
agaagaactt gggaagagag tttgctggcc tgtacttcga agaactccag tctgcttttct   2220 atagataatg aagaagaaat ggtaagatgt aaatgtttca acatttt at gaaaagcttc    2280 cttcagtgaa taatacattt gtagaaaaca tccatatgtg tgtacatata tttatctcat    2340
atattttcaa gtgtatgtaa tattcaattg attgacttaa taatgttttt aaagttatat    2400
actgctaatg tacatttatt ttcagttttt gttttttcaag gaaaaccatg cttctataag    2460
tgctttgaat ccacaataaa ttttgctatc taatttatc gggcatgata tcatctggtc    2520
atgcagattg atcacaaagt gaatgaatgc atgtgataca agtcagatca tgaaataaaa    2580
```

```
gtttccagct ctagcagttc cacccctgtg tatgccctca tcacttatcc tgactcctct    2640
ccaaaacgca gtcttgactt ttaatattat aaataatgat tgcctgttct tgaatttatt    2700
tatataaagg gaatcaaaca gtgtgaattt catgtctttt tcaatcctat ctgatatttg    2760
tgcaattcct ccatattatt gcagttatca gtagtatgtt actgttcact gctgtactat    2820
gtacaaagaa cagtaagaat ccattgagtc cttgtctctg gatggggaag tgggtctcat    2880
gccctcaggg acaagagga ccctaggtgg tttacggtgc actgttagtc atggggtccc      2940
tttgctgatc ctcctcatcc acagccatcc tggtgtctct tggtatgaga aggaagcact    3000
ttctctagct ccatattggt agcaggtctc ctggtagatc atccttgcca gtggcaccag    3060
ccttgcctgg tattgtggag gggactctcc ttcgataccc tcctcctatt gccaggttgg    3120
gtgtagggaa acagcaggcc taggtcacct tcttctgtcg tgtggaggac ttaacatgct    3180
cacttggaca cttggttgat ccctgatgct agggtcccag acaatttcat ctttctcttt    3240
ccacctttca gagttctcca ttgcttttgt ctttcattaa tcccagagtt tatagttgtt    3300
tttagtaggg agtagcagag agagacgagt ctacaccacc tggccaggac ccctgttatt    3360
ccgcaaaaac cgaatcggat aaaaattgag ggcttatcta gttaaagaat ggtgtggtac    3420
ccagaaaacc caatctgtag cttccatgtc atctatttct gaatgacaac ccctcaattc    3480
ccttctaaat ctccaactct gagaaatata gcacaaaaat agattgattt agtcacagta    3540
tctggagaaa tgaatgcaca gtatcaggaa acttattaaa acccttcctg tgtttattct    3600
gttaattgga gtaactatta cattgcaaga attaaaatgt ctttattaac atgagaataa    3660
gaatgaaagt actaagtata aacgttgaag agttcattta aataaaaaat tcaaacattt    3720
atgaaagttt ttggcactgc aaatagtggt tttcaacttt aatatattgt ttttgtaatg    3780
ttttcataat tattatttaa gtgaaaatta tttcttttct tttagaaatt tctggccagc    3840
atttaccttt cctcatggat tggtgtgttt cgtaacagca gtcatcatcc atgggtgaca    3900
ataaatggtt tggcttttcaa acataagtaa gttcttttgt atggcgctat ataaaaaata    3960
tatataaagg ataaattcag aagaataata tgaataaatt tatgtggaat cattgacatg    4020
aagaaagatg tggaaagtta gtgaaatgtt gatataaata ttttacaata gaccatagta    4080
gtccatatat ttcaaccgct cattggtctg ctagtaacct tcttggttat cagatggacc    4140
aggggtgtcc catctttggc ttctgtgggc cacgttagaa gacgaatagt cttgcccac     4200 acatagaata cactaacact aacgatagct gacgagctaa aaaaaaaaa aaatcacaga     4260 atgtttaag aaagtttacg tatttgtgtt gggccgcatt caaagctgtc ctgggtcacg     4320
tgcggcccat gggcagcgag ttggacaacc tcgagctgga ctatcaggga actgcagtgc    4380 ttgttttat taaaaagcca cgcttacttt tttacttaag aatatcctca agcacaata     4440 atagtgctgt tggcatattg ctataatttt tttattacta gttattgttg tcaatctctt    4500
attgtgccta atttataaat taaactttat cacagttatg aatgtgtaga gaaacataa    4560 tctctctata ggttctgcac tatctgccat ttcaggcatc cactgggtc ttgaaacata    4620 tccctcgtgg atgaagaggg actactctgt tgagtgttca gaataatgac tcttactaat    4680
attatgaaaa atttaattac cctttttccat gaaattcttt tcttacagta catgaaaat    4740 gctttcgtct catgaatcat ttgcttaaaa tgtaacagaa tatggatttt tctccattac    4800
aggataaaag actcagataa tgctgaactt aactgtgcag tgctacaagt aaatcgactt    4860
aaatcagccc agtgtggatc ttcaatgata tatcattgta agcataagct ttagaagtaa    4920
agcatttgcg tttacagtgc atcagataca ttttatattt cttaaaatag aaatattatg    4980
```

-continued

```
attgcataaa tctgaaaatg aattatgtta tttgctctaa tacaaaaatt ctaaatcaat    5040
tattgaaata ggatgcacac aattactaaa gtacagacat cctagcattt gtgtcgggct    5100
cattttgctc aacatggtat ttgtggtttt cagcctttct aaaagttgca tgttatgtga    5160
gtcagcttat aggaagtacc aagaacagtc aaacccatgg agacagaaag tagaatagtg    5220
gttgccaatg tctcagggag gttgaaatag gagatgacca ctaattgata gaacgtttct    5280
ttgtgtcgtg atgaaaactt tctaaatttc agtaatggtg atggttgtaa ctttgcgaat    5340
atactaaaca tcattgattt ttaatcattt taagtgcatg aaatgtatgc tttgtacatg    5400
acacttcaat aaagctatcc agaaaaaaaa aagcctctga tgggattgtt tatgactgca    5460
tttatctcta aagtaatttt aaagattagc ttctttataa tattgacttt tctaatcagt    5520
ataaagtgtt tccttcaatg tactgtgtta tctttaattt ctctctcttg tattttgtat    5580
tttgggggat tgaagtcata cagaaatgta ggtatttac atttatgctt ttgtaaatgg    5640
catcctgatt ctaaaattcc ctttagtaat ttttgttgtt ataaatagaa atacaactga    5700
tgtctgcatt ttgattttat atctacttat tccactgatt ttatatattt aaatctatta    5760
tgtcaactat tgatttattt ctgggtgttc tatataacga gcaattttat ctgcaaatga    5820
tcacactttt atttttttta atccatgtgc tataacttag ttttattttc atttattttc    5880
actggctaag gttttatacc catagttgaa tagaaggcac aatcaaagtt ctttgtggat    5940
catatgcatc attttctggt tttggcaaaa aatacttcaa catgttatac atatttaaaa    6000
agcttggtgt ttttttgcatc ctatctttct catatcgaag cagttttata atcctatttt    6060
ctaatagatt ttatcaattg taacaatttt tattaatt                            6098
```

<210> SEQ ID NO 60
<211> LENGTH: 3000
<212> TYPE: DNA
<213> ORGANISM: Homo sapien
<300> PUBLICATION INFORMATION:
<308> DATABASE ACCESSION NUMBER: AF072845
<309> DATABASE ENTRY DATE: 1998-06-22
<313> RELEVANT RESIDUES IN SEQ ID NO: (1)..(3000)

<400> SEQUENCE: 60

```
aattcccagc cctggagctg gcattccagt gggaggccac tctcagtttc acttggtgac      60 cttcacagc actgaccatg ttggccctat ttctcccctg cttgcttgct tttctatttt     120
attttattat tacattttta ttgttagaga gagggtctca ttctgtcgcc caggctggag     180
tgcagtggca aagtggtgag atctcggctc actgcaacct ccacttgcct cagtctccca     240
agtagctggg attacaggag cctgacacca tgcccgggta attttttgtat ttttgtagag    300 acggggtttc accatattgg cttgaactcc tgatctcagg tgatccccc accttggcct     360 cccaaagtgc tgggattaca ggcatgagcc actgcggtgg cctctcccct gctttcaaga     420
tgccatgctc tcagggtcc cctccctctt tctccatttc cctggcaaag ttcctcctct      480
tcccccattc agtgtgtgtt gtgataggg cagaatcctg tctgcactca cttccttggt      540
gatctcaccc agtcttgtgg ctttaagtac catccataag ccatcaaccc ccaaatttac     600
atctccagac cagccttatc ccctgaactc ctaaatgcag tgaggttatt cagcatctcc     660
acagggagat tgtcaggcat ttccaaccct gtatgcccaa acctcgtcac tttccccgca     720
aacccacttc cctacctttc atctctgcca gcagacactc ccatcttctc agcgtttcat     780
gccagaaggc ttggctgtct aggatccctc tcaaacacac ccacattcat ttaatcagca     840
```

| | |
|---|---|
| aattttcttg gccctacctc caaaatattt ccagatctcc ctagcctgca caccottgcc | 900 |
| acctgtcatt cccacttgga ccaggccagc agcctccctg gtctctctga ccctccccct | 960 |
| gagttcgttc accaaaggca gtaacggaga cacccctca acacacacag gaagcagatg | 1020 |
| gccttgacac cagcagggtg acatccgcta ttgctacttc tctgctcccc cacagttcct | 1080 |
| ctggacttct ctggaccaca gtcctctgcc agaccctgc cagaccccag tccaccatga | 1140 |
| tccatctggg tcacatcctc ttcctgcttt tgctcccagg tgaagccagt ggttacaggg | 1200 |
| gatggtaggc agagcgtttg tgagatgggt gcttgggtga cgtctgcagg gacgggtgat | 1260 |
| gaaagtgggg ttcttctccc tgcaccccct cccttctggg agatccattc tgcttcaggg | 1320 |
| cctgggtcct tggggcgga aggggtgag acagggagtt ctggagggc tgcctgttag | 1380 |
| cgtccccttc tcatggctgg gtctctgctg ccacttccaa tttcttgtca ctctccatgt | 1440 |
| ctctgggagt ccccttccca tgtggtcctg ttccatctct ccagcctgga gattacttct | 1500 |
| caggacacta ccttttccttc tctacaccct atttttttggt ttgtttatt tgagatgggg | 1560 |
| tcttgctctg ttgtccaggc tggagtgcag tggcacaatc acggctcacg gcagccttga | 1620 |
| cttcctgggc tcaggtgatc ctcccagctc agcctcccga gtaactggga ttacaggtgt | 1680 |
| gaaccaacac ttccagctaa tttttgtatt tcttgtagag acgaggtctc actatgttgc | 1740 |
| ccaggctggt ctcgaactcc tgggctcaag cgatcttcct gcctcggcct cccaaagtgc | 1800 |
| tgggatgaca ggcgtgagcc acggtgccag gctgagcatt ctgttttgtg gaccttctct | 1860 |
| ccaccctcat ccaccttctt tctctttcca cagtggctgc agctcagacg actccaggag | 1920 |
| agagatcatc actccctgcc ttttaccctg gcacttcagg tatcacttcc accccagaag | 1980 |
| cttggccaga ggctcccaga acaccccagt ggttctccag gtcaccatcc cacctcccgt | 2040 |
| ccccaaaatca gaggatccgt gtccttctcc gagtcccaga atcagcgacc cccagcctgt | 2100 |
| gttcaggagc acccccgtgtg cccgccgcac agccccgagg gtcctgggac accccagcct | 2160 |
| ctctgcatct gtctcccgtt tcattcccca agcgcaactc caaggaacct gggacccgcc | 2220 |
| ccctcgcagg ggacttcctc tctgcctgtg gccaaagcac agccccagga cgcagagctt | 2280 |
| gagttgtctc cctgttccgg ccccccactct ccaggctctt gttccggatg tgggtccctc | 2340 |
| tctctgccgc tcctggcagg cctcgtggct gctgatgcgg tggcatcgct gctcatcgtg | 2400 |
| ggggcggtgt tcctgtgcgc acgcccacgc cgcagcccg cccaaggtga gggcggagat | 2460 |
| gggcggggcc tggaaggtgt atagtgtccc tagggagggg gtcccaggga gggggcctt | 2520 |
| ggggaagccc tggaggaggt gctggggaaa ccctggggga ggtgcctggg gaacccctg | 2580 |
| aggaaacccc tgaagcaggg ggtccccagg gaagtggaga tatgggtggt caagcttcat | 2640 |
| gctttctctc ccctatcccc agaagatggc aaagtctaca tcaacatgcc aggcaggggc | 2700 |
| tgaccctcct gcagcttgga cctttgactt ctgaccctct catcctggat ggtgtgtggt | 2760 |
| ggcacaggaa ccccgccccc aacttttgga ttgtaataaa acaattgaaa cacctgtagt | 2820 |
| cgtattcttt ctcaaagaac cccagagttc ccaaagcctc cctcccatga actgtttctg | 2880 |
| gatccaaggc cccctcagaa ccccacatg tccccatccc atcagcccaa ggatctggca | 2940 |
| taatgttttt gtgcttcatg tttatttag gagagtattg gggagcggtc tggtctctca | 3000 |

<210> SEQ ID NO 61
<211> LENGTH: 604
<212> TYPE: DNA
<213> ORGANISM: Homo sapien
<300> PUBLICATION INFORMATION:
<308> DATABASE ACCESSION NUMBER: AF019562

<309> DATABASE ENTRY DATE: 1997-08-14
<313> RELEVANT RESIDUES IN SEQ ID NO: (1)..(604)

<400> SEQUENCE: 61

```
ccacgcgtcc gcgctgcgcc acatcccacc ggcccttaca ctgtggtgtc cagcagcatc      60
cggcttcatg gggggacttg aaccctgcag caggctcctg ctcctgcctc tcctgctggc     120
tgtaagtggt ctccgtcctg tccaggccca ggcccagagc gattgcagtt gctctacggt     180
gagcccgggc gtgctggcag ggatcgtgat gggagacctg gtgctgacag tgctcattgc     240
cctggccgtg tacttcctgg gccggctggt ccctcggggg cgaggggctg cggaggcagc     300
gacccggaaa cagcgtatca ctgagaccga gtcgccttat caggagctcc agggtcagag     360
gtcggatgtc tacagcgacc tcaacacaca gaggccgtat tacaaatgag cccgaatcat     420
gacagtcagc aacatgatac ctggatccag ccattcctga agcccaccct gcacctcatt     480
ccaactccta ccgcgataca gacccacaga gtgccatccc tgagagacca gaccgctccc     540
caatactctc ctaaaataaa catgaagcac aaaaaaaaaa aaaaaaaaaa aaaaaaaaa      600
aaaa                                                                 604
```

<210> SEQ ID NO 62
<211> LENGTH: 1677
<212> TYPE: DNA
<213> ORGANISM: Homo sapien
<300> PUBLICATION INFORMATION:
<308> DATABASE ACCESSION NUMBER: NM_198053
<309> DATABASE ENTRY DATE: 2010-08-01
<313> RELEVANT RESIDUES IN SEQ ID NO: (1)..(1677)

<400> SEQUENCE: 62

```
gtcctccact tcctggggag gtagctgcag aataaaacca gcagagactc cttttctcct      60
aaccgtcccg gccaccgctg cctcagcctc tgcctcccag cctctttctg agggaaagga    120
caagatgaag tggaaggcgc ttttcaccgc ggccatcctg caggcacagt tgccgattac    180
agaggcacag agctttggcc tgctggatcc caaactctgc tacctgctgg atggaatcct    240
cttcatctat ggtgtcattc tcactgcctt gttcctgaga gtgaagttca gcaggagcgc    300
agacgccccc gcgtaccagc agggccagaa ccagctctat aacgagctca atctaggacg    360
aagagaggag tacgatgttt tggacaagag acgtggccgg gaccctgaga tggggggaaa    420
gccgcagaga aggaagaacc ctcaggaagg cctgtacaat gaactgcaga agataagat     480
ggcggaggcc tacagtgaga ttgggatgaa aggcgagcgc cggaggggca gggcacga     540
tggcctttac cagggtctca gtacagccac caaggacacc tacgacgccc ttcacatgca    600
ggccctgccc cctcgctaac agccagggga tttcaccact caaaggccag acctgcagac    660
gcccagatta tgagacacag gatgaagcat ttacaacccg gttcactctt ctcagccact    720
gaagtattcc cctttatgta caggatgctt tggttatatt tagctccaaa ccttcacaca    780
cagactgttg tccctgcact cttttaaggga gtgtactccc agggcttacg gccctggcct    840
tgggccctct ggtttgccgg tggtgcaggt agacctgtct cctggcggtt cctcgttctc    900
cctgggaggc gggcgcactg cctctcacag ctgagttgtt gagtctgttt tgtaaagtcc    960
ccagagaaag cgcagatgct agcacatgcc ctaatgtctg tatcactctg tgtctgagtg   1020
gcttcactcc tgctgtaaat ttggcttctg ttgtcacctt cacctccttt caaggtaact   1080
gtactgggcc atgttgtgcc tccctggtga gaggccggg cagaggggca gatgaaaagg   1140
agcctaggcc aggtgcaacc agggagctgc agggcatgg gaaggtgggc gggcagggga   1200
```

```
gggtcagcca gggcctgcga gggcagcggg agcctccctg cctcaggcct ctgtgccgca   1260
ccattgaact gtaccatgtg ctacaggggc cagaagatga acagactgac cttgatgagc   1320
tgtgcacaaa gtggcataaa aaacatgtgg ttacacagtg tgaataaagt gctgcggagc   1380
aagaggaggc cgttgattca cttcacgctt tcagcgaatg acaaaatcat ctttgtgaag   1440
gcctcgcagg aagacccaac acatgggacc tataactgcc cagcggacag tggcaggaca   1500
ggaaaaaccc gtcaatgtac taggatactg ctgcgtcatt acagggcaca ggccatggat   1560
ggaaaacgct ctctgctctg ctttttttct actgttttaa tttatactgg catgctaaag   1620
ccttcctatt ttgcataata aatgcttcag tgaaaaaaaa aaaaaaaaaa aaaaaaa     1677

<210> SEQ ID NO 63
<211> LENGTH: 591
<212> TYPE: DNA
<213> ORGANISM: Homo sapien
<300> PUBLICATION INFORMATION:
<308> DATABASE ACCESSION NUMBER: M33195
<309> DATABASE ENTRY DATE: 1993-04-27
<313> RELEVANT RESIDUES IN SEQ ID NO: (1)..(591)

<400> SEQUENCE: 63
cagaacggcc gatctccagc ccaagatgat tccagcagtg gtcttgctct tactcctttt     60
ggttgaacaa gcagcggccc tgggagagcc tcagctctgc tatatcctgg atgccatcct    120
gtttctgtat ggaattgtcc tcaccctcct ctactgtcga ctgaagatcc aagtgcgaaa    180
ggcagctata accagctatg agaaatcaga tggtgtttac acgggcctga gcaccaggaa    240
ccaggagact tacgagactc tgaagcatga gaaaccacca cagtagcttt agaatagatg    300
cggtcatatt cttctttggc ttctggttct tccagccctc atggttggca tcacatatgc    360
ctgcatgcca ttaacaccag ctggccctac ccctataatg atcctgtgtc ctaaattaat    420
atacaccagt ggttcctcct ccctgttaaa gactaatgct cagatgctgt ttacggatat    480
ttatattcta gtctcactct cttgtcccac ccttcttctc ttccccattc ccaactccag    540
ctaaaatatg ggaagggaga accccaata aaactgccat ggactggact c              591
```